United States Patent
Amari et al.

(10) Patent No.: US 8,604,015 B2
(45) Date of Patent: Dec. 10, 2013

(54) ALKALOID ESTER AND CARBAMATE DERIVATIVES AND MEDICINAL COMPOSITIONS THEREOF

(75) Inventors: Gabriele Amari, Parma (IT); Mauro Riccaboni, Parma (IT); Daniele De Zani, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/458,072

(22) Filed: Apr. 27, 2012

(65) Prior Publication Data

US 2012/0276018 A1 Nov. 1, 2012

(30) Foreign Application Priority Data

Apr. 29, 2011 (EP) .................................. 11164337

(51) Int. Cl.
| | | |
|---|---|---|
| *A01N 43/00* | (2006.01) | |
| *A01N 43/40* | (2006.01) | |
| *A01N 43/36* | (2006.01) | |
| *A61K 31/33* | (2006.01) | |
| *A61K 31/55* | (2006.01) | |
| *A61K 31/44* | (2006.01) | |
| *A61K 31/41* | (2006.01) | |
| *A61K 31/40* | (2006.01) | |

(52) U.S. Cl.
USPC ...... 514/183; 514/212.01; 514/336; 514/354; 514/359; 514/408; 514/478

(58) Field of Classification Search
USPC ............ 514/183, 212.01, 336, 354, 359, 408, 514/478
See application file for complete search history.

(56) References Cited

U.S. PATENT DOCUMENTS

2011/0319444 A1   12/2011   Amari et al.

FOREIGN PATENT DOCUMENTS

| CN | 101 955 457 | 1/2011 |
|---|---|---|
| EP | 1 640 364 | 3/2006 |
| EP | 2 154 136 | 2/2010 |
| WO | 95/06635 | 3/1995 |
| WO | 01/85727 | 11/2001 |
| WO | 2004/005285 | 1/2004 |
| WO | 2004/052365 | 6/2004 |

OTHER PUBLICATIONS

Grob et al (Helvetica Chimica Acta, 60:2, 1977, 391-396).*
U.S. Appl. No. 13/827,101, filed Mar. 14, 2013, Caligiuri, et al.
European Search Report in Application No. 11164337.5, issued Oct. 24, 2011.
Chinni Mahesh et al., Tetrahedron Letters vol. 48 (2007) pp. 55-59.
Karine Flinois et al., Tetrahedron vol. 58 (2002) pp. 4707-4716.
U.S. Appl. No. 13/729,388, filed Dec. 28, 2012, Amari, et al.

* cited by examiner

*Primary Examiner* — Benjamin Packard
(74) *Attorney, Agent, or Firm* — Oblon, Spivak, McClelland, Maier & Neustadt, L.L.P.

(57) ABSTRACT

Compounds according to formula (I) are effective for the treatment of broncho-obstructive and inflammatory diseases.

15 Claims, No Drawings

ALKALOID ESTER AND CARBAMATE DERIVATIVES AND MEDICINAL COMPOSITIONS THEREOF

CROSS REFERENCES TO RELATED APPLICATIONS

This application claims priority to European Patent Application No. 11164337.5, filed on Apr. 29, 2011, which is incorporated herein by reference in its entirety.

BACKGROUND OF THE INVENTION

1. Field of the Invention

The present invention relates to compounds which act as muscarinic receptor antagonists, to methods of preparing such compounds, to compositions which contain such a compound, and therapeutic uses of such compounds.

2. Discussion of the Background

Quaternary ammonium salts acting as muscarinic (M) receptor antagonist drugs are currently used in therapy to induce bronchodilation for the treatment of respiratory diseases. Examples of well known M receptor antagonists are for instance represented by ipratropium bromide and tiotropium bromide.

Some chemical classes acting as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are for instance disclosed in WO 02/051841, WO 03/053966, and WO 2008/012290, which are incorporated herein by reference in their entireties. WO 2010/015324, which is incorporated herein by reference in its entirety, describes carbonate derivatives and their use as M3 antagonists.

There remains, however, a need for compounds characterized by a good activity as M3 antagonists and by an improved pulmonary stability.

SUMMARY OF THE INVENTION

Accordingly, it is one object of the present invention to provide novel compounds which act as muscarinic receptor antagonists.

It is another object of the present invention to provide novel methods of preparing such a compound.

It is another object of the present invention to provide novel compositions which contain such a compound.

It is another object of the present invention to provide novel therapeutic uses of such a compounds.

These and other objects, which will become apparent during the following detailed description, have been achieved by the inventors' discovery that compounds of general formula (I), described below, are characterized by a good activity as M3 antagonists and by an improved pulmonary stability.

Thus, the present invention provides compounds of general formula (I), which act as muscarinic receptor antagonists.

The present invention also provides processes for the preparation of such a compound.

The present invention also provides compositions which contain such a compound.

The present invention also provides therapeutic uses of such a compound.

The present invention also provides combinations of such a compound with other pharmaceutical active ingredients, for instance, those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The compounds of the present invention are characterized by a good activity as M3 antagonists and by an improved pulmonary stability.

DETAILED DESCRIPTION OF THE PREFERRED EMBODIMENTS

Thus, in a first embodiment, the present invention provides novel compounds of general formula (I):

(I)

wherein:
X may be O or S;
X' may be O or S;
Y may be NH or absent;
$R_1$ is aryl, heteroaryl, aryl($C_1$-$C_6$)alkyl, heteroaryl($C_1$-$C_6$)alkyl, or a group of formula (a) or (b):

wherein
$R_3$ and $R_4$ are the same or different and may be independently H or are selected from the group consisting of ($C_3$-$C_8$)cycloalkyl, aryl, aryl($C_1$-$C_6$)alkyl, heteroaryl, and heteroaryl($C_1$-$C_6$)alkyl, which may be optionally substituted by one or more substituents selected from the group consisting of halogen atoms, —OH, ($C_1$-$C_6$)haloalkyl, ($C_1$-$C_6$)alkoxy, oxo (=O), —SH, —$NO_2$, —CN, —$CONH_2$, —COOH, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, and ($C_1$-$C_6$)alkyl or, when $R_3$ and $R_4$ are both independently aryl or heteroaryl they may be linked to each other through a ($CH_2$), with r=0-2, to form a tricyclic ring system wherein any of the methylene ($CH_2$), groups may be optionally replaced by a heteroatom or heteroaromatic group selected from O, S, N, and NH, and with the proviso that $R_3$ and $R_4$ are not simultaneously H;
$R_2$ is a group of formula (c) or (d):

(c)

-continued

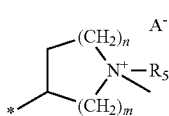
(d)

wherein
m=1, 2m or 3;
n=1, 2 or 3;
$A^-$ is a physiologically acceptable anion;
$R_5$ is a group of formula (e):

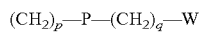
(e)

wherein
p is 0 or an integer from 1 to 4;
q is 0 or an integer from 1 to 4;
P is absent or is selected from the group consisting of —O—, —S—, —S(O)—, —S($O_2$)—, —C(O)—, —CO(O)—, —N($R_6$)—, —CH=CH—, —N($R_6$)(S$O_2$)—, —N($R_6$)CO(O)—, —N($R_6$)C(O)—, —S$O_2$N($R_6$)—, —CO(O)N($R_6$)— and —C(O)N($R_6$)—;
W is selected from the group consisting of H, ($C_1$-$C_6$)alkyl, ($C_2$-$C_6$)alkenyl, ($C_3$-$C_8$)cycloalkyl, ($C_3$-$C_8$)heterocloalkyl, aryl, and heteroaryl, optionally substituted by one or more substituents selected from the group consisting of halogen atoms, —OH, oxo (=O), —SH, —N$O_2$, —N($R_6$)$_2$, —CN, —CON($R_6$)$_2$, —COOH, —NHCO$R_6$, —C$O_2$$R_6$, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)alkoxy, aryl, and heteroaryl;
$R_6$ is, independently in each occurrence, H or is selected from the group consisting of ($C_1$-$C_6$)alkyl, ($C_1$-$C_6$)haloalkyl, ($C_2$-$C_6$)alkynyl, ($C_2$-$C_6$)alkenyl, ($C_3$-$C_8$)cycloalkyl, heteroaryl, and aryl, optionally substituted by one or more substituents selected from the group consisting of halogen atoms, —OH, oxo (=O), —SH, —N$O_2$, —CN, —CON$H_2$, —COOH, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, ($C_3$-$C_8$)cycloalkyl, ($C_1$-$C_6$)alkyl and ($C_1$-$C_6$)alkoxy;
and pharmaceutically acceptable salts thereof.

The present invention is also directed to compounds of general formula (IV):

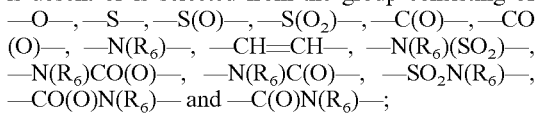
(IV)

wherein Q represents a group of formula (f) or (g):

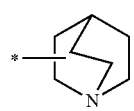
(f)

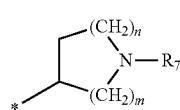
(g)

$R_7$ is selected from the group consisting of ($C_1$-$C_6$)alkyl and aryl($C_1$-$C_6$)alkyl, and $R_1$, X, X', n, m and Y have the above reported meanings in formula (I).

The term "halogen atoms" as used herein includes fluorine, chlorine, bromine, and iodine.

The expression "($C_1$-$C_6$)alkyl" refers to straight-chained or branched alkyl groups wherein the number of carbon atoms is from 1 to 6. Examples of groups are methyl, ethyl, n-propyl, isopropyl, t-butyl, pentyl, hexyl and the like.

The term "($C_1$-$C_6$)alkoxy" refers to alkyl-oxy (e.g. alkoxy) groups, being the alkyl portion as above defined. Examples of said groups may thus comprise methoxy, ethoxy, n-propoxy, isopropoxy, n-butoxy, isobutoxy, sec-butoxy, tert-butoxy, pentoxy, hexoxy. and the like.

The derived expression "($C_1$-$C_6$)alkoxycarbonyl", refers to alkoxy-CO— groups wherein alkoxy is as defined above.

The expressions "($C_1$-$C_6$)haloalkyl" and "($C_1$-$C_6$)haloalkoxy" refer to the above "($C_1$-$C_6$)alkyl" and "($C_1$-$C_6$) alkoxy" groups wherein one or more hydrogen atoms are replaced by one or more halogen atoms, which can be the same or different from each other.

The expressions "($C_1$-$C_6$)alkylsulfanyl," "($C_1$-$C_6$)alkylsulfinyl," and "($C_1$-$C_6$)alkylsulfonyl" refer respectively to alkyl-S—, alkyl-SO—, and alkyl-S$O_2$— groups.

The expression "($C_2$-$C_6$)alkenyl" refers to straight or branched carbon chains with one or more double bonds. Examples of said groups may thus comprise ethenyl, propenyl, butenyl, pentenyl, hexenyl and the like.

The expression "($C_2$-$C_6$)alkynyl" refers to straight or branched carbon chains with one or more triple bonds. Examples of said groups may thus comprise ethinyl, propinyl, butinyl, pentinyl, hexinyl, and the like.

The expression "($C_3$-$C_8$)cycloalkyl" refers to mono or bi-cycloaliphatic hydrocarbon groups with from 3 to 8 carbon atoms. Examples include cyclopropyl, cyclobutyl, cyclopentyl, cyclohexyl, cycloheptyl, bicyclo[2.2.1]hept-2-yl, and the like.

The derived expression "($C_3$-$C_8$)heterocycloalkyl" refers to ($C_3$-$C_8$)cycloalkyl groups, in which at least one ring carbon atom is replaced by a heteroatom or heteroaromatic group (e.g. N, NH, S, or O). Examples include quinuclidinyl, pyrrolidinyl, piperidinyl and the like.

The expression "aryl" refers to mono-, bi-, or tricyclic ring systems having 5 to 20, preferably from 5 to 15, ring atoms, and wherein at least one ring is aromatic.

The expression "heteroaryl" refers to mono-, bi- or tricyclic ring systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoazolyl), oxazole (oxazolyl), isothiazole (isothiazolyl), thiazole (thiazolyl), pyridine (pyridinyl), imidazolidine (imidazolidinyl), furan (furanyl) radicals, and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazine radicals, and the like.

Examples of suitable aryl or heteroaryl tricyclic systems include fluorene radicals as well as benzocondensed derivatives of the aforementioned heteroaryl bicyclic systems.

The expressions "aryl($C_1$-$C_6$)alkyl" and "heteroaryl($C_1$-$C_6$)alkyl" refer to a "($C_1$-$C_6$)alkyl" respectively substituted by one or more aryl or heteroaryl groups as defined above.

Advantageously, the physiologically acceptable anions $A^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate, preferably chloride, bromide, and trifluoroacetate.

Besides the presence of $A^-$ anion, whenever further basic amino groups are present in the compounds of formula (I), additional physiological acceptable anions, among those formerly indicated, may be present. Likewise, in the presence of acidic groups such as —COOH groups, corresponding physiological cation salts may be present as well, for instance including alkaline or alkaline earth metal ions.

In the present description, and unless otherwise provided, within formula (I) or (IV), Y may represent a divalent —NH— group or, whenever, absent, it clearly represents a single bond so as to provide compounds $R_1$—X—C(=X')$R_2$ or $R_1$—X—C(=X')Q.

Furthermore, when both $R_3$ and $R_4$ are independently selected from aryl or heteroaryl groups, the said groups may be linked to each other through a (CH$_2$), group, so as to form a tricyclic ring system.

From all the above, it is clear to the skilled person that, when r is 0, the said $R_3$ and $R_4$ groups are linked to each other through a bond.

Unless otherwise provided, within formula (I) and (IV), $R_2$ and Q groups being represented by groups (c), (d) and (f), (g), the asterisks in these latter represent their point of attachment to the rest of the molecule.

As an example, the following groups can be highlighted:

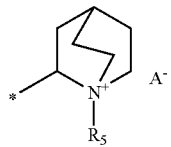
(c1)

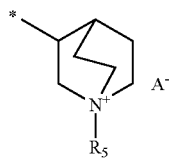
(c2)

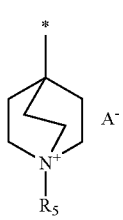
(c3)

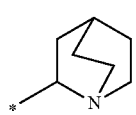
(f1)

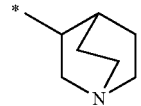
(f2)

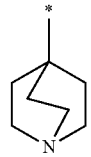
(f3)

It will be apparent that the compounds of general formula (I) and (IV) may contain asymmetric centers. Therefore the invention also includes the optical stereoisomers and mixtures thereof.

Where the compounds according to the present invention possess two or more asymmetric centers, they may additionally exist as diastereoisomers. It is to be understood that all such isomers and mixtures thereof in any proportion are encompassed within the scope of the present invention.

More in particular, the active compounds of formula (I) and (IV) show at least one chiral center, which is represented by the carbon atom in Q or $R_2$ and which is directly linked to group Y.

Therefore, according to a specific embodiment, in compound (I), the carbon atom of $R_2$ group being linked to Y is in the form of (S)-enantiomer when $R_2$ is a group of formula (c).

According to a preferred embodiment, in compound (I), the carbon atom of $R_2$ group being linked to Y is in the form of (R)-enantiomer when $R_2$ is a group of formula (c).

According to another embodiment, in compound (IV), the carbon atom of Q group being linked to Y is in the form of (S)-enantiomer when Q is a group of formula (f), or a group of formula (g), in this latter case obviously except when m is 2 and n is 1, m is 3 and n is 2.

According to a preferred embodiment, in compound (IV), the carbon atom of Q group being linked to Y is in the form of (R)-enantiomer when Q is a group of formula (f), or a group of formula (g), in this latter case obviously except when m is 2 and n is 1, m is 3 and n is 2.

In the compounds of general formula (I) of the present invention, when $R_2$ is a group of formula (a) and $R_3$ and $R_4$ have different meanings, the carbon atom bearing $R_3$ and $R_4$ is a chiral center.

Moreover, within the compounds of formula (I), when $R_1$ represents a group of formula (b), $R_3$ is bound to the carbon atom bearing a double bond in any of the possible (Z) or (E) configurations and presently identified through the symbol

∿∿ $R_3$

A first preferred group of compounds is that of general formula (IVA):

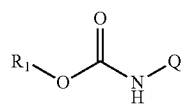
(IVA)

wherein R₁ is a group of formula (a):

(a)

wherein R₃ and R₄ are the same or different and are H or selected from the group consisting of aryl and heteroaryl, which may be optionally substituted by one or more substituents selected from the group consisting of halogen atoms, $(C_1-C_6)$alkoxy, and $(C_1-C_6)$haloalkyl, Q is a group of formula (f) or (g):

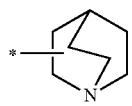
(f)

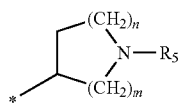
(g)

wherein n=m=1 and R₅ is a group of formula (e):

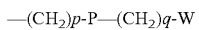 (e)

wherein p=0, P is absent, q=1 and W is aryl.

Still more preferred, within this class, are the compounds of general formula (IVA) wherein R₁ is selected from bis(3-fluorophenyl)methyl, benzhydryl, (4-methoxyphenyl)(phenyl)methyl, (2-fluorophenyl)(4-fluorophenyl)methyl, (2-fluorophenyl)(3-fluorophenyl)methyl, ((3,4-difluorophenyl)(phenyl)methyl, 4-(trifluoromethyl)phenyl)methyl, (2-chlorophenyl)(4-chlorophenyl)methyl, and thiophen-2-ylmethyl, and Q is selected from quinuclidinyl and benzylpyrrolidinyl.

A second preferred group of compounds is that of general formula (IA):

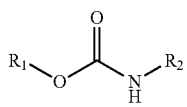
(IA)

wherein R₁ is a group of formula (a):

(a)

wherein R₃ and R₄ are the same or different and are H or selected from the group consisting of aryl and heteroaryl, which may be optionally substituted by one or more substituents selected from the group consisting of halogen atoms, $(C_1-C_6)$alkoxy, and $(C_1-C_6)$haloalkyl, R₂ is a group of formula (c) or (d):

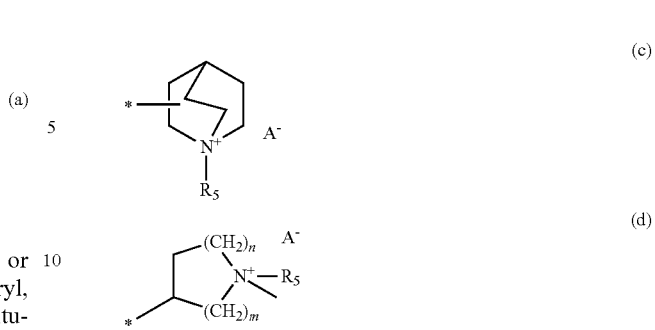

wherein n=m=1 and R₅ is a group of formula (e) wherein p is 0, 1, 2 or 3, P is absent or is selected from the group consisting of —O—, —C(=O)— and —CONH—, q is 0, 1 or 2, and W is selected from the group consisting of $(C_1-C_6)$alkyl, $(C_2-C_6)$alkenyl, aryl, and heteroaryl optionally substituted by one or more substituents selected from the group consisting of halogen atoms, —OH, —CN, $(C_1-C_6)$alkyl, and $(C_1-C_6)$alkoxy.

Still more preferred, within this class, are the compounds of general formula (IA) wherein R₁ is selected from bis(3-fluorophenyl)methyl, benzhydryl, bis(4-fluorophenyl)methyl, (4-methoxyphenyl)(phenyl)methyl, (2-fluorophenyl)(4-fluorophenyl)methyl), (3,4-difluorophenyl)-(phenyl)-methyl, (4-(trifluoromethyl)phenyl)methyl, (2-chlorophenyl)-(4-chlorophenyl)-methyl, and thiophen-2-ylmethyl and R₂ is selected from (2-oxo-2-(thiophen-3-yl)ethyl)-1-azoniabicyclo[2.2.2]octanyl, (2-(4-chlorophenyl)-2-oxoethyl)-1-azoniabicyclo[2.2.2]octanyl, (2-oxo-2-p-tolylethyl)-1-azoniabicyclo[2.2.2]-octanyl, (2-(4-fluorophenyl)-2-oxoethyl)-1-azoniabicyclo[2.2.2]octanyl, (2-(3-fluorophenyl)-2-oxoethyl)-1-azoniabicyclo-[2.2.2]octanyl, (2-(2-fluorophenyl)-2-oxoethyl)-1-azoniabicyclo[2.2.2]octanyl, (2-(4-methoxyphenyl)-2-oxoethyl)-1-azoniabicyclo[2.2.2]octanyl, (2-(4-hydroxyphenyl)-2-oxoethyl)-1-azoniabicyclo[2.2.2]octanyl, (bis(3-fluorophenyl)methoxy)carbonylamino)-1-azoniabicyclo[2.2.2]octanyl, (2-(5-chlorothiophen-2-yl)-2-oxoethyl)-1-azoniabicyclo [2.2.2]octanyl, (2-oxo-2-(thiazol-2-yl)ethyl)-1-azoniabicyclo-[2.2.2]octanyl, (2-oxopropyl)-1-azoniabicyclo[2.2.2]octanyl, (3-methylbut-2-enyl)-1-azoniabicyclo-[2.2.2]octanyl, benzyl-1-azoniabicyclo[2.2.2]octanyl, (3-phenoxypropyl)-1-azoniabicyclo[2.2.2]octanyl, (2-(5-cyanothiophen-2-yl)-2-oxoethyl)-1-azoniabicyclo[2.2.2]octanyl, (2-oxo-2-(pyridin-2-yl)ethyl)-1-azoniabicyclo-[2.2.2]octanyl, (2-(isoxazol-3-ylamino)-2-oxoethyl)-1-azoniabicyclo[2.2.2]-octanyl, (2-oxo-2-(thiophen-2-yl)ethyl)-1-azoniabicyclo-[2.2.2]octanyl, (2-oxo-2-phenylethyl)-1-azoniabicyclo [2.2.2]octanyl, (2-phenoxyethyl)-1-azoniabicyclo[2.2.2]octanyl, (2,3-dihydrobenzofuran-5-yl)ethyl)-1-azoniabicyclo[2.2.2]octanyl, (4-fluorophenethyl)-1-azoniabicyclo-[2.2.2]octanyl, and benzylmethylpyrrolidinyl.

A third preferred group of compounds is that of general formula (IVB):

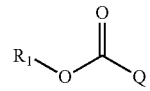
(IVB)

wherein R₁ is aryl or a group of formula (a):

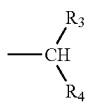
(a)

R₃ and R₄ are the same or different and are H or are selected from the group consisting of aryl, aryl(C₁-C₆)alkyl, and heteroaryl, which may be optionally substituted by one or more substituents selected from the group consisting of halogen atoms, (C₁-C₆)alkoxy, and (C₁-C₆)haloalkyl or when R₃ and R₄ are both independently aryl or heteroaryl they may be linked to each other through a (CH₂)ᵣ with r=0-2, to form a tricyclic ring system wherein any of the methylene (CH₂)ᵣ groups may be a heteroatom or heteroaromatic group selected from O, S, N, and NH, and with the proviso that R₃ and R₄ are not simultaneously H; Q is a group of formula (f) or (g):

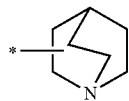
(f)

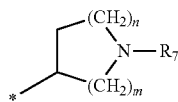
(g)

wherein n is 1, m is 2 and R₇ is a group of formula (f) wherein p=0, P is absent, q is 0 or 1 and W is (C₁-C₆)alkyl.

Still more preferred, within this class, are the compounds of general formula (IVB) wherein R₁ is selected from (3,4-difluorophenyl)(phenyl)methyl, bis(3-fluorophenyl)methyl, 1,2-diphenylethyl, bis(4-chlorophenyl)methyl, bis(4-fluorophenyl)methyl, benzhydryl, (4-methoxyphenyl)(phenyl)methyl, (2-chlorophenyl)(4-chlorophenyl)methyl, 1,2-diphenylvinyl, 3-fluorobenzyl, benzyl, and fluorenyl, and Q is selected from quinuclidin-3-yl, and methylpiperidinyl.

A fourth preferred group of compounds is that of general formula (IB):

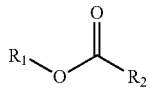
(IB)

wherein R₁ is aryl or a group of formula (a) or (b):

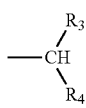
(a)

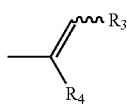
(b)

wherein R₃ and R₄ are the same or different and are H or selected from the group consisting of aryl, aryl(C₁-C₆)alkyl, and heteroaryl, which may be optionally substituted by one or more substituents selected from the group consisting of halogen atoms, (C₁-C₆)alkoxy, and (C₁-C₆)haloalkyl or when R₃ and R₄ are both independently aryl or heteroaryl they may be linked to each other through a (CH₂)ᵣ with r=0-2, wherein when n=0, to form a tricyclic ring system wherein any of the methylene (CH₂)ᵣ may be a heteroatom or heteroaromatic group selected from O, S, N and NH, and with the proviso that R₃ and R₄ are not simultaneously H, R₂ is a group of formula (c) or (d):

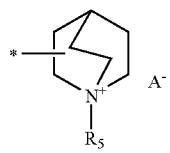
(c)

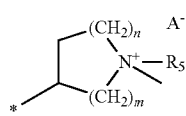
(d)

wherein n=1 or 2, m=1 and R₅ is a group of formula (e), wherein p=1 or 3, P is absent or is selected from the group consisting of —O—, —C(=O)— and —C(=O)O—, q=1 and W is selected from the group consisting of (C₁-C₆)alkyl, (C₂-C₆)alkenyl, aryl, and heteroaryl optionally substituted by one or more substituents selected from the group consisting of halogen atoms, OH, CN, (C₁-C₆)alkyl, (C₁-C₆)alkoxycarbonyl, and (C₁-C₆)alkoxy.

Still more preferred, within this class, are the compounds of general formula (IB), wherein R₁ is selected from bis(3-fluorophenyl)methyl, 1,2-diphenylethyl, bis(4-chlorophenyl)methyl, bis(4-fluorophenyl)methyl, (4-methoxyphenyl)(phenyl)methyl, 3-fluorobenzyl, 1,2-diphenylvinyl, 3-fluorobenzyl, benzyl, (3,4-difluorophenyl)(phenyl)methyl, fluorenyl and diphenylvinyl and R₂ is selected from 2-oxo-2-phenylethyl-1-azoniabicyclo[2.2.2]octanyl, 2-oxo-2-(thiophen-2-yl)ethyl-1-azoniabicyclo-[2.2.2]octanyl, 2-oxo-2-(thiophen-3-yl)ethyl-1-azoniabicyclo[2.2.2]octanyl, 2-(4-methoxyphenyl)-2-oxoethyl)-1-azoniabicyclo[2.2.2]octanyl, 2-(4-fluorophenyl)-2-oxoethyl)-1-azoniabicyclo[2.2.2]octanyl, 2-oxo-2-p-tolylethyl)-1-azoniabicyclo[2.2.2]octanyl, 2-(5-chlorothiophen-2-yl)-2-oxoethyl)-1-azoniabicyclo[2.2.2]octanyl, 2-(4-chlorophenyl)-2-oxoethyl-1-azoniabicyclo[2.2.2]octanyl, 1-(2-oxopropyl)-1-azoniabicyclo[2.2.2]octanyl, 1-(2-tert-butoxy-2-oxoethyl)-1-azoniabicyclo[2.2.2]octanyl, 1-(2-oxo-2-(pyridin-2-yl)ethyl)-1-azoniabicyclo[2.2.]octanyl, 1-(2-(3-(ethoxycarbonyl)-isoxazol-5-yl)-2-oxoethyl)-1-azoniabicyclo[2.2.2]octanyl, 1-(2-(4-hydroxyphenyl)-2-oxoethyl)-1-azoniabicyclo[2.2.2]octanyl, 1-(2-(benzothiophen-5-yl)-2-oxoethyl)-1-azoniabicyclo[2.2.2]octanyl, 1-benzyl-1-azoniabicyclo[2.2.2]octanyl, 1-(2-oxo-2-(thiophen-2-yl)ethyl)-1-azoniabicyclo[2.2.2]octanyl, and 1-methyl-1-(2-oxo-2-(thiophen-2-yl)ethyl)piperidinyl.

A fifth preferred group of compounds is that of general formula (IC):

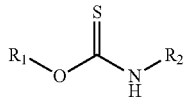
(IC)

wherein $R_1$ is a group of formula (a) wherein $R_3$ and $R_4$ are independently aryl groups, which may be optionally substituted by one or more halogen atoms, $R_2$ is a group of formula (c):

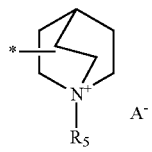
(c)

wherein $R_5$ is a group of formula (e) with p=1, P is —C(=O)—, q is 0, and W is heteroaryl.

Still more preferred, within this class, are the compounds of general formula (IC) wherein $R_1$ is bis(3-fluorophenyl)methyl and $R_2$ is (2-oxo-2-(thiophen-2-yl)ethyl)-1-azoniabicyclo[2.2.2]octanyl.

A sixth preferred group of compounds is that of general formula (IVC):

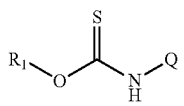
(IVC)

wherein $R_1$ is a group of formula (a) wherein $R_3$ and $R_4$ are independently aryl groups, optionally substituted by one or more halogen atoms, Q is a group of formula (f):

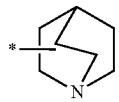
(f)

Still more preferred, within this class, are the compounds of general formula (IVC) wherein $R_1$ is bis(3-fluorophenyl)methyl and Q is quinuclidin-3-yl.

A seventh preferred group of compounds is that of general formula (ID):

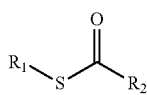
(ID)

wherein $R_1$ is a group of formula (a) wherein $R_3$ and $R_4$ are independently aryl groups, which may be optionally substituted by one or more halogen atoms, $R_2$ is a group of formula (c):

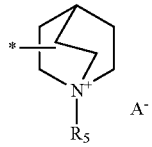
(c)

wherein $R_5$ is a group of formula (e) with p=1, P is —C(=O)—, q is 0, and W is heteroaryl.

Still more preferred, within this class, are the compounds of general formula (ID) wherein $R_1$ is benzyl and $R_2$ is (2-oxo-2-(thiophen-2-yl)ethyl)-1-azoniabicyclo[2.2.2]octanyl.

An eighth preferred group of compounds is that of general formula (IVD):

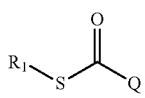
(IVD)

wherein $R_1$ is a group of formula (a) wherein $R_3$ and $R_4$ are independently aryl groups, optionally substituted by one or more halogen atoms, Q is a group of formula (f):

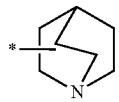
(f)

Still more preferred, within this class, are the compounds of general formula (IVC) wherein $R_1$ is benzyl and Q is quinuclidinyl.

The present invention also provides pharmaceutical compositions of compounds of formula (I) or (IV) alone or in combination with or in admixture with one or more pharmaceutically acceptable carriers and/or excipients.

The present invention also provides the use of compounds of formula (I) or (IV) for preparing a medicament.

In a further aspect, the present invention provides the use of compounds of formula (I) or (IV) for the prevention and/or treatment of any broncho-obstructive or inflammatory disease, preferably asthma or chronic bronchitis or chronic obstructive pulmonary disease (COPD).

In a further aspect, the present invention provides the use of compounds of formula (I) or (IV) for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula (I) or (IV).

The present invention also provides pharmaceutical compositions suitable for administration by inhalation.

Inhalable preparations include inhalable powders, propellant-containing metering aerosols or propellant-free inhalable formulations.

The invention is also directed to a device which may be a single- or multi-dose dry powder inhaler, a metered dose inhaler and a soft mist nebulizer comprising the compounds of formula (I) or (IV).

The invention is also directed to a kit comprising the pharmaceutical compositions of compounds of formula (I) or (IV) alone or in combination with or in admixture with one or more pharmaceutically acceptable carriers and/or excipients and a device which may be a single- or multi-dose dry powder inhaler, a metered dose inhaler or a soft mist nebulizer comprising the compounds of general formula (I) or (IV).

The present invention is also directed to a process for the preparation of compounds of general formula (IV) and (I), which process comprises:

(a) reacting a compound of general formula (II):

(II)

wherein z is a carboxyl group or its corresponding acyl chloride derivative, or an amino group and Q is as defined above, with a compound of general formula (III):

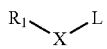
(III)

wherein L is H or an alkaline or alkaline earth metal, $R_1$ and X are as defined above, to obtain a compound of general formula (IV):

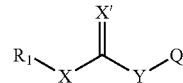
(IV)

wherein X', Q and Y are as described above, the reaction being carried out in the presence of a suitable amount(s) of a condensing agent(s); and optionally, (b) alkylating the compound of general formula (IV) with an agent of general formula (VI):

$R_5$-A  (VI)

wherein $R_5$ and A are as described above, to give compounds of general formula (I):

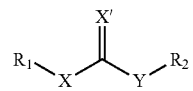
(I)

According to specific embodiments, the present invention provides the compounds reported below:

| Compound | Chemical name |
| --- | --- |
| 1 | (R)-bis(3-fluorophenyl)methyl quinuclidin-3-ylcarbamate |
| 2 | (R)-benzhydryl quinuclidin-3-ylcarbamate |
| 3 | (R)-bis(4-fluorophenyl)methyl quinuclidin-3-ylcarbamate |
| 4 | (4-methoxyphenyl)(phenyl)methyl (R)-quinuclidin-3-ylcarbamate |
| 5 | (2-fluorophenyl)(4-fluorophenyl)methyl (R)-quinuclidin-3-ylcarbamate |
| 6 | (2-fluorophenyl)(3-fluorophenyl)methyl (R)-quinuclidin-3-ylcarbamate |
| 7 | (3,4-difluorophenyl)(phenyl)methyl (R)-quinuclidin-3-ylcarbamate |
| 8 | bis(3-fluorophenyl)methyl quinuclidine-3-carboxylate |
| 9 | 1,2-diphenylethyl quinuclidine-3-carboxylate |
| 10 | bis(4-chlorophenyl)methyl quinuclidine-3-carboxylate |
| 11 | (R)-3-((bis(3-fluorophenyl)methoxy)carbonylamino)-1-(2-oxo-2-(thiophen-3-yl)ethyl)-1-azoniabicyclo[2.2.2]octane bromide |
| 12 | (R)-3-((bis(3-fluorophenyl)methoxy)carbonylamino)-1-(2-(4-chlorophenyl)-2-oxoethyl)-1-azoniabicyclo[2.2.2]octane bromide |
| 13 | (R)-3-((bis(3-fluorophenyl)methoxy)carbonylamino)-1-(2-oxo-2-p-tolylethyl)-1-azoniabicyclo[2.2.2]octane bromide |
| 14 | (R)-3-((bis(3-fluorophenyl)methoxy)carbonylamino)-1-(2-(4-fluorophenyl)-2-oxoethyl)-1-azoniabicyclo[2.2.2]octane bromide |
| 15 | (R)-3-((bis(3-fluorophenyl)methoxy)carbonylamino)-1-(2-(3-fluorophenyl)-2-oxoethyl)-1-azoniabicyclo[2.2.2]octane bromide |
| 16 | (R)-3-((bis(3-fluorophenyl)methoxy)carbonylamino)-1-(2-(2-fluorophenyl)-2-oxoethyl)-1-azoniabicyclo[2.2.2]octane bromide |
| 17 | (R)-3-((bis(3-fluorophenyl)methoxy)carbonylamino)-1-(2-(4-methoxyphenyl)-2-oxoethyl)-1-azoniabicyclo[2.2.2]octane bromide |
| 18 | (R)-3-((bis(3-fluorophenyl)methoxy)carbonylamino)-1-(2-(4-hydroxyphenyl)-2-oxoethyl)-1-azoniabicyclo[2.2.2]octane bromide |
| 19 | (R)-1-(2-(benzo[b]thiophen-5-yl)-2-oxoethyl)-3-((bis(3-fluorophenyl)methoxy)carbonylamino)-1-azoniabicyclo[2.2.2]octane bromide |
| 20 | (R)-3-((bis(3-fluorophenyl)methoxy)carbonylamino)-1-(2-(5-chlorothiophen-2-yl)-2-oxoethyl)-1-azoniabicyclo[2.2.2]octane bromide |
| 21 | (R)-3-((bis(3-fluorophenyl)methoxy)carbonylamino)-1-(2-oxo-2-(thiazol-2-yl)ethyl)-1-azoniabicyclo[2.2.2]octane bromide |
| 22 | (R)-3-((bis(3-fluorophenyl)methoxy)carbonylamino)-1-(2-oxopropyl)-1-azoniabicyclo[2.2.2]octane bromide |
| 23 | (R)-3-((bis(3-fluorophenyl)methoxy)carbonylamino)-1-(3-methylbut-2-enyl)-1-azoniabicyclo[2.2.2]octane bromide |
| 24 | (R)-1-benzyl-3-((bis(3-fluorophenyl)methoxy)carbonylamino)-1-azoniabicyclo[2.2.2]octane bromide |

-continued

| Compound | Chemical name |
|---|---|
| 25 | (R)-3-((bis(3-fluorophenyl)methoxy)carbonylamino)-1-(3-phenoxypropyl)-1-azoniabicyclo[2.2.2]octane bromide |
| 26 | (R)-3-((bis(3-fluorophenyl)methoxy)carbonylamino)-1-(2-(5-cyanothiophen-2-yl)-2-oxoethyl)-1-azoniabicyclo[2.2.2]octane bromide |
| 27 | (R)-3-((bis(3-fluorophenyl)methoxy)carbonylamino)-1-(2-oxo-2-(pyridin-2-yl)ethyl)-1-azoniabicyclo[2.2.2]octane bromide |
| 28 | (R)-3-((bis(3-fluorophenyl)methoxy)carbonylamino)-1-(2-(isoxazol-3-ylamino)-2-oxoethyl)-1-azoniabicyclo[2.2.2]octane chloride |
| 29 | (R)-3-((bis(3-fluorophenyl)methoxy)carbonylamino)-1-(2-oxo-2-(thiophen-2-yl)ethyl)-1-azoniabicyclo[2.2.2]octane chloride |
| 30 | (R)-3-((bis(3-fluorophenyl)methoxy)carbonylamino)-1-(2-oxo-2-phenylethyl)-1-azoniabicyclo[2.2.2]octane chloride |
| 31 | (R)-3-((bis(3-fluorophenyl)methoxy)carbonylamino)-1-(2-phenoxyethyl)-1-azoniabicyclo[2.2.2]octane bromide |
| 32 | (R)-3-((bis(3-fluorophenyl)methoxy)carbonylamino)-1-(2-(2,3-dihydrobenzofuran-5-yl)ethyl)-1-azoniabicyclo[2.2.2]octane bromide |
| 33 | (R)-3-((bis(3-fluorophenyl)methoxy)carbonylamino)-1-(4-fluorophenethyl)-1-azoniabicyclo[2.2.2]octane bromide |
| 34 | (R)-3-(benzhydryloxycarbonylamino)-1-(2-oxo-2-phenylethyl)-1-azoniabicyclo[2.2.2]octane chloride |
| 35 | (R)-3-((bis(4-fluorophenyl)methoxy)carbonylamino)-1-(2-oxo-2-phenylethyl)-1-azoniabicyclo[2.2.2]octane chloride |
| 36 | (3R)-3-(((4-methoxyphenyl)(phenyl)methoxy)carbonylamino)-1-(2-oxo-2-(thiophen-2-yl)ethyl)-1-azoniabicyclo[2.2.2]octane chloride |
| 37 | (3R)-3-(((2-fluorophenyl)(4-fluorophenyl)methoxy)-carbonylamino)-1-(2-oxo-2-(thiophen-2-yl)ethyl)-1-azoniabicyclo[2.2.2]octane chloride |
| 38 | (3R)-3-(((2-fluorophenyl)(3-fluorophenyl)methoxy)-carbonylamino)-1-(2-oxo-2-(thiophen-2-yl)ethyl)-1-azoniabicyclo[2.2.2]octane chloride |
| 39 | (3R)-3-(((3,4-difluorophenyl)(phenyl)methoxy)carbonylamino)-1-(2-oxo-2-(thiophen-2-yl)ethyl)-1-azoniabicyclo[2.2.2]octane chloride |
| 40 | phenyl(4-(trifluoromethyl)phenyl)methyl (R)-quinuclidin-3-ylcarbamate |
| 41 | (3R)-1-(2-oxo-2-(thiophen-2-yl)ethyl)-3-((phenyl(4-(trifluoromethyl)phenyl)methoxy)carbonylamino)-1-azoniabicyclo[2.2.2]octane chloride |
| 42 | (2-chlorophenyl)(4-chlorophenyl)methyl (R)-quinuclidin-3-ylcarbamate |
| 43 | (3R)-3-(((2-chlorophenyl)(4-chlorophenyl)methoxy)-carbonylamino)-1-(2-oxo-2-(thiophen-2-yl)ethyl)-1-azoniabicyclo[2.2.2]octane chloride |
| 44 | (R)-thiophen-2-ylmethyl quinuclidin-3-ylcarbamate |
| 45 | (R)-1-(2-oxo-2-(thiophen-2-yl)ethyl)-3-((thiophen-2-ylmethoxy)carbonylamino)-1-azoniabicyclo[2.2.2]octane chloride |
| 46 | (R)-O-bis(3-fluorophenyl)methyl quinuclidin-3-ylcarbamothioate |
| 47 | (R)-3-((bis(3-fluorophenyl)methoxy)carbonothioylamino)-1-(2-oxo-2-(thiophen-2-yl)ethyl)-1-azoniabicyclo[2.2.2]octane chloride |
| 48 | (R)-bis(3-fluorophenyl)methyl 1-benzylpyrrolidin-3-ylcarbamate |
| 49 | (3R)-1-benzyl-3-((bis(3-fluorophenyl)methoxy)carbonylamino)-1-methylpyrrolidinium iodide |
| 50 | 3-((bis(3-fluorophenyl)methoxy)carbonyl)-1-(2-oxo-2-phenylethyl)-1-azoniabicyclo[2.2.2]octane bromide |
| 51 | 3-((bis(3-fluorophenyl)methoxy)carbonyl)-1-(2-oxo-2-(thiophen-2-yl)ethyl)-1-azoniabicyclo[2.2.2]octane chloride |
| 52 | 3-((bis(3-fluorophenyl)methoxy)carbonyl)-1-(2-(4-methoxyphenyl)-2-oxoethyl)-1-azoniabicyclo[2.2.2]octane bromide |
| 53 | 3-((bis(3-fluorophenyl)methoxy)carbonyl)-1-(2-(4-fluorophenyl)-2-oxoethyl)-1-azoniabicyclo[2.2.2]octane bromide |
| 54 | 3-((bis(3-fluorophenyl)methoxy)carbonyl)-1-(2-oxo-2-p-tolylethyl)-1-azoniabicyclo[2.2.2]octane bromide |
| 55 | 3-((bis(3-fluorophenyl)methoxy)carbonyl)-1-(2-(5-chlorothiophen-2-yl)-2-oxoethyl)-1-azoniabicyclo[2.2.2]octane bromide |
| 56 | 3-((bis(3-fluorophenyl)methoxy)carbonyl)-1-(2-(4-chlorophenyl)-2-oxoethyl)-1-azoniabicyclo[2.2.2]octane bromide |
| 57 | 3-((bis(3-fluorophenyl)methoxy)carbonyl)-1-(2-(3-fluorophenyl)-2-oxoethyl)-1-azoniabicyclo[2.2.2]octane bromide |
| 58 | 3-((bis(3-fluorophenyl)methoxy)carbonyl)-1-(2-oxopropyl)-1-azoniabicyclo[2.2.2]octane chloride |
| 59 | 3-((bis(3-fluorophenyl)methoxy)carbonyl)-1-(2-tert-butoxy-2-oxoethyl)-1-azoniabicyclo[2.2.2]octane chloride |
| 60 | 3-((bis(3-fluorophenyl)methoxy)carbonyl)-1-(2-oxo-2-(pyridin-2-yl)ethyl)-1-azoniabicyclo[2.2.2]octane 2,2,2-trifluoroacetate |
| 61 | 3-((bis(3-fluorophenyl)methoxy)carbonyl)-1-(2-(3-(ethoxycarbonyl)isoxazol-5-yl)-2-oxoethyl)-1-azoniabicyclo[2.2.2]octane bromide |
| 62 | 3-((bis(3-fluorophenyl)methoxy)carbonyl)-1-(2-(2-fluorophenyl)-2-oxoethyl)-1-azoniabicyclo[2.2.2]octane bromide |
| 63 | 3-((bis(3-fluorophenyl)methoxy)carbonyl)-1-(2-oxo-2-(thiophen-3-yl)ethyl)-1-azoniabicyclo[2.2.2]octane bromide |
| 64 | 3-((bis(3-fluorophenyl)methoxy)carbonyl)-1-(2-(4-hydroxyphenyl)-2-oxoethyl)-1-azoniabicyclo[2.2.2]octane bromide |

-continued

| Compound | Chemical name |
|---|---|
| 65 | 1-(2-(benzo[b]thiophen-5-yl)-2-oxoethyl)-3-((bis(3-fluorophenyl)methoxy)carbonyl)-1-azoniabicyclo[2.2.2]octane 2,2,2-trifluoroacetate |
| 66 | 1-benzyl-3-((bis(3-fluorophenyl)methoxy)carbonyl)-1-azoniabicyclo[2.2.2]octane bromide |
| 67 | 3-((1,2-diphenylethoxy)carbonyl)-1-(2-oxo-2-(thiophen-2-yl)ethyl)-1-azoniabicyclo[2.2.2]octane 2,2,2-trifluoroacetate |
| 68 | 3-((bis(4-chlorophenyl)methoxy)carbonyl)-1-(2-oxo-2-(thiophen-2-yl)ethyl)-1-azoniabicyclo[2.2.2]octane chloride |
| 69 | bis(4-fluorophenyl)methyl quinuclidine-3-carboxylate |
| 70 | 3-((bis(4-fluorophenyl)methoxy)carbonyl)-1-(2-oxo-2-(thiophen-2-yl)ethyl)-1-azoniabicyclo[2.2.2]octane 2,2,2-trifluoroacetate |
| 71 | benzhydryl quinuclidine-3-carboxylate |
| 72 | 3-(benzhydryloxycarbonyl)-1-(2-oxo-2-(thiophen-2-yl)ethyl)-1-azoniabicyclo[2.2.2]octane 2,2,2-trifluoroacetate |
| 73 | (4-methoxyphenyl)(phenyl)methyl quinuclidine-3-carboxylate |
| 74 | 3-(((4-methoxyphenyl)(phenyl)methoxy)carbonyl)-1-(2-oxo-2-(thiophen-2-yl)ethyl)-1-azoniabicyclo[2.2.2]octane chloride |
| 75 | (2-chlorophenyl)(4-chlorophenyl)methyl quinuclidine-3-carboxylate |
| 76 | 3-(((2-chlorophenyl)(4-chlorophenyl)methoxy)carbonyl)-1-(2-oxo-2-(thiophen-3-yl)ethyl)-1-azoniabicyclo[2.2.2]octane 2,2,2-trifluoroacetate |
| 77 | (3,4-difluorophenyl)(phenyl)methyl quinuclidine-3-carboxylate |
| 78 | 3-(((3,4-difluorophenyl)(phenyl)methoxy)carbonyl)-1-(2-oxo-2-(thiophen-2-yl)ethyl)-1-azoniabicyclo[2.2.2]octane chloride |
| 79 | 3-fluorobenzyl quinuclidine-3-carboxylate |
| 80 | 3-((3-fluorobenzyloxy)carbonyl)-1-(2-oxo-2-(thiophen-2-yl)ethyl)-1-azoniabicyclo[2.2.2]octane 2,2,2-trifluoroacetate |
| 81 | 9H-fluoren-9-yl quinuclidine-3-carboxylate |
| 82 | 3-((9H-fluoren-9-yloxy)carbonyl)-1-(2-oxo-2-(thiophen-2-yl)ethyl)-1-azoniabicyclo[2.2.2]octane 2,2,2-trifluoroacetate |
| 83 | bis(3-fluorophenyl)methyl 1-methylpiperidine-4-carboxylate |
| 84 | 4-((bis(3-fluorophenyl)methoxy)carbonyl)-1-methyl-1-(2-oxo-2-(thiophen-2-yl)ethyl)piperidinium chloride |
| 85 | 4-((bis(3-fluorophenyl)methoxy)carbonyl)-1-methyl-1-(2-oxo-2-(thiophen-3-yl)ethyl)piperidinium bromide |
| 86 | 4-((bis(3-fluorophenyl)methoxy)carbonyl)-1-methyl-1-(2-oxo-2-(thiazol-2-yl)ethyl)piperidinium bromide |
| 87 | 1,2-diphenylethyl 1-methylpiperidine-4-carboxylate |
| 88 | 4-((1,2-diphenylethoxy)carbonyl)-1-methyl-1-(2-oxo-2-phenylethyl)piperidinium bromide |
| 89 | (E)-1,2-diphenylvinyl 1-methylpiperidine-4-carboxylate |
| 90 | (1R,4R)-4-(((E)-1,2-diphenylvinyloxy)carbonyl)-1-methyl-1-(2-oxo-2-phenylethyl)piperidinium bromide |
| 91 | 3-fluorobenzyl quinuclidine-4-carboxylate |
| 92 | 4-((3-fluorobenzyloxy)carbonyl)-1-(2-oxo-2-(thiophen-2-yl)ethyl)-1-azoniabicyclo[2.2.2]octane chloride |
| 93 | S-benzyl quinuclidine-3-carbothioate |
| 94 | 3-(benzylthiocarbonyl)-1-(2-oxo-2-(thiophen-2-yl)ethyl)-1-azoniabicyclo[2.2.2]octane chloride |

Compounds of general formula (I) and (IV) may be prepared according to the following synthetic Scheme 1.

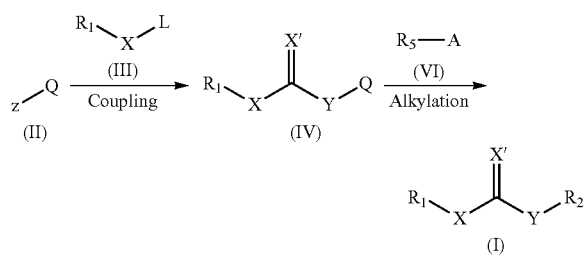

Scheme 1

Unless otherwise noted, $R_1$, $R_2$, Q, $R_5$, X, X', Y, and A are as defined above. It is well understood that protecting groups for sensitive or reactive groups are employed where necessary in accordance with general principles of chemistry. Protecting groups are manipulated according to standard methods of organic synthesis (see Green T. W. and Wuts P. G. M. (1991) *Protecting Groups in Organic Synthesis*, John Wiley et Sons, which is cincroporated herein by reference in its entirety).

General Procedure for the Preparation of Compounds of Formula (I) and (IV).

Compounds of general formula (IV), reported in the present invention, may be prepared starting from compounds of general formula (II), in which z may be either a carboxyl or an amino group and Q may be a group of general formula (f) or (g):

(f)

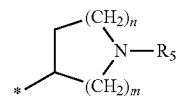

(g)

wherein m, n and $R_5$ are as described above.

These compounds (II) can be reacted with compounds of general formula (III), in which $R_1$ and X are as described above and L can be H or an alkaline or alkaline earth metal (i.e. potassium, lithium, sodium, calcium and so on).

Starting materials of general formula (II) and (III) are commercially available or may be conveniently prepared according to standard procedures extensively reported in literature.

When z is a carboxyl group, the coupling between compounds of general formula (II) and (III) may be promoted using standard amidation and peptide coupling conditions. The operative conditions are chosen on the basis of the reactivity of the acid (II) over alcohol/thioalcohol (III) and of the compatibility of other groups being present in both compounds (for a general reference on the above reaction and operative conditions thereof see, for instance, Carey, F. A. and Sundeberg, R. J. Advanced Organic Chemistry, Third Edition (1990), Plenum Press, New York and London, pg 145), which is incorporated herein by reference in its entirety.

The said conditions include, for instance, activating acid (II) by means of one or more equivalents of a commercially available condensing agent such as a carbodiimide (e.g. 1-ethyl-3-(3-dimethylaminopropyl)carbodiimide (EDC) and the like) for example in the presence of N-hydroxybenzotriazole (HOBt) followed by reaction of the activated intermediate with alcohol or thioalcohol (III). An organic base such as triethylamine and the like may be also present in the reaction mixture. The activated intermediate may be either isolated, or pre-formed or generated in situ, and then properly reacted with compounds of formula (III). Suitable solvents for the coupling reaction include, but are not limited to, halocarbon solvents (e.g. dichloromethane (DCM)), tetrahydrofuran (THF), dioxane, dimethylformamide (DMF), and acetonitrile. The reaction proceeds at temperature ranging from about 0° C. up to about 170° C., for a time period in the range of about 1 hour up to about 96 hours. The reaction may be carried out under conventional heating (using an oil bath) or under microwave irradiation. The reaction may be conducted either in an open vessel or in a sealed tube.

In some embodiments of the invention, acid (II) can be most conveniently activated as acyl halide such as acyl chloride (z=COCl). This activation may be affected according to one of the several standard procedures reported in the literature. They comprise, for instance, treatment of acid (II) with one or more equivalents of oxalyl chloride or thionyl chloride. This reaction may be conducted in the presence of a catalytic amount of dimethylformamide (DMF) in a suitable solvent (e.g. dichloromethane) or neat, at temperature ranging from about 0° C. to about 120° C. The activated intermediate may be either isolated, or pre-formed or generated in situ. This intermediate can then be reacted with alcohol or thioalcohol (III), using known methods in order to obtain compounds of formula (IV). The reaction may be promoted by a base such as triethylamine, pyridine and 4-dimethylaminopyridine, and carried out in a suitable solvent (e.g. dichloromethane) or neat. This reaction is performed in a temperature range from about 0° C. to about 140° C. over a period of about 1 hour to about 74 hours. The reaction may be conducted under conventional heating (using an oil bath) or under microwave heating. The reaction may be carried out in an open vessel or in a sealed tube.

The resulting esters (X, X'=O) and thioesters (X=S; X'=O) of general formula (IV) can be then alkylated to obtain compounds of general formula (I). Alternatively, they can be first transformed into the corresponding thienoester (X=O; X'=S) or di-thioester (X, X'=S) of general formula (IV). This conversion can be effected according to one of the known standard procedures. For instance, esters (IV) can be treated with Lawessons's reagent (see Nicolaou, K. C. et al., Journal of the American Chemical Society, 1990, 12/17, pp. 6263-6276, which is incorporated herein by reference in its entirety) or with tetraphosphorus decasulfide (see Cho, D. et al., Tetrahedron, 2010, 66/30, pp. 5583-5588, which is incorporated herein by reference in its entirety) to achieve the corresponding thienoester (IV). Likewise, thioesters may be converted into di-thioester by treatment with Lawessons's reagent (see Cohen, O. et al., Tetrahedron, 2010, 66/20, pp. 3579-3582, which is incorporated herein by reference in its entirety). The resulting thienoester (X=O; X'=S) or di-thioester (X, X'=S) of general formula (IV) can then be alkylated to obtain compounds of general formula (I).

When z is an amino group, compound of general formula (II) may be coupled with compound of general formula (III) to afford carbamate, thiocarbamate or dithiocarbamate of general formula (IV). This coupling may be effected according to one of the standard procedures broadly reported in the literature (a survey of the suitable reactions is given by Chaturvedi, D. Current Organic Synthesis, 2007, 3, 308 or by Smith, M. B. and March, J., March's Advanced Organic Chemistry, Fifth Edition (2001), John Wiley & Sons, Inc., New York, appendix B, 1660, both of which are incorporated herein by reference in their entireties). For instance, the amine (II) could be treated with suitable activating reagent that could be selected from, but are not limited to, 1,1'-carbonyldiimidazole, 1,1'-thiocarbonyldiimidazole, diphosgene, triphosgene, or p-nitrophenylchloroformate. The reaction may be promoted by a base selected from the group consisting of triethylamine, pyridine, 4-dimethylaminopyridine, and the like, in a suitable solvent (e.g. dimethylformamide (DMF), tetrahydrofuran (THF), dichloromethane (DCM)). The activated intermediate is generally pre-formed but it may be either generated in situ or isolated. Then, the activated amine is reacted with an alcohol or thioalcohol of formula (III), most conveniently dissolved in the same solvent used for the activation of compound (II). Preferably, the alcohol or thioalcohol is preliminary treated with a base advantageously selected from NaH, BuLi (butyl lithium), and lithium diisopropylamide (LDA).

The compounds of general formula (IV) wherein Q is a group of formula (f) or (g), are eventually alkylated with an agent of general formula (VI) to give compounds of general formula (I), wherein $R_2$ is a group with the above described meanings.

This kind of reaction is largely described in literature under several different conditions. For instance, the reaction may be performed neat or in a suitable solvent selected from the group consisting of acetonitrile, ethyl acetate, DMF and tetrahydrofuran. The reaction typically proceeds at temperature range from about 0° C. up to about 170° C., for a time in the range of few minutes up to about 72 hours. The reaction may be carried out under conventional heating (using an oil bath) or under microwave irradiation. The reaction may be conducted either in an open vessel or in a sealed tube.

Compounds of general formula (I) can be either considered as final products or can be further reacted to prepare other compounds of general formula (I). Thus, any suitable moiety of $R_1$ or $R_2$ group in general formula (I) could undergo a variety of reactions, to afford other final compounds of general formula (I).

Likewise, the optional salification of the compounds of formula (I) may be carried out by properly converting any of the free acidic groups (e.g. carboxylic) or free amino groups into the corresponding pharmaceutically acceptable salts.

In this case too, the operative conditions used for the optional salification of the compounds of the invention are conventional Further, depending from any of the meanings provided to $R_1$ and $R_2$, among those reported above, it will be clear to the skilled person that asymmetric centers may be present within the compounds of formula (I). Therefore, the invention also includes any of the optical stereoisomers, diastereoisomers, and mixtures thereof, in any proportion.

The present invention also provides pharmaceutical compositions of compounds of formula (I) in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally, and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges, and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates, and polyethylene glycols.

Formulations for vaginal administration can be in the form of cream, gel, paste, foam, or spray formula containing, in addition to the active ingredient, such as suitable carriers, are also known.

For topical administration, the pharmaceutical composition can be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols, or propellant-free inhalable formulations.

For administration as a dry powder, known single- or multi-dose inhalers may be utilized. In that case the powder may be filled in gelatine, plastic, or other capsules, cartridges or blister packs or in a reservoir.

A diluent or carrier, generally non-toxic and chemically inert to the compounds of present the invention, e.g. lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers, and optionally other excipients.

The propellant-free inhalable formulations comprising the compounds of the present invention may be in form of solutions or suspensions in an aqueous, alcoholic, or hydroalcoholic medium, and they may be delivered by known jet or ultrasonic nebulizers or by soft-mist nebulizers such as Respimat®.

The compounds of the present invention may be administered as the sole active agent or in combination with one or more other pharmaceutical active ingredients including those currently used in the treatment of respiratory disorders, e.g. $beta_2$-agonists, corticosteroids and anticholinergic or antimuscarinic agents.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

The compounds of formula (I) may be administered for the prevention and/or treatment of broncho-obstructive or inflammatory diseases, such as asthma, chronic bronchitis, chronic obstructive pulmonary disease (COPD), bronchial hyperreactivity, cough, emphysema, or rhinitis; urological disorders such as urinary incontinence, pollakiuria, cystospasm, chronic cystitis, and overactive bladder (OAB); gastrointestinal disorders such as bowel syndrome, spastic colitis, diverticulitis, peptic ulceration, gastrointestinal motility, or gastric acid secretion; dry mouth; mydriasis, tachycardia; and ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

Unless otherwise noted, all starting materials were obtained from commercial suppliers and used without any further purification; all reactions are conducted under an inert atmosphere and in dry solvents.

Example 1

Preparation of (R)-bis(3-fluorophenyl)methyl quinuclidin-3-ylcarbamate (Compound 1)

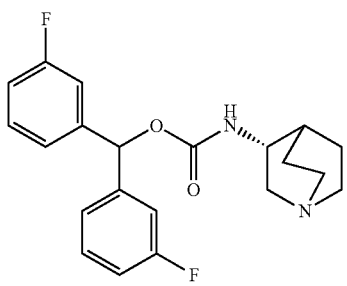

In a first flask, (R)-quinuclidin-3-amine dihydrochloride (500 mg, 2.51 mmol) was dissolved in MeOH (25 ml) and water (2.50 ml). Sodium bicarbonate (211 mg, 2.51 mmol) was added, and the reaction was stirred at room temperature for 1 hour. The reaction was then evaporated to dryness. The residue was dissolved in dry DMF (25.0 ml), and CDI (407 mg, 2.51 mmol) was added. The reaction was stirred at room temperature for 16 hours.

In a second flask, bis(3-fluorophenyl)methanol (1.11 g, 5.02 mmol) was dissolved in dry DMF (25 ml) and treated portionwise with sodium hydride (60% dispersion in mineral oil, 201 mg, 5.02 mmol) at 0° C. This second reaction was stirred at room temperature for 30 minutes and then poured into the first flask.

The resulting reaction was stirred at room temperature for 2 days. Then the reaction was portioned between $Et_2O$ and water. The organic phase was dried over $Na_2SO_4$, filtered and evaporated to dryness. The crude was purified by flash chromatography (DCM/MeOH=9/1 to DCM/MeOH=75/25+0.5% TEA) to obtain (R)-bis(3-fluorophenyl)methyl quinuclidin-3-ylcarbamate (419 mg).

$^1$H NMR (300 MHz, DMSO-$d_6$) δ ppm 7.63 (d, 1H), 7.35-7.49 (m, 2H), 7.19-7.32 (m, 4H), 7.04-7.18 (m, 2H), 6.68 (s, 1H), 3.42-3.58 (m, 1H), 2.93-3.15 (m, 1H), 2.71-2.85 (m, 1H), 2.55-2.70 (m, 3H), 2.41-2.47 (m, 1H), 1.65-1.83 (m, 2H), 1.36-1.64 (m, 2H), 1.09-1.35 (m, 1H).

Example 2

Preparation of (R)-benzhydryl quinuclidin-3-ylcarbamate (Compound 2)

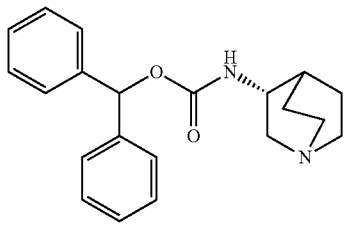 [SMILES: O=C(N[C@H]1CN2CCC1CC2)OC(c1ccccc1)c1ccccc1]

In a first flask, (R)-quinuclidin-3-amine dihydrochloride (0.10 g, 0.50 mmol) was dissolved in MeOH (5 ml) and water (0.5 ml). Sodium bicarbonate (84.0 mg, 1.00 mmol) was added, and the reaction was stirred at room temperature for 1 hour. The reaction was then evaporated to dryness. The solid was dissolved in dry DMF (5 ml), and CDI (81.0 mg, 0.50 mmol) was added. The reaction was stirred at room temperature for 7 hours.

In a second flask, diphenylmethanol (0.18 g, 1.00 mmol) was dissolved in dry DMF (5 ml) and treated portionwise with NaH (40.0 mg, 1.00 mmol) at 0° C. The reaction was stirred at room temperature for 20 minutes and then poured into the first flask.

The resulting reaction was stirred at room temperature overnight. The reaction mixture was portioned between $Et_2O$ and water. The organic phase was washed with brine, dried over $Na_2SO_4$, filtered, and evaporated to dryness. The crude was purified by flash chromatography (DCM/MeOH=9/1 to DCM/MeOH=75/25+0.5% TEA) to obtain (R)-benzhydryl quinuclidin-3-ylcarbamate (105 mg).

$^1$H NMR (300 MHz, DMSO-d6) δ ppm 7.57 (d, 1H) 7.18-7.46 (m, 10H) 6.66 (s, 1H) 3.40-3.59 (m, 1H) 2.96-3.13 (m, 1H) 2.56-2.89 (m, 4H) 2.40-2.48 (m, 1H) 1.67-1.81 (m, 2H) 1.37-1.64 (m, 2H) 1.12-1.35 (m, 1H).

Example 3

Preparation of (R)-bis(4-fluorophenyl)methyl quinuclidin-3-ylcarbamate (Compound 3)

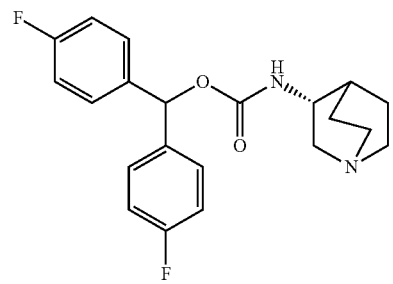 [SMILES: O=C(N[C@H]1CN2CCC1CC2)OC(c1ccc(F)cc1)c1ccc(F)cc1]

In a first flask, (R)-quinuclidin-3-amine dihydrochloride (50.0 mg, 0.25 mmol) was dissolved in MeOH (2.5 ml) and water (0.25 ml). Sodium bicarbonate (42.0 mg, 0.50 mmol) was added, and the reaction was stirred at room temperature for 1 hour. The reaction was then evaporated to dryness. The solid was dissolved in dry DMF (2.50 ml), and CDI (40.5 mg, 0.25 mmol) was added. The reaction was stirred at room temperature for 7 hours.

In a second flask, bis(4-fluorophenyl)methanol (111 mg, 0.50 mmol) was dissolved in dry DMF (5 ml), and sodium hydride (20.0 mg, 0.50 mmol) was added portionwise at 0° C. The reaction was stirred at 0° C. for 5 minutes and then poured into the first flask, cooled at 0° C.

The resulting reaction mixture was stirred at room temperature overnight. The reaction mixture was then portioned between $Et_2O$ and water. The organic phase was dried over $Na_2SO_4$, filtered, and evaporated to dryness. The crude was purified by flash chromatography (DCM/MeOH=9/1 to DCM/MeOH=75/25+0.5% TEA) to obtain (R)-bis(4-fluorophenyl)methyl quinuclidin-3-ylcarbamate (37.0 mg).

$^1$H NMR (300 MHz, DMSO-d6) δ ppm 7.60 (d, 1H) 7.40 (dd, 4H) 7.03-7.30 (m, 4H) 6.68 (s, 1H) 3.37-3.60 (m, 1H) 2.95-3.16 (m, 1H) 2.74-2.89 (m, 1H) 2.55-2.70 (m, 3H) 2.45 (d, 1H) 1.65-1.84 (m, 2H) 1.36-1.64 (m, 2H) 1.21-1.36 (m, 1H).

The following compounds were prepared following the route described in Example 3, using the suitable alcohols instead of bis(4-fluorophenyl)methanol. These compounds were achieved as a mixture of diastereoisomers.

TABLE 1

| Compound | Structure | ¹H-NMR |
|---|---|---|
| 4 | 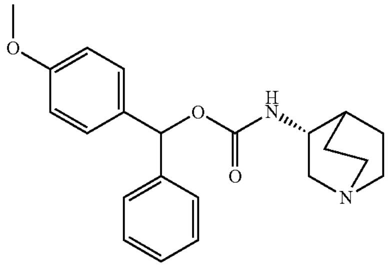 [SMILES: COc1ccc(C(OC(=O)N[C@H]2CN3CCC2CC3)c2ccccc2)cc1] | (300 MHz, DMSO-d$_6$) δ ppm 7.52 (d, 1 H) 7.16-7.40 (m, 7 H) 6.85-6.95 (m, 2 H) 6.62 (s, 1 H) 3.73 (s, 3 H) 3.40-3.55 (m, 1 H) 2.92-3.11 (m, 1 H) 2.69-2.83 (m, 1 H) 2.55-2.68 (m, 3 H) 2.37-2.47 (m, 1 H) 1.09-2.18 (m, 5 H) |
| 5 | 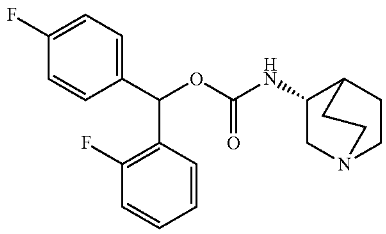 [SMILES: O=C(N[C@H]1CN2CCC1CC2)OC(c1ccc(F)cc1)c1ccccc1F] | (300 MHz, DMSO-d6) δ ppm 7.63 (d, J = 7.04 Hz, 1 H) 7.31-7.57 (m, 4 H) 7.10-7.31 (m, 4 H) 6.85 (s, 1 H) 3.34-3.60 (m, 1 H) 2.90-3.12 (m, 1 H) 2.69-2.85 (m, 2 H) 2.55-2.69 (m, 2 H) 1.81-2.25 (m, 1 H) 1.61-1.81 (m, 2 H) 1.35-1.61 (m, 2 H) 1.13-1.35 (m, 1 H) |
| 6 | 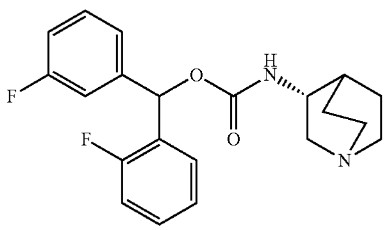 [SMILES: O=C(N[C@H]1CN2CCC1CC2)OC(c1cccc(F)c1)c1ccccc1F] | (300 MHz, DMSO-d6) δ ppm 7.66 (d, 1 H) 7.31-7.54 (m, 2 H) 7.00-7.31 (m, 6 H) 6.86 (s, 1 H) 3.39-3.63 (m, 1 H) 3.03 (t, 1 H) 2.68-2.86 (m, 2 H) 2.62 (d, 3 H) 2.40-2.48 (m, 1 H) 1.65-1.84 (m, 2 H) 1.36-1.65 (m, 1 H) 1.08-1.36 (m, 1 H) |
| 7 | 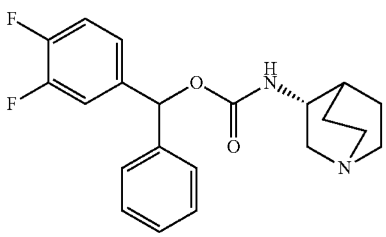 [SMILES: O=C(N[C@H]1CN2CCC1CC2)OC(c1ccccc1)c1ccc(F)c(F)c1] | (300 MHz, DMSO-d6) δ ppm 7.60 (d, 1 H) 7.17-7.52 (m, 8 H) 6.66 (s, 1 H) 3.35-3.57 (m, 1 H) 2.94-3.12 (m, 1 H) 2.70-2.85 (m, 1 H) 2.57-2.69 (m, 3 H) 2.43 (d, 1 H) 1.64-1.86 (m, 2 H) 1.34-1.64 (m, 2 H) 1.14-1.34 (m, 1 H) |

Example 4

Preparation of bis(3-fluorophenyl)methyl quinuclidine-3-carboxylate (Compound 8)

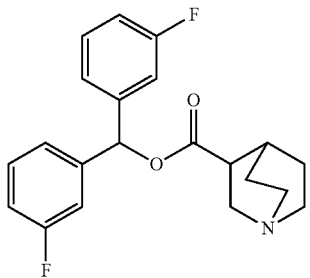 [SMILES: O=C(OC(c1cccc(F)c1)c1cccc(F)c1)C1CN2CCC1CC2]

Quinuclidine-3-carboxylic acid hydrochloride (817 mg, 4.26 mmol), EDC (1.23 g, 6.39 mmol), and HOBT (979 mg, 6.39 mmol) were dissolved in dry DMF (40 ml). DIPEA (2.61 ml, 14.9 mmol) and bis(3-fluorophenyl)methanol (1.03 mg, 4.69 mmol) were added, and the mixture was stirred at room temperature overnight. The mixture was diluted with water and extracted several times with Et$_2$O. The organic phases were collected and washed with brine, dried (Na$_2$SO$_4$), filtered, and evaporated. The residue was purified by flash chromatography (DCM/MeOH=9/1) to obtain bis(3-fluorophenyl)methyl quinuclidine-3-carboxylate (874 mg, racemic mixture).

¹H NMR (300 MHz, DMSO-d6) δ ppm 7.42 (td, 2H), 7.22-7.34 (m, 4H), 7.05-7.19 (m, 2H), 6.85 (s, 1H), 2.99-3.12 (m, 1H), 2.86-2.99 (m, 1H), 2.59-2.83 (m, 5H), 2.13-2.24 (m, 1H), 1.41-1.72 (m, 2H), 1.15-1.40 (m, 2H).

Example 5

Preparation of 1,2-diphenylethyl quinuclidine-3-carboxylate (Compound 9)

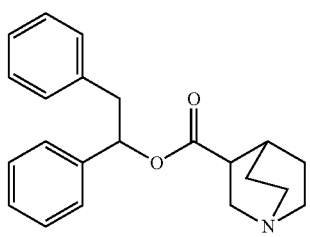 [SMILES: O=C(OC(Cc1ccccc1)c1ccccc1)C1CN2CCC1CC2]

Quinuclidine-3-carboxylic acid hydrochloride (160 mg, 0.83 mmol), EDC (290 mg, 1.51 mmol), and HOBT (232 mg, 1.51 mmol) were dissolved in dry DMF (8 ml). 1,2-Diphenylethanol (150 mg, 0.76 mmol) and TEA (0.32 ml, 2.27 mmol) were added, and the resulting mixture was stirred at room temperature overnight. Then quinuclidine-3-carboxylic acid hydrochloride (72.5 mg, 0.38 mmol), EDC (87 mg, 0.45 mmol), and HOBT (57.9 mg, 0.38 mmol) were added followed by TEA (0.16 ml, 1.13 mmol), and the mixture was stirred for additional 32 hours. The mixture was diluted with water and extracted three times with Et$_2$O. The organic phases were collected, washed with brine, dried over Na$_2$SO$_4$, filtered, and evaporated to dryness. The crude residue was purified by flash chromatography (DCM/MeOH=9/1) to obtain 1,2-diphenylethyl quinuclidine-3-carboxylate (136 mg, racemic mixture).

$^1$H NMR (300 MHz, DMSO-d6) δ ppm 6.83-7.61 (m, 10H), 5.68-6.17 (m, 1H), 3.01-3.25 (m, 2H), 2.54-2.98 (m, 7H), 1.76-1.90 (m, 1H), 1.32-1.64 (m, 2H), 0.80-1.22 (m, 2H).

Example 6

Preparation of bis(4-chlorophenyl)methyl quinuclidine-3-carboxylate (Compound 10)

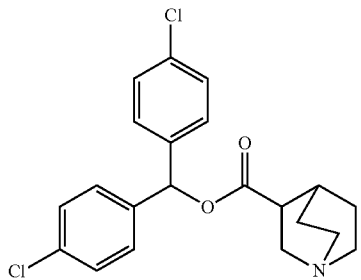 [SMILES: O=C(OC(c1ccc(Cl)cc1)c1ccc(Cl)cc1)C1CN2CCC1CC2]

Quinuclidine-3-carboxylic acid hydrochloride (150 mg, 0.78 mmol), EDC (225 mg, 1.17 mmol) and HOBT (180 mg, 1.17 mmol) were dissolved in dry THF (7.5 ml). Bis(4-chlorophenyl)methanol (218 mg, 0.86 mmol) was added followed by TEA (382 μl, 2.74 mmol). The resulting reaction was stirred at room temperature overnight. THF was removed under vacuum, and the crude was partitioned between EtOAc and water. The organic phase was washed with sat. NaHCO$_3$, dried over sodium sulphate, filtered, and evaporated to dryness. The crude was purified by flash chromatography (EtOAc/MeOH=8/2 to 7:3+1% of NH$_4$OH) to obtain bis(4-chlorophenyl)methyl quinuclidine-3-carboxylate (85.0 mg, racemic mixture).

$^1$H NMR (300 MHz, DMSO-d6) δ ppm 7.30-7.54 (m, 8H) 6.89 (s, 1H) 3.33-3.55 (m, 2H) 2.94-3.26 (m, 5H) 2.54-2.65 (m, 1H) 1.78-2.10 (m, 2H) 1.59-1.78 (m, 1H) 1.31-1.55 (m, 1H).

Example 7

Preparation of (R)-3-((bis(3-fluorophenyl)methoxy) carbonylamino)-1-(2-oxo-2-(thiophen-3-yl)ethyl)-1-azoniabicyclo[2.2.2]octane bromide (Compound 11)

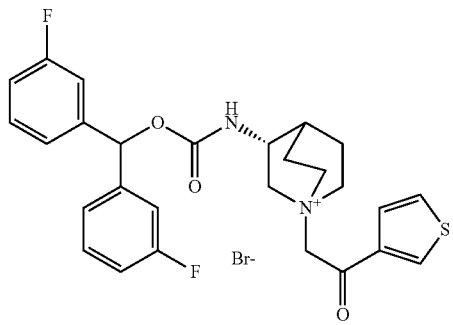 [SMILES: O=C(N[C@H]1C[N+]2(CC(=O)c3ccsc3)CCC1CC2)OC(c1cccc(F)c1)c1cccc(F)c1 ; [Br-]]

2-Bromo-1-(thiophen-3-yl)ethanone (27.5 mg, 0.13 mmol) was added to a solution of (R)-bis(3-fluorophenyl) methyl quinuclidin-3-ylcarbamate (50 mg, 0.13 mmol, prepared as in example 1) in ethyl acetate (2 ml). The reaction was stirred at room temperature overnight. Et$_2$O (2 ml) was added, and the precipitate was collected by suction filtration and dried under vacuum at 40° C. over a week-end to obtain (R)-3-((bis(3-fluorophenyl)methoxy)-carbonylamino)-1-(2-oxo-2-(thiophen-3-yl)ethyl)-1-azoniabicyclo[2.2.2]-octane bromide (66.3 mg).

$^1$H NMR (300 MHz, DMSO-d$_6$) δ ppm 8.63 (dd, 1H) 8.09-8.25 (m, 1H) 7.74 (dd, 1H) 7.51-7.62 (m, 1H) 7.35-7.50 (m, 2H) 7.20-7.35 (m, 4H) 7.07-7.20 (m, 2H) 6.73 (s, 1H) 4.97 (dd, 2H) 3.92-4.25 (m, 2H) 3.46-3.83 (m, 5H) 1.81-2.25 (m, 5H);

LC-MS (ESI POS): 496.99 (M+).

The following compounds were prepared following the route described in Example 7, using the suitable alkylating agents instead of 2-bromo-1-(thiophen-3-yl)ethanone.

TABLE 2

| Compound | Structure | $^1$H-NMR | [M$^+$] |
|---|---|---|---|
| 12 | (structure shown) | (300 MHz, DMSO-d$_6$) δ ppm 8.19 (d, 1 H), 7.94-8.04 (m, 2 H), 7.63-7.75 (m, 2 H), 7.43 (td, 2 H), 7.19-7.36 (m, 4 H), 7.07-7.21 (m, 2 H), 6.73 (s, 1 H), 4.92-5.24 (m, 1 H), 3.89-4.17 (m, 2 H), 3.45-3.89 (m, 5 H), 2.17-2.26 (m, 1 H), 2.10-2.16 (m, 1 H), 1.97-2.10 (m, 2 H), 1.79-1.96 (m, 1 H) | 525.18 |

TABLE 2-continued
| Compound | Structure | ¹H-NMR | [M⁺] |
|---|---|---|---|
| 13 | 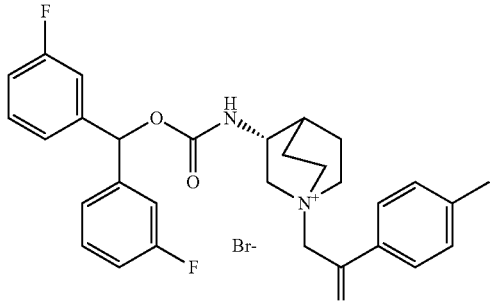 | (300 MHz, DMSO-d6) δ ppm 8.18 (d, 1 H), 7.76-8.00 (m, 2 H), 7.35-7.52 (m, 4 H), 7.22-7.34 (m, 4 H), 7.00-7.21 (m, 2 H), 6.73 (s, 1 H), 4.87-5.18 (m, 1 H), 3.90-4.23 (m, 2 H), 3.45-3.85 (m, 5 H), 2.41 (s, 3 H), 2.17-2.25 (m, 1 H), 2.10-2.17 (m, 1 H), 1.97-2.10 (m, 2 H), 1.81-1.97 (m, 1 H) | 505.20 |
| 14 | 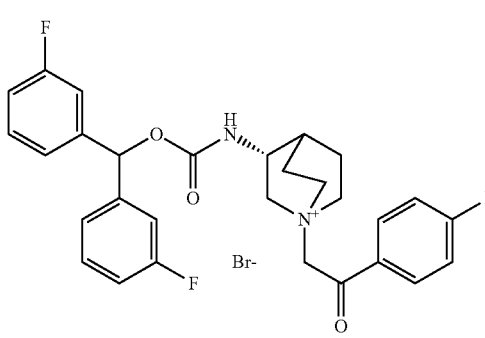 | (300 MHz, DMSO-d6) δ ppm 8.19 (d, 1 H), 7.98-8.14 (m, 2 H), 7.36-7.58 (m, 4 H), 7.19-7.36 (m, 4 H), 7.08-7.19 (m, 2 H), 6.73 (s, 1 H), 4.90-5.23 (m, 1 H), 3.89-4.18 (m, 2 H), 3.45-3.88 (m, 5 H), 2.16-2.26 (m, 1 H), 2.10-2.16 (m, 1 H), 1.98-2.09 (m, 2 H), 1.81-1.98 (m, 1 H) | 509.22 |
| 15 | 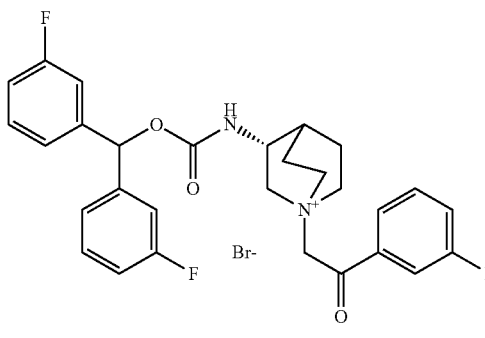 | (300 MHz, DMSO-d6) δ ppm 8.19 (d, 1 H), 7.76-7.86 (m, 2 H), 7.55-7.74 (m, 2 H), 7.37-7.51 (m, 2 H), 7.25 (br. s., 4 H), 7.06-7.20 (m, 2 H), 6.73 (s, 1 H), 4.89-5.32 (m, 1 H), 3.87-4.28 (m, 2 H), 3.42-3.86 (m, 5 H), 2.19-2.32 (m, 1 H), 2.10-2.19 (m, 1 H), 1.96-2.10 (m, 2 H), 1.71-1.96 (m, 1 H) | 509.22 |
| 16 | 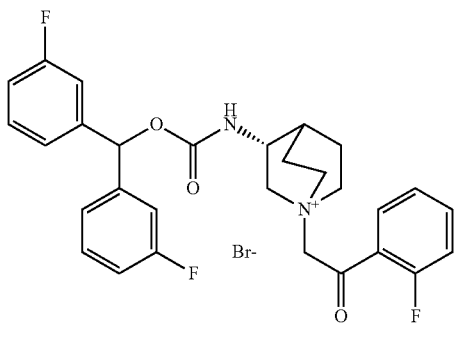 [SMILES: O=C(N[C@H]1C[N+]2(CC(=O)c3ccccc3F)CCC1CC2)OC(c1cccc(F)c1)c1cccc(F)c1 ; [Br-]] | (300 MHz, DMSO-d6) δ ppm 8.17 (br. s., 1 H), 7.95 (td, 1 H), 7.71-7.85 (m, 1 H), 7.38-7.52 (m, 4 H), 7.20-7.37 (m, 4 H), 7.08-7.19 (m, 2 H), 6.73 (s, 1 H), 4.81-5.01 (m, 1 H), 3.92-4.18 (m, 2 H), 3.45-3.83 (m, 5 H), 2.18-2.25 (m, 1 H), 2.09-2.17 (m, 1 H), 1.97-2.08 (m, 2 H), 1.80-1.97 (m, 1 H) | 509.22 |

TABLE 2-continued
| Compound | Structure | ¹H-NMR | [M⁺] |
|---|---|---|---|
| 17 | 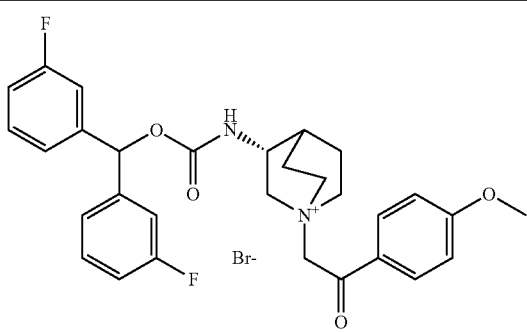 | (300 MHz, DMSO-d6) δ ppm 8.18 (d, 1 H), 7.85-8.03 (m, 2 H), 7.35-7.58 (m, 2 H), 7.25 (br. s., 4 H), 7.01-7.20 (m, 4 H), 6.73 (s, 1 H), 4.84-5.13 (m, 1 H), 3.92-4.17 (m, 2 H), 3.88 (s, 3 H), 3.43-3.82 (m, 5 H), 2.20 (br. s., 1 H), 2.10-2.17 (m, 1 H), 1.96-2.09 (m, 2 H), 1.81-1.96 (m, 1 H) | 521.23 |
| 18 | 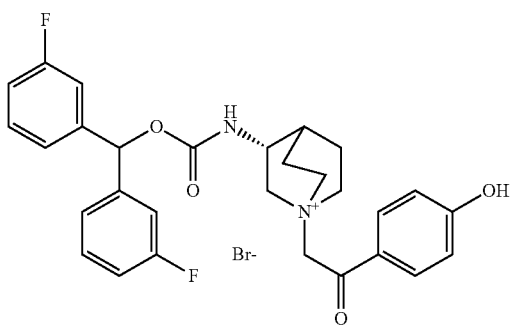 [SMILES: O=C(N[C@H]1C[N+]2(CC(=O)c3ccc(O)cc3)CCC1CC2)OC(c1cccc(F)c1)c1cccc(F)c1 ; [Br-]] | (300 MHz, DMSO-d6) δ ppm 10.74 (br. s., 1 H), 8.17 (d, 1 H), 7.79-7.90 (m, 2 H), 7.43 (td, 2 H), 7.21-7.31 (m, 4 H), 7.08-7.20 (m, 2 H), 6.85-6.94 (m, 2 H), 6.73 (s, 1 H), 4.98 (s, 2 H), 3.91-4.28 (m, 2 H), 3.45-3.91 (m, 5 H), 1.78-2.39 (m, 5 H) | 507.32 |
| 19 | 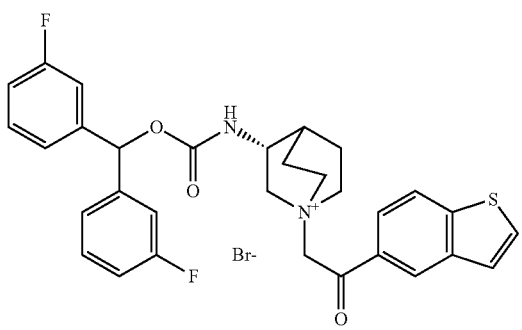 [SMILES: O=C(N[C@H]1C[N+]2(CC(=O)c3ccc4sccc4c3)CCC1CC2)OC(c1cccc(F)c1)c1cccc(F)c1 ; [Br-]] | (300 MHz, DMSO-d6) δ ppm 8.58 (d, 1 H) 8.24 (d, 1 H) 8.17-8.22 (m, 1 H) 7.97 (d, 1 H) 7.92 (dd, 1 H) 7.66 (d, 1 H) 7.36-7.52 (m, 2 H) 7.27 (d, 4 H) 7.05-7.21 (m, 2 H) 6.74 (s, 1 H) 5.22 (d, 2 H) 3.93-4.23 (m, 2 H) 3.45-3.91 (m, 5 H) 2.06 (m, 5 H) | 547.05 |
| 20 | 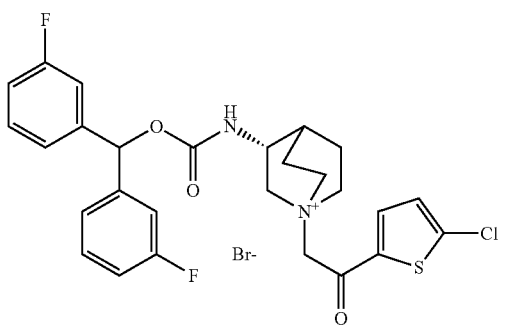 [SMILES: O=C(N[C@H]1C[N+]2(CC(=O)c3ccc(Cl)s3)CCC1CC2)OC(c1cccc(F)c1)c1cccc(F)c1 ; [Br-]] | (300 MHz, DMSO-d6) δ ppm 8.07-8.25 (m, 1 H) 8.00 (d, 1 H) 7.43 (d, 1 H) 7.37-7.49 (m, 2 H) 7.26 (d, 4 H) 7.05-7.19 (m, 2 H) 6.73 (s, 1 H) 4.94 (s, 1 H) 3.91-4.16 (m, 2 H) 3.40-3.79 (m, 5 H) 1.79-2.25 (m, 5 H) | 531.12 |

TABLE 2-continued

| Compound | Structure | ¹H-NMR | [M⁺] |
|---|---|---|---|
| 21 | 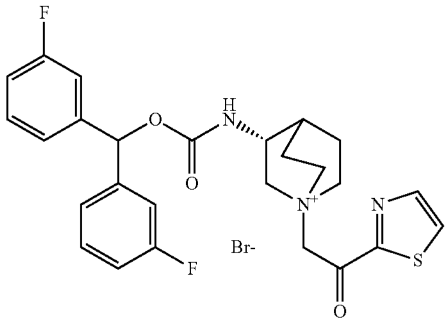 [SMILES: O=C(N[C@H]1C[N+]2(CC(=O)c3nccs3)CCC1CC2)OC(c1cccc(F)c1)c1cccc(F)c1 ; [Br-]] | (300 MHz, DMSO-d6) δ ppm 8.38 (d, 1 H) 8.24 (d, 1 H) 8.11-8.21 (m, 1 H) 7.37-7.50 (m, 2 H) 7.26 (d, 4 H) 7.04-7.21 (m, 2 H) 6.73 (s, 1 H) 5.07-5.27 (m, 2 H) 3.94-4.21 (m, 1 H) 3.49-3.90 (m, 5 H) 2.95-3.19 (m, 1 H) 2.10-2.26 (m, 2H) 1.78-2.10 (m, 3 H) | 498.14 |
| 22 | 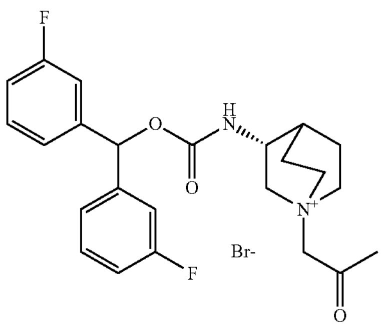 [SMILES: CC(=O)C[N+]12CCC(CC1)[C@@H](NC(=O)OC(c1cccc(F)c1)c1cccc(F)c1)C2 ; [Br-]] | (300 MHz, DMSO-d6) δ ppm 8.15 (d, 1 H), 7.36-7.50 (m, 2 H), 7.21-7.33 (m, 4 H), 7.07-7.20 (m, 2 H), 6.72 (s, 1 H), 4.42 (s, 2 H), 3.96-4.12 (m, 1 H), 3.81-3.96 (m, 1 H), 3.35-3.73 (m, 5 H), 2.14 (s, 3 H), 2.06-2.23 (m, 2 H), 1.92-2.03 (m, 2 H), 1.74-1.91 (m, 1 H) | 429.06 |
| 23 | 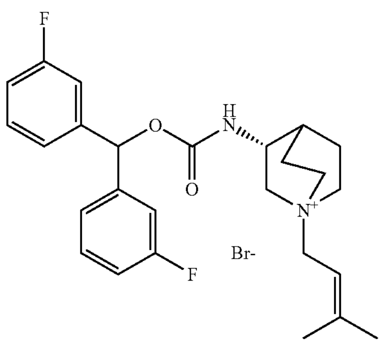 [SMILES: CC(C)=CC[N+]12CCC(CC1)[C@@H](NC(=O)OC(c1cccc(F)c1)c1cccc(F)c1)C2 ; [Br-]] | (300 MHz, DMSO-d6) δ ppm 7.87-8.18 (m, 1 H), 7.34-7.56 (m, 2 H), 7.20-7.34 (m, 4 H), 7.14 (t, 2 H), 6.73 (s, 1 H), 5.32 (t, 1 H), 3.88-4.11 (m, 1 H), 3.55-3.88 (m, 1 H), 3.77 (d, 2 H), 3.30-3.43 (m, 4 H), 2.97-3.16 (m, 1 H), 1.86-2.19 (m, 4 H), 1.82 (s, 3 H), 1.66-1.86 (m, 1 H), 1.73 (s, 3 H) | 441.32 |
| 24 | 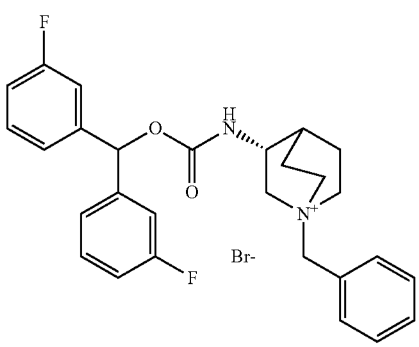 [SMILES: O=C(N[C@H]1C[N+]2(Cc3ccccc3)CCC1CC2)OC(c1cccc(F)c1)c1cccc(F)c1 ; [Br-]] | (300 MHz, DMSO-d6) δ ppm 8.01 (d, 1 H), 7.33-7.68 (m, 7 H), 6.96-7.33 (m, 6 H), 6.71 (s, 1 H), 4.42 (s, 2 H), 3.90-4.12 (m, 1 H), 3.79 (t, 1 H), 3.32-3.53 (m, 4 H), 2.95-3.20 (m, 1 H), 2.01-2.20 (m, 2 H), 1.74-2.01 (m, 3 H) | 463.33 |

TABLE 2-continued

| Compound | Structure | ¹H-NMR | [M⁺] |
|---|---|---|---|
| 25 | 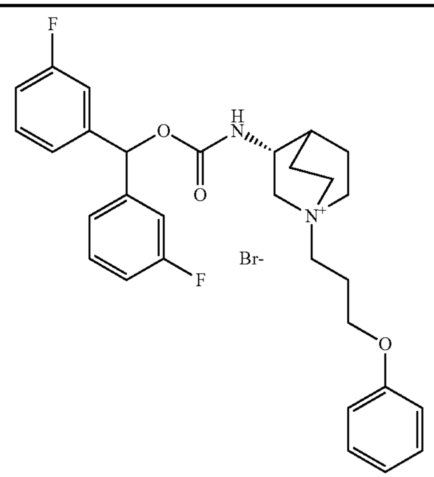 | (300 MHz, DMSO-d6) δ ppm 8.04 (d, 1 H), 7.37-7.49 (m, 2 H), 7.20-7.36 (m, 6 H), 7.07-7.20 (m, 2 H), 6.89-7.01 (m, 3 H), 6.73 (s, 1 H), 4.01-4.09 (m, 2 H), 3.93-4.01 (m, 1 H), 3.70-3.87 (m, 1 H), 3.32-3.55 (m, 6 H), 3.05-3.23 (m, 1 H), 1.62-2.42 (m, 7 H) | 507.36 |

Example 8

Preparation of (R)-3-((bis(3-fluorophenyl)methoxy)carbonylamino)-1-(2-(5-cyanothiophen-2-yl)-2-oxo-ethyl)-1-azoniabicyclo[2.2.2]octane bromide (Compound 26)

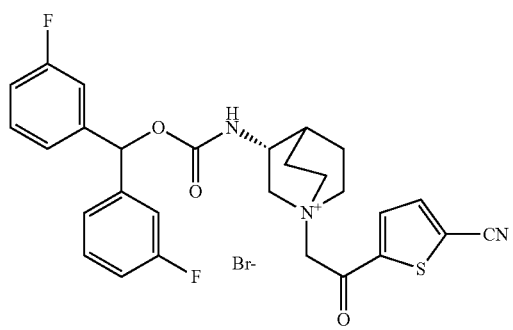 [SMILES: N#Cc1ccc(C(=O)C[N+]23CCC(CC2)[C@@H](NC(=O)OC(c2cccc(F)c2)c2cccc(F)c2)C3)s1 ; [Br-]]

5-(2-Bromoacetyl)thiophene-2-carbonitrile (33.4 mg, 0.14 mmol) was added to a solution of (R)-bis(3-fluorophenyl)methyl quinuclidin-3-ylcarbamate (54 mg, 0.14 mmol, prepared as in example 1) in ethyl acetate (2 ml). The resulting solution was stirred at room temperature for two days, then 5-(2-bromoacetyl)thiophene-2-carbonitrile (3.4 mg, 0.015 mmol) was added, and the stirring was kept for additional 16 hours. Et₂O was added and the precipitate was recovered by filtration to afford (R)-3-((bis(3-fluorophenyl)methoxy)carbonylamino)-1-(2-(5-cyanothiophen-2-yl)-2-oxoethyl)-1-azoniabicyclo[2.2.2]octane bromide (68 mg).

¹H NMR (300 MHz, DMSO-d6) δ ppm 8.08-8.22 (m, 3H), 7.34-7.58 (m, 2H), 7.20-7.34 (m, 4H), 7.04-7.20 (m, 2H), 6.73 (s, 1H), 5.06 (br. s., 2H), 3.86-4.24 (m, 2H), 3.56-3.86 (m, 3H), 3.40-3.56 (m, 2H), 2.10-2.26 (m, 2H), 1.84-2.08 (m, 3H);

LC-MS (ESI POS): 522.14 (M+).

Example 9

Preparation of (R)-3-((bis(3-fluorophenyl)methoxy)carbonylamino)-1-(2-oxo-2-(pyridin-2-yl)ethyl)-1-azoniabicyclo[2.2.2]octane bromide (Compound 27)

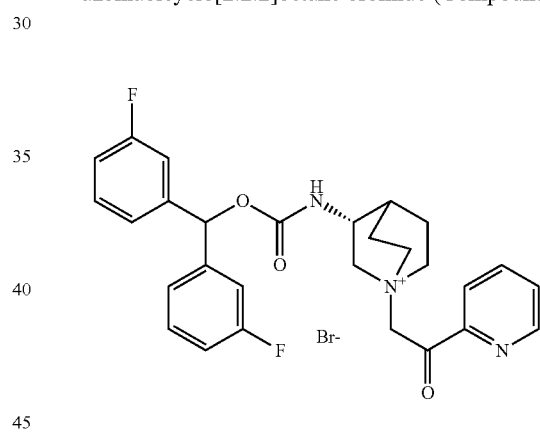

2-Bromo-1-(pyridin-2-yl)ethanone hydrobromide (39.2 mg, 0.14 mmol) was added to a solution of (R)-bis(3-fluorophenyl)methyl quinuclidin-3-ylcarbamate (52 mg, 0.14 mmol, prepared as in example 1) in ethyl acetate (2 ml). The reaction was stirred at room temperature for 16 hours, then Et₂O (1 mL) was added, and the precipitate was collected by suction filtration and dried under vacuum at 40° C. overnight. The product was further purified by preparative HPLC to obtain (R)-3-((bis(3-fluorophenyl)methoxy)-carbonylamino)-1-(2-oxo-2-(pyridin-2-yl)ethyl)-1-azoniabicyclo[2.2.2]octane bromide (16.5 mg).

¹H NMR (300 MHz, DMSO-d6) δ ppm 8.76 (dt, 1H) 8.15-8.24 (m, 1H) 8.01-8.15 (m, 2H) 7.78 (ddd, 1H) 7.43 (td, 2H) 7.19-7.36 (m, 4H) 7.07-7.19 (m, 2H) 6.73 (s, 1H) 5.22 (s, 2H) 3.94-4.19 (m, 2H) 3.44-3.90 (m, 5H) 2.17-2.38 (m, 1H) 1.78-2.17 (m, 411);

LC-MS (ESI POS): 492.20 (M+).

The following compound was prepared following the route described in Example 9 using the suitable alkylating agents instead of 2-bromo-1-(pyridin-2-yl)ethanone hydrobromide.

TABLE 3

| Compound | Structure and Name | ¹H-NMR | [M⁺] |
|---|---|---|---|
| 28 | | (300 MHz, DMSO-d6) δ ppm 11.71 (br. s., 1 H) 8.86 (d, 1 H) 8.14 (d, 1 H) 7.43 (td, 2 H) 7.25 (d, 4 H) 7.14 (td, 2 H) 6.90 (d, 1 H) 6.72 (s, 1 H) 4.20 (s, 2 H) 3.89-4.13 (m, 2 H) 3.47-3.76 (m, 5 H) 1.75-2.40 (m, 5 H) | 497.22 |

Example 10

Preparation of (R)-3-((bis(3-fluorophenyl)methoxy)carbonylamino)-1-(2-oxo-2-(thiophen-2-yl)ethyl)-1-azoniabicyclo[2.2.2]octane chloride (Compound 29)

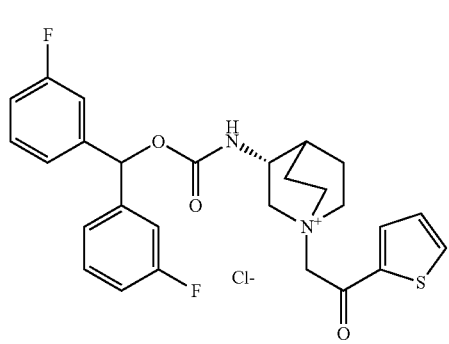 [SMILES: O=C(N[C@H]1C[N+]2(CC(=O)c3cccs3)CCC1CC2)OC(c1cccc(F)c1)c1cccc(F)c1 ; [Cl-]]

(R)-Bis(3-fluorophenyl)methyl quinuclidin-3-ylcarbamate (35 mg, 0.09 mmol, prepared as in example 1) and 2-chloro-1-(thiophen-2-yl)ethanone (16.6 mg, 0.10 mmol) were dissolved in acetonitrile (2 ml) and stirred at room temperature for 16 hours. Acetonitrile was evaporated and the crude was purified by flash chromatography (DCM/MeOH=9/1) to obtain (R)-3-((bis(3-fluorophenyemethoxy)carbonylamino)-1-(2-oxo-2-(thiophen-2-yl)ethyl)-1-azoniabicyclo[2.2.2]octane chloride (50.1 mg).

¹H NMR (300 MHz, DMSO-d₆) δ ppm 8.20 (dd, 2H), 8.10 (dd, 1H), 7.38-7.54 (m, 2H), 7.29-7.38 (m, 2H), 7.25 (br. s., 3H), 6.95-7.21 (m, 2H), 6.73 (s, 1H), 5.03 (s, 2H), 3.85-4.23 (m, 2H), 3.48-3.80 (m, 5H), 1.95-2.32 (m, 4H), 1.91 (br. s., 1H);

LC-MS (ESI POS): 497.33 (M+).

Example 11

Preparation of (R)-3-((bis(3-fluorophenyl)methoxy)carbonylamino)-1-(2-oxo-2-phenylethyl)-1-azoniabicyclo[2.2.2]octane chloride (Compound 30)

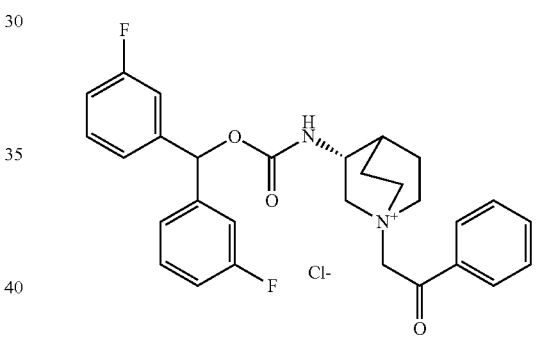

2-Chloro-1-phenylethanone (20.8 mg, 0.13 mmol) was added to a solution of (R)-bis(3-fluorophenyl)methyl quinuclidin-3-ylcarbamate (50 mg, 0.13 mmol, prepared as in example 1) in ethyl acetate (2 ml). The reaction was stirred at room temperature overnight, then the solvent was evaporated under vacuum. The residue was treated with Et₂O (4 ml) and sonicated to obtain a solid, which was collected by suction filtration and purified by flash chromatography (DCM/MeOH=95/5), to obtain (R)-3-((bis(3-fluorophenyl)methoxy)carbonylamino)-1-(2-oxo-2-phenylethyl)-1-azoniabicyclo[2.2.2]octane chloride (37.2 mg).

¹H NMR (300 MHz, DMSO-d₆) δ ppm 8.22 (d, 1H) 7.91-8.05 (m, 2H) 7.68-7.85 (m, 1H) 7.54-7.68 (m, 2H) 7.43 (td, 2H) 7.21-7.36 (m, 4H) 7.01-7.20 (m, 2H) 6.73 (s, 1H) 5.15 (s, 2H) 3.95-4.18 (m, 2H) 3.63-3.92 (m, 4H) 3.47-3.63 (m, 1H) 1.98-2.36 (m, 4H) 1.79-1.98 (m, 1H);

LC-MS (ESI POS): 491.21 (M+).

Example 12

Preparation of (R)-3-((bis(3-fluorophenyl)methoxy)carbonylamino)-1-(2-phenoxyethyl)-1-azoniabicyclo[2.2.2]octane bromide (Compound 31)

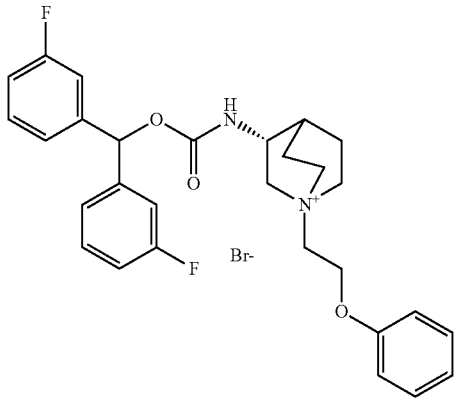 [SMILES: O=C(N[C@H]1C[N+]2(CCOc3ccccc3)CCC1CC2)OC(c1cccc(F)c1)c1cccc(F)c1 ; [Br-]]

(R)-Bis(3-fluorophenyl)methyl quinuclidin-3-ylcarbamate (50 mg, 0.13 mmol, prepared as in example 1) was added to a solution of (2-bromoethoxy)benzene (27.0 mg, 0.13 mmol) in ethyl acetate (2 ml). The mixture was stirred at room temperature overnight. Then (2-bromoethoxy)benzene (27 mg, 0.13 mmol) was added, and the mixture was heated at 100° C. for 15 minutes under microwave irradiation. A catalytic amount of potassium iodide was added, and the reaction was heated at 120° C. for 1 hour under microwave irradiation. The precipitate was collected by filtration and dried to obtain (R)-3-((bis(3-fluorophenyl)methoxy)carbonylamino)-1-(2-phenoxyethyl)-1-azoniabicyclo[2.2.2]octane bromide (17 mg).

$^1$H NMR (300 MHz, DMSO-d$_6$) δ ppm 8.05 (d, 1H), 7.42 (td, 2H), 7.29-7.37 (m, 2H), 7.20-7.29 (m, 4H), 7.08-7.20 (m, 2H), 6.90-7.06 (m, 3H), 6.73 (s, 1H), 4.38-4.46 (m, 2H), 3.95-4.11 (m, 1H), 3.84-3.95 (m, 1H), 3.60-3.72 (m, 2H), 3.44-3.61 (m, 4H), 3.33-3.38 (m, 1H), 2.06-2.22 (m, 2H), 1.73-2.05 (m, 3H);

LC-MS (ESI POS): 493.34 (M+).

Example 13

Preparation of (R)-3-((bis(3-fluorophenyl)methoxy)carbonyl amino)-1-(2-(2,3-dihydrobenzofuran-5-yl)ethyl)-1-azoniabicyclo[2.2.2]octane bromide (Compound 32)

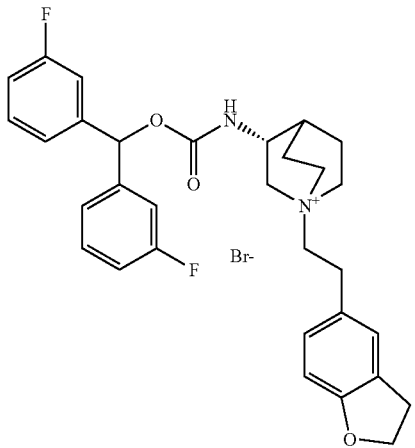 [SMILES: O=C(N[C@H]1C[N+]2(CCc3ccc4c(c3)CCO4)CCC1CC2)OC(c1cccc(F)c1)c1cccc(F)c1 ; [Br-]]

To a solution of (R)-bis(3-fluorophenyl)methyl quinuclidin-3-ylcarbamate (53 mg, 0.14 mmol, prepared as in example 1) in ethyl acetate (2 ml), 5-(2-bromoethyl)-2,3-dihydrobenzofuran (32.3 mg, 0.14 mmol) was added. The resulting mixture was stirred at room temperature for 8 days, and then the solvent was evaporated, and the crude was purified by flash chromatography (DCM/MeOH=95/5) to collect (R)-3-((bis(3-fluorophenyl)-methoxy)carbonylamino)-1-(2-(2,3-dihydrobenzofuran-5-yl)ethyl)-1-azoniabicyclo[2.2.2]octane bromide (22.2 mg).

$^1$H NMR (300 MHz, DMSO-d6) δ ppm 8.08 (d, 1H), 7.36-7.51 (m, 2H), 7.26 (d, 4H), 7.06-7.19 (m, 3H), 7.00 (d, 1H), 6.64-6.81 (m, 2H), 4.50 (t, 2H), 3.92-4.13 (m, 1H), 3.83 (t, 1H), 3.37-3.59 (m, 4H), 3.33 (d, 2H), 3.19-3.25 (m, 1H), 3.15 (t, 2H), 2.90 (m, 2H), 2.04-2.25 (m, 2H), 1.68-2.04 (m, 3H);

LC-MS (ESI POS): 519.30 (M+).

Example 14

Preparation of (R)-3-((bis(3-fluorophenyl)methoxy)carbonylamino)-1-(4-fluorophenethyl)-1-azoniabicyclo[2.2.2]octane bromide (Compound 33)

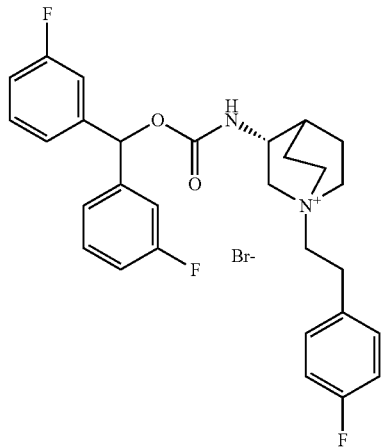 [SMILES: O=C(N[C@H]1C[N+]2(CCc3ccc(F)cc3)CCC1CC2)OC(c1cccc(F)c1)c1cccc(F)c1 ; [Br-]]

(R)-bis(3-Fluorophenyl)methyl quinuclidin-3-ylcarbamate (55 mg, 0.14 mmol, prepared as in example 1) was dissolved in ethyl acetate (2 ml), and 1-(2-bromoethyl)-4-fluorobenzene (21 µl, 0.15 mmol) was added. The reaction was stirred at room temperature for 24 hours, then 1-(2-bromoethyl)-4-fluorobenzene (6.21 µl, 0.04 mmol) was added again. After being stirred at room temperature for 2 days, the reaction was concentrated under vacuum, and the crude was first purified by flash chromatography (DCM/MeOH=9/1) and then triturated with DCM/Et$_2$O (1/1) to obtain (R)-3-((bis(3-fluorophenyl)-methoxy)carbonylamino)-1-(4-fluorophenethyl)-1-azoniabicyclo[2.2.2]octane bromide (45 mg).

$^1$H NMR (300 MHz, DMSO-d6) δ ppm 8.09 (d, 1H), 7.39-7.48 (m, 2H), 7.35 (dd, 2H), 7.23-7.30 (m, 4H), 7.09-7.23 (m, 4H), 6.74 (s, 1H), 3.94-4.15 (m, 1H), 3.64-3.94 (m, 1H), 3.41-3.59 (m, 4H), 3.35 (d, 2H), 3.14-3.25 (m, 1H), 3.00 (dd, 2H), 2.04-2.25 (m, 2H), 1.69-2.04 (m, 3 µl);

LC-MS (ESI POS): 495.24 (M+).

Example 15

Preparation of (R)-3-(benzhydryloxycarbonylamino)-1-(2-oxo-2-phenylethyl)-1-azoniabicyclo[2.2.2]octane chloride (Compound 34)

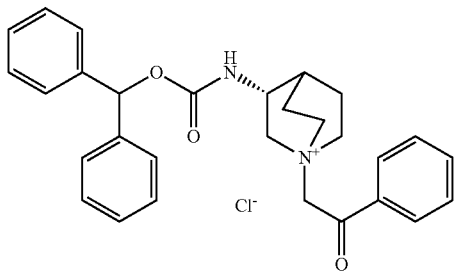 [SMILES: O=C(N[C@H]1C[N+]2(CC(=O)c3ccccc3)CCC1CC2)OC(c1ccccc1)c1ccccc1 ; [Cl-]]

2-Chloro-1-phenylethanone (55.0 mg, 0.36 mmol) was added to a solution of (R)-benzhydryl quinuclidin-3-ylcarbamate (100 mg, 0.30 mmol, prepared as in example 2) in ethyl acetate (4 ml). The reaction was stirred at room temperature overnight. The suspension was decanted, solvent was removed, and the product was evaporated to dryness. Et$_2$O was added, and the suspension was sonicated. The precipitate was collected by suction filtration and dried under vacuum at 40° C. to obtain (R)-3-(benzhydryloxycarbonylamino)-1-(2-oxo-2-phenylethyl)-1-azoniabicyclo-[2.2.2]octane chloride (110 mg)

$^1$H NMR (300 MHz, DMSO-d$_6$) δ ppm 8.15 (d, 1H) 7.94-8.05 (m, 2H) 7.69-7.81 (m, 1H) 7.52-7.66 (m, 2H) 7.11-7.45 (m, 10H) 6.71 (s, 1H) 5.15 (s, 2H) 3.92-4.19 (m, 2H) 3.44-3.86 (m, 5H) 1.96-2.32 (m, 4H) 1.73-1.96 (m, 1H);

LC-MS (ESI POS): 455.21 (M+).

Example 16

Preparation of (R)-3-((bis(4-fluorophenyl)methoxy)carbonylamino)-1-(2-oxo-2-phenylethyl)-1-azoniabicyclo[2.2.2]octane chloride (Compound 35)

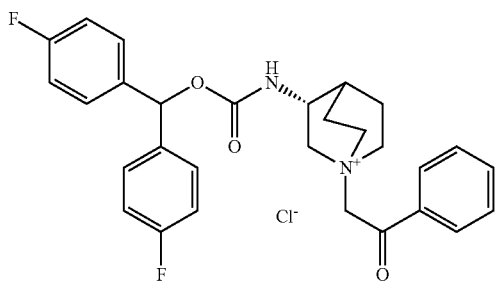 [SMILES: O=C(N[C@H]1C[N+]2(CC(=O)c3ccccc3)CCC1CC2)OC(c1ccc(F)cc1)c1ccc(F)cc1 ; [Cl-]]

2-Chloro-1-phenylethanone (13 mg, 0.09 mmol) was added to a solution of (R)-bis(4-fluorophenyl)methyl quinuclidin-3-ylcarbamate (32.0 mg, 0.09 mmol, prepared as in example 3) in ethyl acetate (2 ml). The reaction was stirred at room temperature overnight. Then more 2-chloro-1-phenylethanone (2.7 mg, 0.02 mmol) was added to the solution, and the reaction was stirred for additional 24 hours. The reaction was evaporated to dryness, and the residue was triturated in Et$_2$O. Then isopropyl ether was added, and the product was sonicated and the precipitate was collected by suction filtration to obtain (R)-3-((bis(4-fluorophenyl)methoxy)carbonylamino)-1-(2-oxo-2-phenylethyl)-1-azoniabicyclo[2.2.2]octane chloride (32.4 mg)

$^1$H NMR (300 MHz, DMSO-d$_6$) δ ppm 8.09-8.22 (m, 1H) 7.91-8.05 (m, 2H) 7.69-7.81 (m, 1H) 7.55-7.69 (m, 2H) 7.34-7.48 (m, 4H) 7.09-7.31 (m, 4H) 6.73 (s, 1H) 5.14 (s, 2H) 3.86-4.20 (m, 2H) 3.47-3.87 (m, 5H) 1.61-2.41 (m, 5H);

LC-MS (ESI POS): 491.21 (M+).

Example 17

Preparation of (3R)-3-(((4-methoxyphenyl)(phenyl)methoxy)-carbonylamino)-1-(2-oxo-2-(thiophen-2-yl)ethyl)-1-azoniabicyclo[2.2.2]-octane chloride (Compound 36)

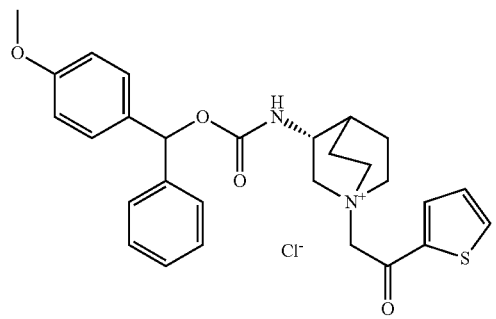 [SMILES: COc1ccc(C(OC(=O)N[C@H]2C[N+]3(CC(=O)c4cccs4)CCC2CC3)c2ccccc2)cc1 ; [Cl-]]

2-Chloro-1-(thiophen-2-yl)ethanone (12.0 mg, 0.07 mmol) was added to a solution of (4-methoxyphenyl)(phenyl)methyl(R)-quinuclidin-3-ylcarbamate (22.0 mg, 0.06 mmol, prepared as in example 3) in ethyl acetate (2 ml). The reaction was stirred at room temperature for two days. The reaction was evaporated to dryness. The crude was purified by flash chromatography (DCM/MeOH=95/5) to obtain (3R)-3-(((4-methoxyphenyl)(phenyl)methoxy)carbonylamino)-1-(2-oxo-2-(thiophen-2-yl)ethyl)-1-azoniabicyclo[2.2.2]octane chloride (23 mg, mixture of diastereoisomers).

$^1$H NMR (300 MHz, DMSO-d$_6$) δ ppm 8.20 (d, 1H) 8.08 (d, 1H) 8.04-8.13 (m, 1H) 7.35 (m, 5H) 7.29 (m, 3H) 6.74-7.04 (m, 2H) 6.66 (s, 1H) 5.00 (s, 2H) 3.88-4.19 (m, 2H) 3.74 (s, 3H) 3.57-3.72 (m, 4H) 3.42-3.57 (m, 1H) 1.92-2.26 (m, 4H) 1.64-1.92 (m, 1H);

LC-MS (ESI POS): 491.21 (M+).

The following compounds were prepared following the route described in Example 17 using the suitable intermediates (Example 3, Table 1) instead of (4-methoxyphenyl)(phenyl)methyl(R)-quinuclidin-3-ylcarbamate. These compounds were obtained as a mixture of diastereoisomers.

TABLE 4

| Compound | Structure | $^1$H-NMR | [M$^+$] |
|---|---|---|---|
| 37 | 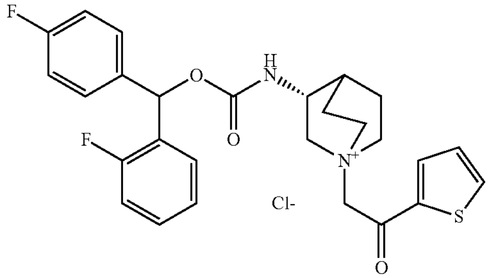 [SMILES: O=C(N[C@H]1C[N+]2(CC(=O)c3cccs3)CCC1CC2)OC(c1ccc(F)cc1)c1ccccc1F ; [Cl-]] | (300 MHz, DMSO-d6) δ ppm 8.20 (d, 1 H) 8.15-8.26 (m, 1 H) 8.08 (d, 1 H) 7.32-7.54 (m, 5 H) 7.17-7.30 (m, 4 H) 6.90 (s, 1 H) 5.00 (s, 2 H) 3.84-4.19 (m, 2 H) 3.57-3.81 (m, 4 H) 3.51 (m, 1 H) 1.95-2.28 (m, 4 H) 1.81-1.93 (m, 1 H) | 497.21 |
| 38 | 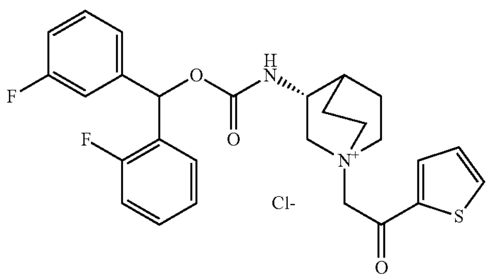 [SMILES: O=C(N[C@H]1C[N+]2(CC(=O)c3cccs3)CCC1CC2)OC(c1cccc(F)c1)c1ccccc1F ; [Cl-]] | (300 MHz, DMSO-d6) δ ppm 8.20 (d, 1 H) 8.15-8.29 (m, 1 H) 8.08 (d, 1 H) 7.30-7.60 (m, 4 H) 7.04-7.30 (m, 5 H) 6.91 (s, 1 H) 5.00 (s, 2 H) 3.97-4.11 (m, 2 H) 3.47-3.78 (m, 5 H) 1.81-2.25 (m, 5 H) | 497.22 |
| 39 | 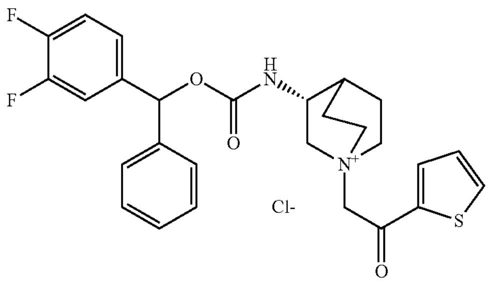 [SMILES: O=C(N[C@H]1C[N+]2(CC(=O)c3cccs3)CCC1CC2)OC(c1ccccc1)c1ccc(F)c(F)c1 ; [Cl-]] | (300 MHz, DMSO-d6) δ ppm 8.20 (d, 1 H) 8.16 (br. s., 1 H) 8.09 (d, 1 H) 7.18-7.55 (m, 9 H) 6.71 (s, 1 H) 5.02 (s, 2 H) 3.86-4.21 (m, 2 H) 3.42-3.81 (m, 5 H) 1.93-2.29 (m, 4 H) 1.75-1.93 (m, 1 H) | 497.22 |

Example 18

Preparation of (3R)-1-(2-oxo-2-(thiophen-2-yl)ethyl)-3-((phenyl(4-(trifluoromethyl)phenyl)methoxy)carbonylamino)-1-azoniabicyclo-[2.2.2]octane chloride (Compound 41)

1. Preparation of phenyl(4-(trifluoromethyl)phenyl)methyl(R)-quinuclidin-3-ylcarbamate (Compound 40)

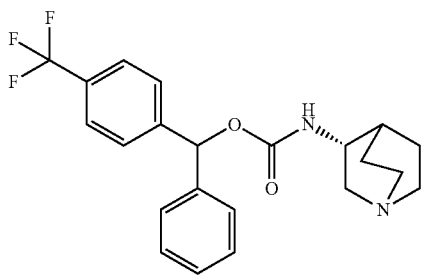 [SMILES: O=C(N[C@H]1CN2CCC1CC2)OC(c1ccccc1)c1ccc(C(F)(F)F)cc1]

In a first flask, (R)-quinuclidin-3-amine dihydrochloride (100 mg, 0.50 mmol) was dissolved in MeOH (5 ml), and water (0.5 ml). NaHCO$_3$ (84.0 g, 1.00 mmol) was added, and the reaction was stirred at room temperature for 1 hour. The reaction mixture was evaporated, and the residue was dissolved in dry DMF (5 ml), and CDI (81.0 mg, 0.50 mmol) was added. The reaction was stirred at room temperature overnight.

In a second flask, phenyl(4-(trifluoromethyl)phenyl)methanol (0.25 g, 1.00 mmol) was dissolved in dry DMF (3 ml), and sodium hydride (60% dispersion in mineral oil, 24.0 mg, 1.00 mmol) was added portionwise at 0° C. The reaction was stirred at room temperature for 15 minutes and then was poured into the first flask.

The resulting mixture was stirred at room temperature overnight, then it was portioned between Et$_2$O and water. The organic phase was washed with brine and dried over sodium sulphate. The solvent was removed in vacuo and the crude was purified by flash chromatography (DCM/MeOH=95/5 to DCM/MeOH/TEA=75/25/0.5) to obtain phenyl(4-(trifluoromethyl)-phenyl)methyl(R)-quinuclidin-3-ylcarbamate (56.0 mg, mixture of diastereoisomers).

2. Preparation of (3R)-1-(2-oxo-2-(thiophen-2-yl)ethyl)-3-((phenyl(4-(trifluoromethyl)phenyl)methoxy)carbonylamino)-1-azoniabicyclo[2.2.2]octane chloride (Compound 41)

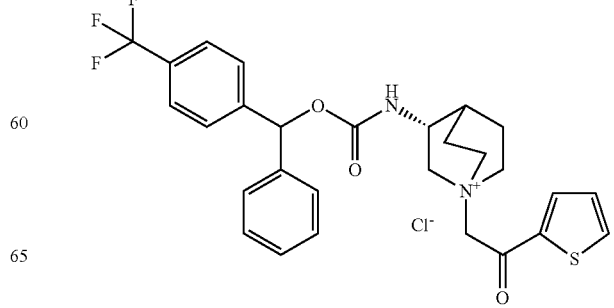

Phenyl(4-(trifluoromethyl)phenyl)methyl(R)-quinuclidin-3-ylcarbamate (56.0 mg, 0.14 mmol) was dissolved in ethyl acetate (1 ml) and acetonitrile (0.5 ml). The resulting solution was treated with 2-chloro-1-(thiophen-2-yl)ethanone (24.0 mg, 0.15 mmol) and stirred at room temperature overnight. The solvent was evaporated, and the crude was first purified by flash chromatography (DCM/MeOH=95/5) and then by preparative HPLC(CH₃CN/H₂O) to afford (3R)-1-(2-oxo-2-(thiophen-2-yl)ethyl)-3-((phenyl(4-(trifluoromethyl)phenyl)methoxy)carbonylamino)-1-azoniabicyclo[2.2.2]-octane chloride (30.0 mg, mixture of diastereoisomers).

¹H NMR (300 MHz, DMSO-d₆) δ ppm 8.18-8.26 (m, 2H), 8.09 (d, 1H), 7.69-7.79 (m, 2H), 7.55-7.69 (m, 2H), 7.17-7.49 (m, 6H), 6.80 (s, 1H), 5.01 (s, 2H), 3.92-4.27 (m, 2H), 3.44-3.88 (m, 5H), 1.73-2.37 (m, 5H);

LC-MS (ESI POS): 529.13 (M+).

Example 19

Preparation of (3R)-3-(((2-chlorophenyl)(4-chlorophenyl)methoxy)-carbonylamino)-1-(2-oxo-2-(thiophen-2-yl)ethyl)-1-azoniabicyclo-[2.2.2]octane chloride (Compound 43)

1. Preparation of (2-chlorophenyl)(4-chlorophenyl)methyl(R)-quinuclidin-3-ylcarbamate (Compound 42)

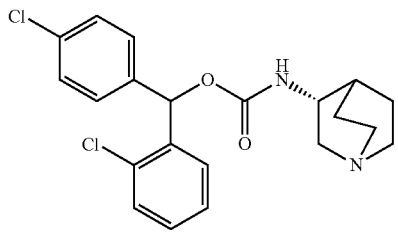 [SMILES: O=C(N[C@H]1CN2CCC1CC2)OC(c1ccc(Cl)cc1)c1ccccc1Cl]

In a first flask, (R)-quinuclidin-3-amine dihydrochloride (80.0 mg, 0.40 mmol) was dissolved in MeOH (8 ml) and water (0.8 ml). Sodium bicarbonate (67.5 mg, 0.80 mmol) was added, and the reaction was stirred at room temperature for 1 hour. The reaction was evaporated to dryness, and the solid was dissolved in dry DMF (8 ml). CDI (65.1 mg, 0.40 mmol) was added, and the reaction was stirred at room temperature overnight.

In a second flask, (2-chlorophenyl)(4-chlorophenyl)methanol (100 mg, 0.39 mmol) was dissolved in dry DMF (3 ml) and treated with sodium hydride (60% dispersion in mineral oil, 15.8 mg, 0.39 mmol) at 0° C. The ice-bath was removed, and the reaction was stirred at room temperature for 20 minutes, and then it was added to the first reaction.

The resulting mixture was stirred at room temperature overnight, and then it was portioned between Et₂O and water. The organic phase was washed with brine, dried over Na₂SO₄, filtered, and evaporated to dryness. The crude was purified by flash chromatography (DCM/MeOH=9/1 to DCM/MeOH=75/25) to obtain (2-chlorophenyl)(4-chlorophenyl)methyl(R)-quinuclidin-3-ylcarbamate (95 mg, mixture of diastereoisomers).

2. Preparation of (3R)-3-(((2-chlorophenyl)(4-chlorophenyl)methoxy)carbonylamino)-1-(2-oxo-2-(thiophen-2-yl)ethyl)-1-azoniabicyclo[2.2.2]octane chloride (Compound 43)

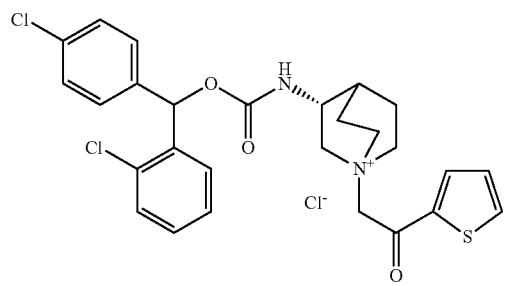 [SMILES: O=C(N[C@H]1C[N+]2(CC(=O)c3cccs3)CCC1CC2)OC(c1ccc(Cl)cc1)c1ccccc1Cl ; [Cl-]]

To a solution of (2-chlorophenyl)(4-chlorophenyl)methyl (R)-quinuclidin-3-ylcarbamate (95.0 mg, 0.23 mmol) in ethyl acetate (3 ml), 2-chloro-1-(thiophen-2-yl)ethanone (37.6 mg, 0.23 mmol) was added, and the mixture was stirred at room temperature overnight. The solvent was removed under vacuum, and the residue was taken up in diethyl ether and filtered. The product was purified by flash chromatography (DCM/MeOH=95/5) to obtain (3R)-3-(((2-chlorophenyl)(4-chlorophenyl)methoxy)carbonylamino)-1-(2-oxo-2-(thiophen-2-yl)ethyl)-1-azoniabicyclo[2.2.2]octane chloride (45.0 mg, mixture of diastereoisomers).

¹H NMR (300 MHz, DMSO-d₆) δ ppm 8.15-8.31 (m, 2H) 8.02-8.15 (m, 1H) 7.27-7.66 (m, 9H) 6.81-7.00 (m, 1H) 5.03 (s, 2H) 3.85-4.23 (m, 2H) 3.59-3.85 (m, 4H) 3.46-3.59 (m, 1H) 1.95-2.28 (m, 4H) 1.82-1.93 (m, 1H);

LC-MS (ESI POS): 529.09 (M+).

Example 20

Preparation of (R)-1-(2-oxo-2-(thiophen-2-yl)ethyl)-3-((thiophen-2-ylmethoxy)carbonylamino)-1-azoniabicyclo[2.2.2]octane chloride (Compound 45)

1—Preparation of (R)-thiophen-2-ylmethyl quinuclidin-3-ylcarbamate (Compound 44)

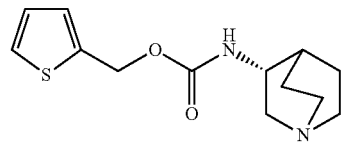 [SMILES: O=C(N[C@H]1CN2CCC1CC2)OCc1cccs1]

In a first flask, (R)-quinuclidin-3-amine dihydrochloride (100 mg, 0.50 mmol) was dissolved in MeOH (10 ml) and water (1 ml). Sodium bicarbonate (84 mg, 1.00 mmol) was added, and the reaction was stirred at room temperature for 1 hour. The reaction was evaporated to dryness, and the solid was dissolved in dry DMF (10 ml). CDI (81 mg, 0.50 mmol) was added, and the reaction was stirred at room temperature overnight.

In a second flask, thiophen-2-ylmethanol (114 mg, 1.00 mmol) was dissolved in dry DMF (3 ml) and treated with sodium hydride (60% dispersion in mineral oil, 40.0 mg, 1.00 mmol) at 0° C. The ice-bath was removed, and the reaction was stirred at room temperature for 20 minutes, and then it was poured into the first flask.

The resulting mixture was stirred at room temperature overnight, and then it was portioned between Et$_2$O and water. The organic phase was washed with brine, dried over Na$_2$SO$_4$, filtered, and evaporated to dryness. The crude was purified by flash chromatography (DCM/MeOH=9/1 to 75/25) to obtain (R)-thiophen-2-ylmethyl quinuclidin-3-yl-carbamate (50 mg).

2. Preparation of (R)-1-(2-oxo-2-(thiophen-2-yl)ethyl)-3-((thiophen-2-ylmethoxy)carbonylamino)-1-azoniabicyclo[2.2.2]octane chloride (Compound 45)

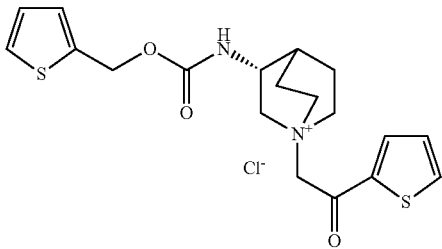 [SMILES: O=C(N[C@H]1C[N+]2(CC(=O)c3cccs3)CCC1CC2)OCc1cccs1 ; [Cl-]]

2-Chloro-1-(thiophen-2-yl)ethanone (30.2 mg, 0.19 mmol) was added to a solution of (R)-thiophen-2-ylmethyl quinuclidin-3-ylcarbamate (50.0 mg, 0.19 mmol) in EtOAc (3 ml). The reaction was stirred at room temperature overnight. The solvent was removed, and the residue was triturated in Et$_2$O, filtered and dried to give (R)-1-(2-oxo-2-(thiophen-2-yl)ethyl)-3-((thiophen-2-ylmethoxy)carbonylamino)-1-azoniabicyclo[2.2.2]octane chloride (60 mg).
$^1$H NMR (300 MHz, DMSO-d$_6$) δ ppm 8.21 (dd, 1H), 8.12 (dd, 1H), 7.96 (br. s., 1H), 7.55 (dd, 1H), 7.35 (dd, 1H), 7.16 (dd, 1H), 7.03 (dd, 1H), 5.22 (s, 2H), 5.04 (s, 2H), 3.90-4.19 (m, 2H), 3.58-3.84 (m, 4H), 3.44-3.58 (m, 1H), 1.72-2.24 (m, 5H);
LC-MS (ESI POS): 391.23 (M+).

Example 21

Preparation of (R)-3-((bis(3-fluorophenyl)methoxy)carbonothioylamino)-1-(2-oxo-2-(thiophen-2-yl)ethyl)-1-azoniabicyclo[2.2.2]octane chloride (Compound 47)

1. Preparation of (R)—O-bis(3-fluorophenyl)methyl quinuclidin-3-ylcarbamothioate (Compound 46)

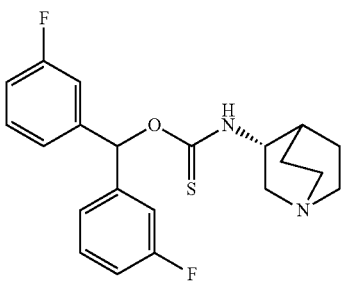 [SMILES: Fc1cccc(C(OC(=S)N[C@H]2CN3CCC2CC3)c2cccc(F)c2)c1]

In a first flask, (R)-quinuclidin-3-amine dihydrochloride (500 mg, 2.51 mmol) was dissolved in MeOH (25 ml) and water (2.5 ml). Sodium bicarbonate (211 mg, 2.51 mmol) was added, and the reaction was stirred at room temperature for 1 hour. The solvent was evaporated to dryness, and the residue was suspended in dry DMF (25 ml) and treated with di(1H-imidazol-1-yl)methanethione (448 mg, 2.51 mmol). The reaction was stirred 4 hours at room temperature.

In a second flask, NaH (60% dispersion in mineral oil, 187 mg, 4.68 mmol) was added portionwise to a solution of bis(3-fluorophenyl)methanol (1.03 g, 4.68 mmol) in dry DMF (25 ml) at 0° C. The reaction was stirred at room temperature for 30 minutes, and then it was added to the first flask.

The resulting mixture was stirred at room temperature overnight, and then the reaction was portioned between Et$_2$O and water. The organic phase was dried over Na$_2$SO$_4$, filtered, and evaporated to dryness. The crude was purified by flash chromatography (DCM/MeOH=9/1 and then DCM/MeOH=75/25+0.5% TEA) to obtain (R)—O-bis(3-fluorophenyl)methyl quinuclidin-3-ylcarbamothioate (60 mg).

2. Preparation of (R)-3-((bis(3-fluorophenyl)methoxy)carbonothioylamino)-1-(2-oxo-2-(thiophen-2-yl)ethyl)-1-azoniabicyclo[2.2.2]octane chloride (Compound 47)

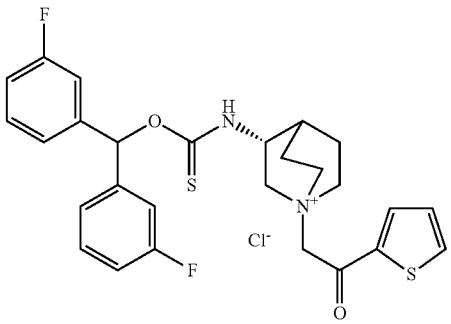 [SMILES: O=C(C[N+]12CCC(CC1)[C@@H](NC(=S)OC(c1cccc(F)c1)c1cccc(F)c1)C2)c1cccs1 ; [Cl-]]

To a solution of (R)—O-bis(3-fluorophenyl)methyl quinuclidin-3-ylcarbamothioate (60 mg, 0.15 mmol) in ethyl acetate (1 ml), 2-chloro-1-(thiophen-2-yl)ethanone (27.3 mg, 0.17 mmol) was added. The reaction was stirred at room temperature for 3 days. The solvent was evaporated, and the residue was purified by flash chromatography (DCM/MeOH=75/25) to obtain (R)-3-((bis(3-fluorophenyl)methoxy)carbonothioylamino)-1-(2-oxo-2-(thiophen-2-yl)ethyl)-1-azoniabicyclo[2.2.2]octane chloride (20 mg).
$^1$H NMR (300 MHz, DMSO-d6 353K) δ ppm 9.74 (br. s., 1H), 8.16 (dd, 1H), 8.07 (dd, 1H), 7.38-7.52 (m, 3H), 7.33 (dd, 1H), 7.20-7.30 (m, 4H), 7.04-7.20 (m, 2H), 4.97 (s, 2H), 4.45-4.70 (m, 1H), 4.13-4.35 (m, 1H), 3.61-3.90 (m, 5H), 2.32-2.46 (m, 2H), 1.87-2.26 (m, 3H);
LC-MS (ESI POS): 513.25 (M+).

Example 22

Preparation of (3R)-1-benzyl-3-((bis(3-fluorophenyl)methoxy)-carbonylamino)-1-methylpyrrolidinium iodide (Compound 49)

1. Preparation of (R)-bis(3-fluorophenyl)methyl 1-benzylpyrrolidin-3-ylcarbamate (Compound 48)

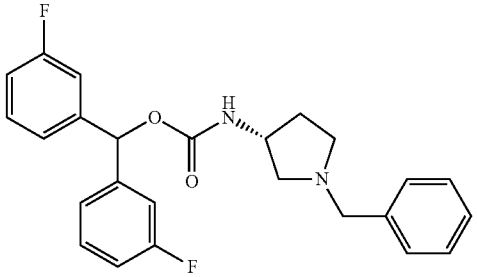 [SMILES: O=C(N[C@@H]1CCN(Cc2ccccc2)C1)OC(c1cccc(F)c1)c1cccc(F)c1]

In a first flask, CDI (184 mg, 1.135 mmol) was added to a solution of (R)-1-benzylpyrrolidin-3-amine (200 mg, 1.13 mmol) in dry DMF (20 ml), and the reaction was stirred at room temperature overnight.

In a second flask, bis(3-fluorophenyl)methanol (375 mg, 1.70 mmol) was dissolved in dry DMF (9 ml) and treated with sodium hydride (60% dispersion in mineral oil, 68.1 mg, 1.703 mmol) at 0° C. The ice-bath was removed, and the reaction was stirred at room temperature for 20 minutes, and then it was added to the first flask.

The resulting mixture was stirred at room temperature overnight, and then portioned between $Et_2O$ and water. The organic phase was washed with brine, dried over $Na_2SO_4$, filtered, and evaporated to dryness. The crude was purified by flash chromatography (DCM/MeOH=98/2) to give (R)-bis(3-fluorophenyl)methyl 1-benzylpyrrolidin-3-ylcarbamate (300 mg).

2. Preparation of (3R)-1-benzyl-3-((bis(3-fluorophenyl)methoxy)-carbonylamino)-1-methylpyrrolidinium iodide (Compound 49)

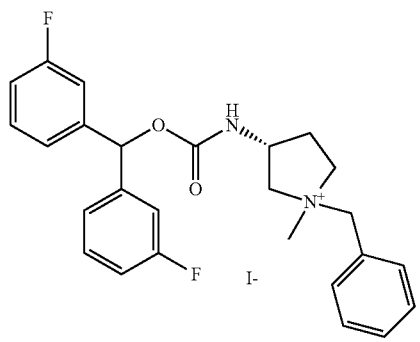 [SMILES: C[N+]1(Cc2ccccc2)CC[C@@H](NC(=O)OC(c2cccc(F)c2)c2cccc(F)c2)C1 ; [I-]]

To a solution of (R)-bis(3-fluorophenyl)methyl 1-benzylpyrrolidin-3-ylcarbamate (300 mg, 0.71 mmol) in EtOAc (9 ml), iodomethane (44.2 μl, 0.71 mmol) was added, and the reaction was stirred at room temperature overnight. The solvent was then removed under vacuum, and the residue was triturated with diethyl ether. The product was purified by flash chromatography (DCM/MeOH=99/1) and then by preparative HPLC to give (3R)-1-benzyl-3-((bis(3-fluorophenyl)methoxy)carbonylamino)-1-methylpyrrolidinium iodide (25 mg).

$^1$H NMR (300 MHz, DMSO-$d_6$) δ ppm 8.08 (d, 1H), 7.34-7.68 (m, 8H), 7.03-7.34 (m, 5H), 6.71 and 6.74 (s, 1H), 4.56 and 4.62 (s, 2H), 4.32-4.51 (m, 1H), 3.33-4.05 (m, 4H), 2.95 and 3.02 (s, 3H), 2.56-2.67 (m, 1H), 1.98-2.25 (m, 1H); LC-MS (ESI POS): 437.24 (M+).

Example 23

Preparation of 3-((bis(3-fluorophenyl)methoxy)carbonyl)-1-(2-oxo-2-phenylethyl)-1-azoniabicyclo[2.2.2]octane bromide (Compound 50)

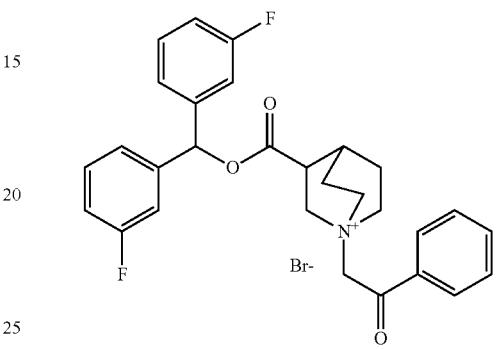

Bis(3-fluorophenyl)methyl quinuclidine-3-carboxylate (95 mg, 0.27 mmol, prepared as in example 4) and 2-bromo-1-phenylethanone (58.2 mg, 0.29 mmol) were dissolved in acetonitrile (5 ml) and stirred at room temperature overnight. The solvent was evaporated, and the resulting residue was purified by flash chromatography (DCM/MeOH=95/5 to 9/1) to obtain 3-((bis(3-fluorophenyl)methoxy)carbonyl)-1-(2-oxo-2-phenylethyl)-1-azoniabicyclo[2.2.2]octane bromide (110 mg, racemic mixture).

$^1$H NMR (300 MHz, DMSO-d6) δ ppm 7.92-8.06 (m, 2H), 7.71-7.82 (m, 1H), 7.56-7.69 (m, 2H), 7.30-7.52 (m, 6H), 7.10-7.22 (m, 2H), 6.93 (s, 1H), 5.24 (s, 2H), 4.03-4.21 (m, 1H), 3.91 (t, 1H), 3.59-3.82 (m, 4H), 3.45-3.59 (m, 1H), 2.64-2.71 (m, 1H), 2.02-2.25 (m, 2H), 1.83-2.02 (m, 1H), 1.40-1.64 (m, 1H);

LC-MS (ESI POS): 475.97 (M+).

The following compounds were prepared following the route described in Example 23 using the suitable alkylating agents instead of 2-bromo-1-phenylethanone. These compounds were obtained as a racemic mixture.

TABLE 5

| Compound | Structure | $^1$H-NMR | [M$^+$] |
|---|---|---|---|
| 51 | 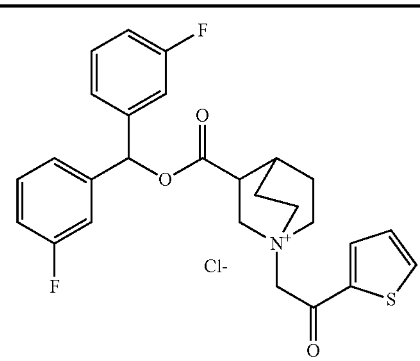 | (300 MHz, DMSO-d6) δ ppm 8.21 (dd, 1 H), 8.11 (dd, 1 H), 7.27-7.51 (m, 7 H), 7.11-7.20 (m, 2 H), 6.92 (s, 1 H), 5.13 (s, 2 H), 4.03-4.19 (m, 1 H), 3.85-4.00 (m, 1 H), 3.46-3.82 (m, 5 H), 2.63-2.72 (m, 1 H), 1.68-2.23 (m, 3 H), 1.38-1.68 (m, 1 H) | 482.29 |

TABLE 5-continued

| Compound | Structure | ¹H-NMR | [M⁺] |
|---|---|---|---|
| 52 | 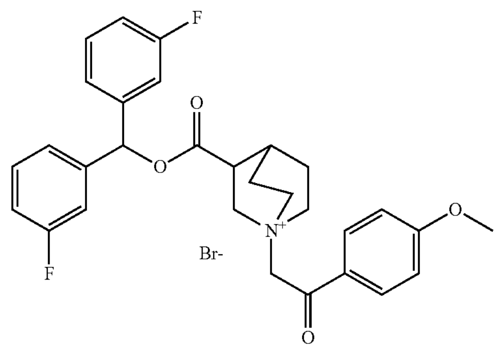 [SMILES: COc1ccc(C(=O)C[N+]23CCC(CC2)C(C(=O)OC(c2cccc(F)c2)c2cccc(F)c2)C3)cc1 ; [Br-]] | (300 MHz, DMSO-d6) δ ppm 7.90-8.05 (m, 2 H) 7.28-7.52 (m, 6 H) 7.07-7.23 (m, 4 H) 6.93 (s, 1 H) 5.17 (s, 2 H) 4.08-4.22 (m, 1 H) 3.88 (s, 3 H) 3.83-3.99 (m, 1 H) 3.47-3.82 (m, 5 H) 2.61-2.71 (m, 1 H) 2.02-2.22 (m, 2 H) 1.85-2.01 (m, 1 H) 1.45-1.64 (m, 1 H) | 506.1 |
| 53 | 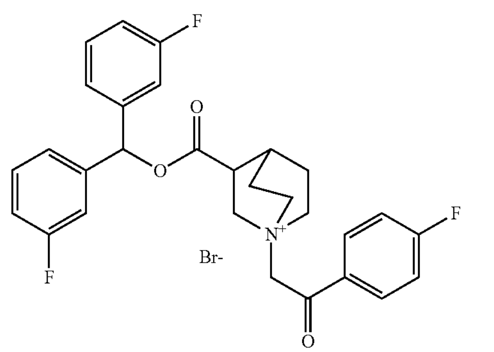 [SMILES: O=C(C[N+]12CCC(CC1)C(C(=O)OC(c1cccc(F)c1)c1cccc(F)c1)C2)c1ccc(F)cc1 ; [Br-]] | (300 MHz, DMSO-d6) δ ppm 8.01-8.17 (m, 2 H) 7.29-7.55 (m, 8 H) 7.10-7.22 (m, 2 H) 6.93 (s, 1 H) 5.16-5.28 (m, 2 H) 4.05-4.22 (m, 1 H) 3.82-3.99 (m, 1 H) 3.47-3.80 (m, 5 H) 2.64-2.71 (m, 1 H) 2.03-2.24 (m, 2 H) 1.84-2.03 (m, 1 H) 1.46-1.63 (m, 1 H) | 494.17 |

Example 24

Preparation of 3-(((bis(3-fluorophenyl)methoxy)carbonyl)-1-(2-oxo-2-p-tolylethyl)-1-azoniabicyclo[2.2.2]octane bromide (Compound 54)

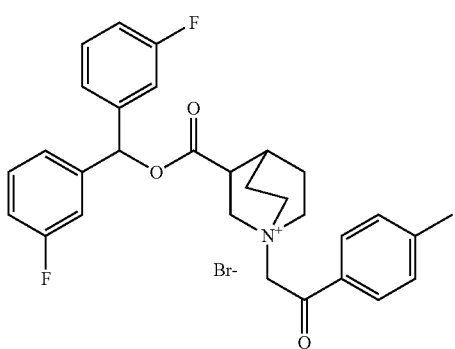 [SMILES: Cc1ccc(C(=O)C[N+]23CCC(CC2)C(C(=O)OC(c2cccc(F)c2)c2cccc(F)c2)C3)cc1 ; [Br-]]

Bis(3-fluorophenyl)methyl quinuclidine-3-carboxylate (95 mg, 0.27 mmol, prepared as in example 4) and 2-bromo-1-p-tolylethanone (62.3 mg, 0.29 mmol) were dissolved in acetonitrile (10 ml) and stirred at room temperature overnight. The solvent was evaporated, and the residue was triturated with Et₂O/EtOAc (1/1) and recovered by suction filtration to obtain 3-(((bis(3-fluorophenyl)methoxy)carbonyl)-1-(2-oxo-2-p-tolylethyl)-1-azoniabicyclo[2.2.2]octane bromide (117.6 mg, racemic mixture).

¹H NMR (300 MHz, DMSO-d6) δ ppm 7.82-7.97 (m, 2H), 7.33-7.49 (m, 6H), 7.30-7.37 (m, 2H), 7.10-7.23 (m, 2H), 6.93 (s, 1H), 5.20 (s, 2H), 4.13 (dd, 1H), 3.83-3.97 (m, 1H), 3.59-3.78 (m, 4H), 3.48-3.59 (m, 1H), 2.61-2.71 (m, 1H), 2.42 (s, 3H), 2.01-2.23 (m, 2H), 1.85-2.01 (m, 1H), 1.43-1.65 (m, 1H);

LC-MS (ESI POS): 490.15 (M+).

The following compounds were prepared following the route described in Example 24 using the suitable alkylating agents instead of 2-bromo-1-p-tolylethanone. These compounds were obtained as a racemic mixture.

TABLE 6
| Compound | Structure | ¹H-NMR | [M⁺] |
|---|---|---|---|
| 55 | 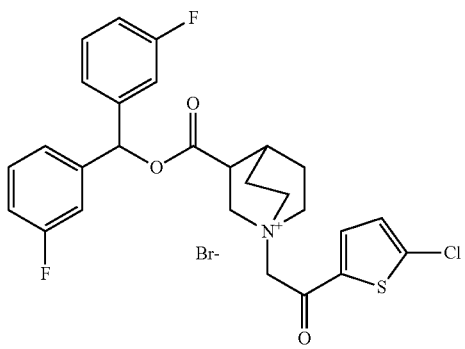 [SMILES: O=C(C[N+]12CCC(CC1)C(C(=O)OC(c1cccc(F)c1)c1cccc(F)c1)C2)c1ccc(Cl)s1 ; [Br-]] | (300 MHz, DMSO-d6) δ ppm 8.03 (dd, 1 H), 7.27-7.51 (m, 7 H), 7.16 (td, 2 H), 6.92 (s, 1 H), 4.92-5.27 (m, 2 H), 4.07 (dd, 1 H), 3.79-3.98 (m, 1 H), 3.45-3.79 (m, 5 H), 2.61-2.70 (m, 1 H), 1.98-2.23 (m, 2 H), 1.81-1.98 (m, 1 H), 1.41-1.62 (m, 1 H) | 516.11 |
| 56 | 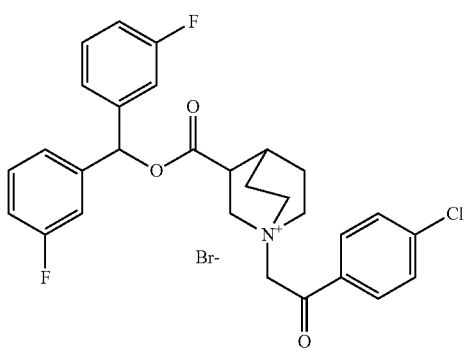 [SMILES: O=C(C[N+]12CCC(CC1)C(C(=O)OC(c1cccc(F)c1)c1cccc(F)c1)C2)c1ccc(Cl)cc1 ; [Br-]] | (300 MHz, DMSO-d6) δ ppm 7.94-8.07 (m, 2 H), 7.62-7.75 (m, 2 H), 7.28-7.52 (m, 6 H), 7.10-7.22 (m, 2 H), 6.93 (s, 1 H), 5.23 (s, 2 H), 4.12 (dd, 1 H), 3.89 (t, 1 H), 3.60-3.79 (m, 4 H), 3.49-3.59 (m, 1 H), 2.65-2.71 (m, 1 H), 2.01-2.23 (m, 2 H), 1.85-2.01 (m, 1 H), 1.42-1.62 (m, 1 H) | 510.13 |
| 57 | 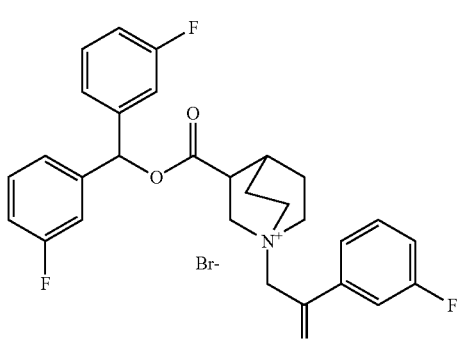 | (300 MHz, DMSO-d6) δ ppm 7.77-7.88 (m, 2 H) 7.57-7.74 (m, 2 H) 7.29-7.50 (m, 6 H) 7.10-7.21 (m, 2 H) 6.93 (s, 1 H) 5.22 (s, 2 H) 4.12 (dd, 1 H) 3.81-3.95 (m, 1 H) 3.49-3.77 (m, 5 H) 2.65-2.71 (m, 1 H) 2.03-2.24 (m, 2 H) 1.84-2.03 (m, 1 H) 1.43-1.63 (m, 1 H) | 494.18 |
| 58 | 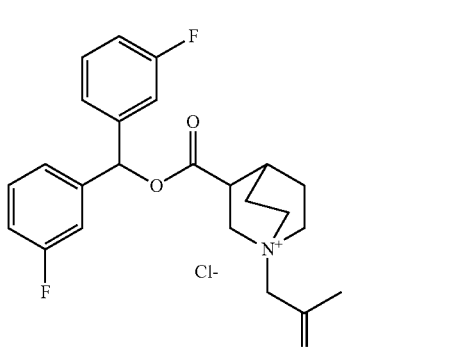 | (300 MHz, DMSO-d6) δ ppm 7.43 (td, 2 H), 7.36-7.41 (m, 2 H), 7.29-7.35 (m, 2 H), 7.15 (td, 2 H), 6.91 (s, 1 H), 4.56 (s, 2 H), 3.96 (dd, 1 H), 3.77 (t, 1 H), 3.43-3.66 (m, 5 H), 2.59-2.68 (m, 1 H), 2.15 (s, 3 H), 1.96-2.12 (m, 2 H), 1.73-1.96 (m, 1 H), 1.36-1.56 (m, 1 H) | 414.1 |

Example 25

Preparation of 3-((bis(3-fluorophenyl)methoxy)carbonyl)-1-(2-tert-butoxy-2-oxoethyl)-1-azoniabicyclo[2.2.2]octane chloride (Compound 59)

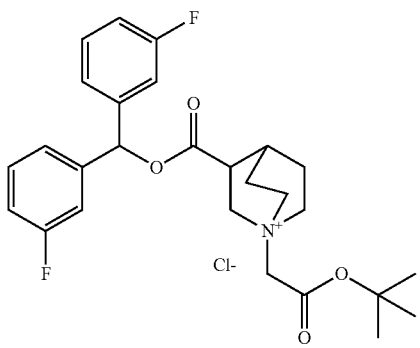 [SMILES: CC(C)(C)OC(=O)C[N+]12CCC(CC1)C(C(=O)OC(c1cccc(F)c1)c1cccc(F)c1)C2 ; [Cl-]]

Bis(3-fluorophenyl)methyl quinuclidine-3-carboxylate (70 mg, 0.20 mmol, prepared as in example 4) and tert-butyl 2-chloroacetate (31 μl, 0.21 mmol) were dissolved in acetonitrile (3 ml) and stirred at room temperature overnight. Tert-butyl 2-chloroacetate (28 μl, 0.20 mmol) was added again, and the mixture was stirred for additional 24 hours. Acetonitrile was evaporated, and the resulting crude compound was triturated from Et$_2$O and filtered to obtain 3-((bis(3-fluorophenyl)methoxy)carbonyl)-1-(2-tert-butoxy-2-oxoethyl)-1-azoniabicyclo[2.2.2]octane chloride (42.4 mg, racemic mixture).

$^1$H NMR (300 MHz, DMSO-d6) δ ppm 7.26-7.56 (m, 6H), 7.09-7.23 (m, 2H), 6.91 (s, 1H), 4.31 (s, 2H), 4.03 (dd, 1H), 3.80 (t, 1H), 3.38-3.71 (m, 5H), 2.59-2.69 (m, 1H), 1.77-2.17 (m, 4H), 1.48 (s, 9H);

LC-MS (ESI POS): 472.19 (M+).

Example 26

Preparation of 3-((bis(3-fluorophenyl)methoxy)carbonyl)-1-(2-oxo-2-(pyridin-2-yl)ethyl)-1-azoniabicyclo[2.2.2]octane 2,2,2-trifluoroacetate (Compound 60)

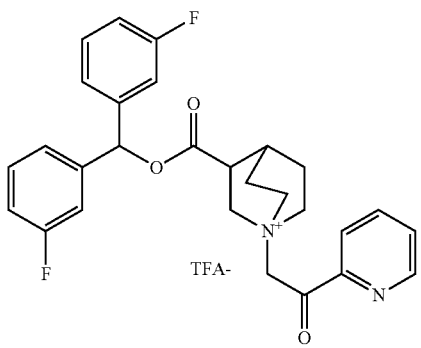 [SMILES: O=C(C[N+]12CCC(CC1)C(C(=O)OC(c1cccc(F)c1)c1cccc(F)c1)C2)c1ccccn1 ; "TFA-"]

Bis(3-fluorophenyl)methyl quinuclidine-3-carboxylate (70 mg, 0.20 mmol, prepared as in example 4) and 2-bromo-1-(pyridin-2-yl)ethanone hydrobromide (60.5 mg, 0.21 mmol) were suspended in acetonitrile (5 ml) and stirred at room temperature for 16 hours. TEA (27 μl, 0.20 mmol) was added, and the resulting clear solution was stirred at room temperature overnight. The volatiles were evaporated, and the residue was first purified by flash chromatography (DCM/MeOH=9/1) and then by preparative HPLC to obtain 3-((bis(3-fluorophenyl)methoxy)carbonyl)-1-(2-oxo-2-(pyridin-2-yl)ethyl)-1-azoniabicyclo[2.2.2]octane 2,2,2-trifluoroacetate (60.3 mg, racemic mixture).

$^1$H NMR (300 MHz, DMSO-d6) δ ppm 8.77 (m, 1H) 7.99-8.21 (m, 2H) 7.68-7.89 (m, 1H) 7.27-7.56 (m, 6H) 7.04-7.25 (m, 2H) 6.93 (s, 1H) 5.32 (s, 2H) 4.17 (m, 1H) 3.94 (t, 1H) 3.71 (m, 4H) 3.54 (t, 1H) 2.61-2.71 (m, 1H) 2.02-2.24 (m, 2H) 1.83-2.01 (m, 1H) 1.46-1.66 (m, 1H);

LC-MS (ESI POS): 477.08 (M+).

Example 27

Preparation of 3-((bis(3-fluorophenyl)methoxy)carbonyl)-1-(2-(3-(ethoxycarbonyl)isoxazol-5-yl)-2-oxoethyl)-1-azoniabicyclo[2.2.2]octane bromide (Compound 61)

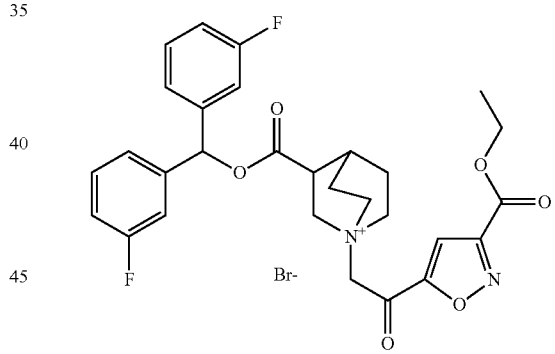

Bis(3-fluorophenyl)methyl quinuclidine-3-carboxylate (86 mg, 0.24 mmol, prepared as in example 4) and ethyl 5-(2-bromoacetyl)isoxazole-3-carboxylate (69.4 mg, 0.26 mmol) were dissolved in acetonitrile (3 ml) and stirred at room temperature overnight. The precipitated was recovered by suction filtration to obtain 3-((bis(3-fluorophenyl)methoxy)carbonyl)-1-(2-(3-(ethoxycarbonyl)isoxazol-5-yl)-2-oxoethyl)-1-azoniabicyclo[2.2.2]octane bromide (26 mg, racemic mixture).

$^1$H NMR (300 MHz, DMSO-d6) δ ppm 7.90 (s, 1H), 7.23-7.52 (m, 6H), 7.16 (td, 2H), 6.92 (s, 1H), 5.06 (s, 2H), 4.43 (q, 2H), 4.00-4.16 (m, 1H), 3.81-3.97 (m, 1H), 3.48-3.80 (m, 5H), 2.65-2.71 (m, 1H), 2.01-2.24 (m, 2H), 1.78-2.01 (m, 1H), 1.45-1.65 (m, 1H), 1.35 (t, 3H);

LC-MS (ESI POS): 539.16 (M+).

Example 28

Preparation of 3-((bis(3-fluorophenyl)methoxy)carbonyl)-1-(2-(2-fluorophenyl)-2-oxoethyl)-1-azoniabicyclo[2.2.2]octane bromide (Compound 62)

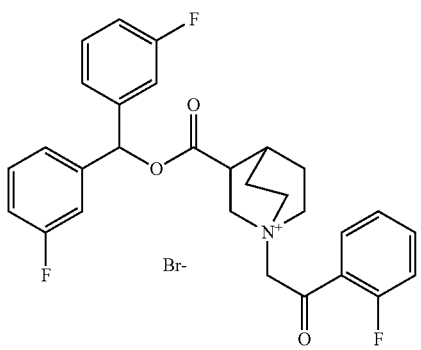 [SMILES: O=C(C[N+]12CCC(CC1)C(C(=O)OC(c1cccc(F)c1)c1cccc(F)c1)C2)c1ccccc1F ; [Br-]]

Bis(3-fluorophenyl)methyl quinuclidine-3-carboxylate (90 mg, 0.25 mmol, prepared as in example 4) and 2-bromo-1-(2-fluorophenyl)ethanone (65.6 mg, 0.30 mmol) were dissolved in acetonitrile (4 ml) and stirred at room temperature overnight. Acetonitrile was evaporated, and the residue was triturated with Et₂O and filtered to obtain 3-((bis(3-fluorophenyl)methoxy)-carbonyl)-1-(2-(2-fluorophenyl)-2-oxoethyl)-1-azoniabicyclo[2.2.2]octane bromide (51.3 mg, racemic mixture).

¹H NMR (300 MHz, DMSO-d6) δ ppm 7.97 (td, 1H), 7.72-7.87 (m, 1H), 7.30-7.55 (m, 8H), 7.10-7.23 (m, 2H), 6.93 (s, 1H), 5.06 (d, 2H), 4.14 (dd, 1H), 3.92 (t, 1H), 3.60-3.82 (m, 4H), 3.49-3.59 (m, 1H), 2.64-2.71 (m, 1H), 2.01-2.19 (m, 2H), 1.82-2.01 (m, 1H), 1.41-1.70 (m, 1H);

LC-MS (ESI POS): 494.10 (M+).

The following compounds were prepared following the route described in Example 28 using the suitable alkylating agents instead of 2-bromo-1-(2-fluorophenyl)ethanone. These compounds were obtained as a racemic mixture.

TABLE 7

| Compound | Structure | ¹H-NMR | [M⁺] |
|---|---|---|---|
| 63 | (structure: bis(3-fluorophenyl)methyl quinuclidine-3-carboxylate with N-substituted 2-oxo-2-(thiophen-3-yl)ethyl group, Br⁻) | (300 MHz, DMSO-d6) δ ppm 8.64 (dd, 1 H), 7.74 (dd, 1 H), 7.57 (dd, 1 H), 7.29-7.49 (m, 6 H), 7.16 (m, 2 H), 6.92 (s, 1 H), 5.09 (s, 2 H), 4.06-4.20 (m, 1 H), 3.82-3.97 (m, 1 H), 3.59-3.80 (m, 4 H), 3.47-3.59 (m, 1 H), 2.63-2.70 (m, 1 H), 2.02-2.25 (m, 2 H), 1.76-2.02 (m, 1 H), 1.46-1.67 (m, 1 H) | 482.1 |
| 64 | (structure: bis(3-fluorophenyl)methyl quinuclidine-3-carboxylate with N-substituted 2-(4-hydroxyphenyl)-2-oxoethyl group, Br⁻) | (300 MHz, DMSO-d6) δ ppm 10.69 (s, 1 H), 7.78-7.95 (m, 2 H), 7.29-7.49 (m, 6 H), 7.16 (td, 2 H), 6.81-6.98 (m, 3 H), 5.11 (s, 2 H), 4.03-4.21 (m, 1 H), 3.82-4.00 (m, 1 H), 3.59-3.82 (m, 4 H), 3.46-3.59 (m, 1 H), 2.62-2.70 (m, 1 H), 2.00-2.21 (m, 2 H), 1.79-1.98 (m, 1 H), 1.41-1.64 (m, 1 H) | 492.24 |

Example 29

Preparation of 1-(2-(benzo[b]thiophen-5-yl)-2-oxoethyl)-3-((bis(3-fluorophenyl)methoxy)carbonyl)-1-azoniabicyclo[2.2.2]octane 2,2,2-trifluoroacetate (Compound 65)

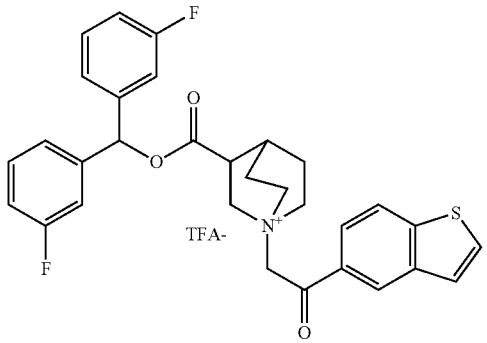

Bis(3-fluorophenyl)methyl quinuclidine-3-carboxylate (86 mg, 0.24 mmol, prepared as in example 4) and 1-(benzo[b]thiophen-5-yl)-2-bromoethanone (67.5 mg, 0.26 mmol) were dissolved in acetonitrile (3 ml) and stirred at room temperature overnight. Acetonitrile was evaporated, and the crude was first triturated with Et$_2$O and then purified by preparative HPLC to obtain 1-(2-(benzo[b]thiophen-5-yl)-2-oxoethyl)-3-((bis(3-fluorophenyl)methoxy)carbonyl)-1-azoniabicyclo[2.2.2]octane 2,2,2-trifluoroacetate (83 mg, racemic mixture).

$^1$H NMR (300 MHz, DMSO-d6) δ ppm 8.59 (d, 1H), 8.25 (d, 1H), 7.97 (d, 1H), 7.93 (dd, 1H), 7.66 (dd, 1H), 7.30-7.53 (m, 6H), 7.09-7.23 (m, 2H), 6.94 (s, 1H), 5.31 (s, 2H), 4.17 (dd, 1H), 3.94 (t, 1H), 3.62-3.84 (m, 4H), 3.47-3.62 (m, 1H), 2.66-2.73 (m, 1H), 2.02-2.24 (m, 2H), 1.88-2.04 (m, 1H), 1.40-1.69 (m, 1H);
LC-MS (ESI POS): 532.09 (M+).

Example 30

Preparation of 1-benzyl-3-((bis(3-fluorophenyemethoxy)carbonyl)-1-azoniabicyclo[2.2.2]octane bromide (Compound 66)

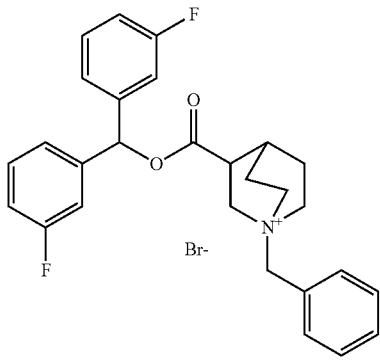 [SMILES: O=C(OC(c1cccc(F)c1)c1cccc(F)c1)C1C[N+]2(Cc3ccccc3)CCC1CC2 ; [Br-]]

To a solution of bis(3-fluorophenyl)methyl quinuclidine-3-carboxylate (90 mg, 0.25 mmol, prepared as in example 4) in EtOAc (3 ml), (bromomethyl)benzene (30.0 μl, 0.25 mmol) was added, and the reaction was stirred at room temperature overnight. The solvent was removed, and the crude was purified by flash chromatography (DCM/MeOH=95/5) to obtain 1-benzyl-3-((bis(3-fluorophenyl)methoxy)carbonyl)-1-azoniabicyclo[2.2.2]octane bromide (50 mg, racemic mixture).

$^1$H NMR (300 MHz, DMSO-d6) δ ppm 7.52 (s, 5H), 7.42 (td, 2H), 7.23-7.38 (m, 4H), 7.08-7.19 (m, 2H), 6.86 (s, 1H), 4.53 (s, 2H), 3.68-3.83 (m, 1H), 3.56-3.68 (m, 1H), 3.35-3.53 (m, 4H), 3.13-3.27 (m, 1H), 2.57-2.65 (m, 1H), 1.91-2.18 (m, 2H), 1.68-1.91 (m, 1H), 1.36-1.57 (m, 1H);
LC-MS (ESI POS): 448.23 (M+).

Example 31

Preparation of 3-((1,2-diphenylethoxy)carbonyl)-1-(2-oxo-2-(thiophen-2-yl)ethyl)-1-azoniabicyclo[2.2.2]octane 2,2,2-trifluoroacetate (Compound 67)

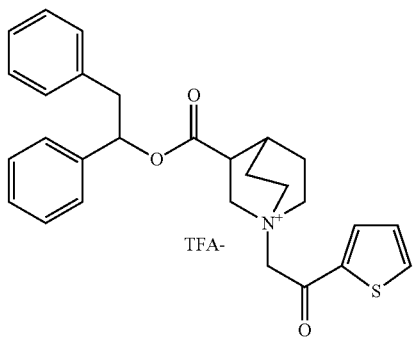

1,2-Diphenylethyl quinuclidine-3-carboxylate (68 mg, 0.20 mmol, prepared as in example 5) and 2-chloro-1-(thiophen-2-yl)ethanone (35.8 mg, 0.22 mmol) were dissolved in acetonitrile (4 ml) and stirred at room temperature for 64 hours. Acetonitrile was evaporated and the resulting crude was first purified by flash chromatography (DCM/MeOH=9/1) and then by preparative HPLC to obtain 3-((1,2-diphenylethoxy)carbonyl)-1-(2-oxo-2-(thiophen-2-yl)ethyl)-1-azoniabicyclo[2.2.2]octane 2,2,2-trifluoroacetate (44 mg, racemic mixture).

$^1$H NMR (300 MHz, DMSO-d6) δ ppm 8.14-8.26 (m, 1H), 7.95-8.12 (m, 1H), 7.10-7.59 (m, 11H), 6.02 and 6.10 (dd, 1H), 5.03 and 5.05 (s, 2H), 3.90-4.06 (m, 1H), 3.59-3.89 (m, 5H), 2.98-3.33 (m, 3H), 1.45-2.45 (m, 4H), 0.83-1.31 (m, 1H);
LC-MS (ESI POS): 460.18 (M+).

Example 32

Preparation of 3-((bis(4-chlorophenyl)methoxy)carbonyl)-1-(2-oxo-2-(thiophen-2-yl)ethyl)-1-azoniabicyclo[2.2.2]octane chloride (Compound 68)

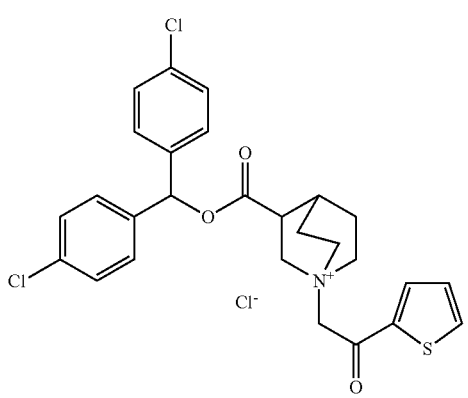 [SMILES: O=C(C[N+]12CCC(CC1)C(C(=O)OC(c1ccc(Cl)cc1)c1ccc(Cl)cc1)C2)c1cccs1 ; [Cl-]]

To a solution of bis(4-chlorophenyl)methyl quinuclidine-3-carboxylate (45 mg, 0.11 mmol, prepared as in example 6) in EtOAc (1.6 ml), 2-chloro-1-(thiophen-2-yl)ethanone (20.0 mg, 0.13 mmol) was added. The reaction was stirred at room temperature for 16 hours. Solvent was removed, and the crude was purified by preparative HPLC to afford 3-((bis(4-chlorophenyl)methoxy)-carbonyl)-1-(2-oxo-2-(thiophen-2-yl)ethyl)-1-azoniabicyclo[2.2.2]octane chloride (16 mg, racemic mixture).

$^1$H NMR (300 MHz, DMSO-d6) δ ppm 8.21 (dd, 1H), 8.09 (dd, 1H), 7.40-7.57 (m, 8H), 7.35 (dd, 1H), 6.92 (s, 1H), 5.09 (s, 2H), 4.01-4.16 (m, 1H), 3.80-4.00 (m, 1H), 3.54-3.78 (m, 3H), 3.47-3.54 (m, 2H), 2.59-2.69 (m, 1H), 2.01-2.21 (m, 2H), 1.82-2.01 (m, 1H), 1.41-1.64 (m, 1H);

LC-MS (ESI POS): 514.02 (M+).

Example 33

Preparation of 3-((bis(4-fluorophenyl)methoxy)carbonyl)-1-(2-oxo-2-(thiophen-2-yl)ethyl)-1-azoniabicyclo[2.2.2]octane 2,2,2-trifluoroacetate (Compound 70)

1. Preparation of bis(4-fluorophenyl)methyl quinuclidine-3-carboxylate (Compound 69)

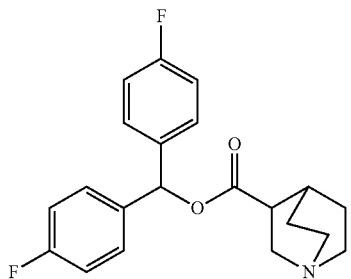 [SMILES: O=C(OC(c1ccc(F)cc1)c1ccc(F)cc1)C1CN2CCC1CC2]

Quinuclidine-3-carboxylic acid hydrochloride (96 mg, 0.50 mmol), EDC (131 mg, 0.68 mmol), and HOBT (104 mg, 0.68 mmol) were suspended in dry DMF (5 ml). Bis(4-fluorophenyl)methanol (100 mg, 0.45 mmol) and DIPEA (278 μl, 1.59 mmol) were added, and the mixture was stirred at room temperature for 24 hours. Then, quinuclidine-3-carboxylic acid hydrochloride (43.5 mg, 0.23 mmol), EDC (43.5 mg, 0.23 mmol), HOBT (34.8 mg, 0.23 mmol), and DIPEA (79 μl, 0.45 mmol) were added again and stirring was continued for 4 days. Finally quinuclidine-3-carboxylic acid hydrochloride (43.5 mg, 0.23 mmol), EDC (43.5 mg, 0.23 mmol), and DIPEA (79 μl, 0.45 mmol) were added, and the suspension was stirred for additional 24 hours. The reaction was portioned between sat. NaHCO$_3$ and Et$_2$O, and the organic layer was separated, washed again with sat. NaHCO$_3$ and then brine. The organic phase was dried over Na$_2$SO$_4$, filtered, and evaporated to afford bis(4-fluorophenyl)methyl quinuclidine-3-carboxylate (51 mg, racemic mixture). The compound was used as such in the next step.

2. Preparation of 3-((bis(4-fluorophenyemethoxy)carbonyl)-1-(2-oxo-2-(thiophen-2-yl)ethyl)-1-azoniabicyclo[2.2.2]octane 2,2,2-trifluoroacetate (Compound 70)

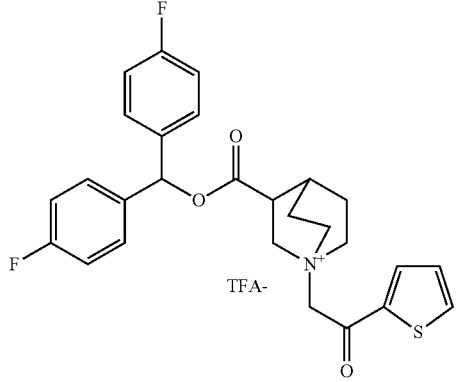

To a solution of bis(4-fluorophenyl)methyl quinuclidine-3-carboxylate (51 mg, 0.14 mmol) in acetonitrile (5 ml), 2-bromo-1-(thiophen-2-yl)ethanone (32.2 mg, 0.16 mmol) was added, and the reaction was stirred at room temperature for 15 hours. The solvent was evaporated, and the resulting crude was purified by preparative HPLC to obtain 3-((bis(4-fluorophenyl)methoxy)-carbonyl)-1-(2-oxo-2-(thiophen-2-yl)ethyl)-1-azoniabicyclo[2.2.2]octane 2,2,2-trifluoroacetate (73.4 mg, racemic mixture).

$^1$H NMR (300 MHz, DMSO-d6) δ ppm 8.21 (dd, 1H) 8.08 (dd, 1H) 7.43-7.60 (m, 4H) 7.35 (dd, 1H) 7.15-7.28 (m, 4H) 6.93 (s, 1H) 5.08 (s, 2H) 3.99-4.17 (m, 1H) 3.79-3.94 (m, 1H) 3.62-3.77 (m, 5H) 2.56-2.66 (m, 1H) 1.77-2.20 (m, 3H) 1.31-1.67 (m, 1H);

LC-MS (ESI POS): 482.17 (M+).

Example 34

Preparation of 3-(benzhydryloxycarbonyl)-1-(2-oxo-2-(thiophen-2-yl)ethyl)-1-azoniabicyclo[2.2.2]octane 2,2,2-trifluoroacetate (Compound 72)

1. Preparation of benzhydryl quinuclidine-3-carboxylate (Compound 71)

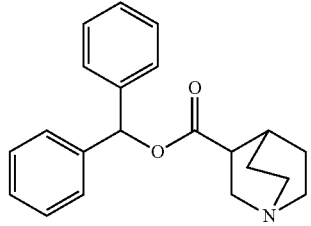 [SMILES: O=C(OC(c1ccccc1)c1ccccc1)C1CN2CCC1CC2]

Quinuclidine-3-carboxylic acid hydrochloride (114 mg, 0.60 mmol), EDC (156 mg, 0.81 mmol), and HOBT (125 mg, 0.81 mmol) were suspended in dry DMF (5 ml). Diphenylmethanol (100 mg, 0.54 mmol) and DIPEA (332 μl, 1.90 mmol) were added, and the mixture was stirred at room temperature for 24 hours. Quinuclidine-3-carboxylic acid hydrochloride (52.0 mg, 0.27 mmol), EDC (52.0 mg, 0.27 mmol), and HOBT (41.6 mg, 0.27 mmol) followed by DIPEA (95 μl, 0.54 mmol) were added again, and the mixture was stirred for 4 days. The reaction was then portioned between sat. NaHCO$_3$ and Et$_2$O. The organic layer was separated, washed again with sat. NaHCO$_3$, water and brine, dried over Na$_2$SO$_4$, filtered, and evaporated to afford benzhydryl quinuclidine-3-carboxylate (54 mg, racemic mixture). The compound was used as such in the next step.

2. Preparation of 3-(benzhydryloxycarbonyl)-1-(2-oxo-2-(thiophen-2-yl)ethyl)-1-azoniabicyclo[2.2.2]octane 2,2,2-trifluoroacetate (Compound 72)

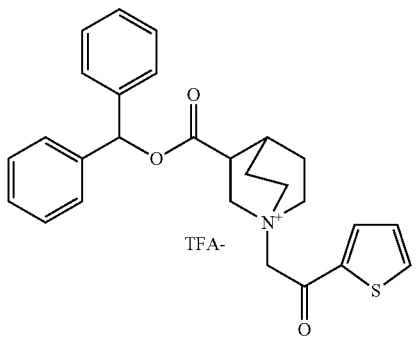

To a solution of benzhydryl quinuclidine-3-carboxylate (54 mg, 0.17 mmol) in acetonitrile (5 ml), 2-bromo-1-(thiophen-2-yl)ethanone (37.9 mg, 0.18 mmol) was added, and the reaction was stirred at room temperature for 15 hours. The solvent was evaporated, and the resulting crude was first purified by preparative HPLC and then by flash chromatography (DCM/MeOH=95/5 to 9/1) to obtain 3-(benzhydryloxycarbonyl)-1-(2-oxo-2-(thiophen-2-yl)ethyl)-1-azoniabicyclo[2.2.2]octane 2,2,2-trifluoroacetate (53.8 mg, racemic mixture).

$^1$H NMR (300 MHz, DMSO-d6) δ ppm 8.20 (dd, 1H) 8.09 (dd, 1H) 7.23-7.52 (m, 11H) 6.90 (s, 1H) 5.09 (s, 2H) 4.04-4.16 (m, 1H) 3.79-3.95 (m, 1H) 3.56-3.79 (m, 4H) 3.33-3.56 (m, 1H) 2.57-2.70 (m, 1H) 1.99-2.24 (m, 2H) 1.76-1.99 (m, 1H) 1.40-1.68 (m, 1H);

LC-MS (ESI POS): 446.15 (M+).

Example 35

Preparation of 3-(((4-methoxyphenyl)(phenyl)methoxy)carbonyl)-1-(2-oxo-2-(thiophen-2-yl)ethyl)-1-azoniabicyclo[2.2.2]octane chloride (Compound 74)

1. Preparation of (4-methoxyphenyl)(phenyl)methyl quinuclidine-3-carboxylate (Compound 73)

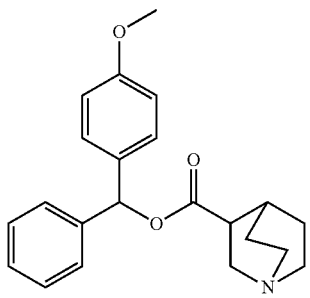 [SMILES: COc1ccc(C(OC(=O)C2CN3CCC2CC3)c2ccccc2)cc1]

Quinuclidine-3-carboxylic acid hydrochloride (150 mg, 0.78 mmol), EDC (225 mg, 1.17 mmol), and HOBT (180 mg, 1.17 mmol) were dissolved in dry THF (7.5 ml). (4-Methoxyphenyl)(phenyl)methanol (184 mg, 0.86 mmol) and TEA (382 μl, 2.74 mmol) were added, and the resulting reaction was stirred at room temperature for four days. THF was removed under vacuum, and the crude residue was partitioned between EtOAc and water. The organic phase was washed with a sat. NaHCO$_3$, dried over Na$_2$SO$_4$, filtered, and evaporated. The crude was purified by flash chromatography (EtOAc/MeOH=8/2 to EtOAc/MeOH=7:3+1% NH$_4$OH) to give (4-methoxyphenyl)(phenyl)methyl quinuclidine-3-carboxylate (37 mg, mixture of diastereoisomers). The compound was used as such in the next step.

2. Preparation of 3-(((4-methoxyphenyl)-(phenyl)methoxy)-carbonyl)-1-(2-oxo-2-(thiophen-2-yl)ethyl)-1-azoniabicyclo[2.2.2]octane chloride (Compound 74)

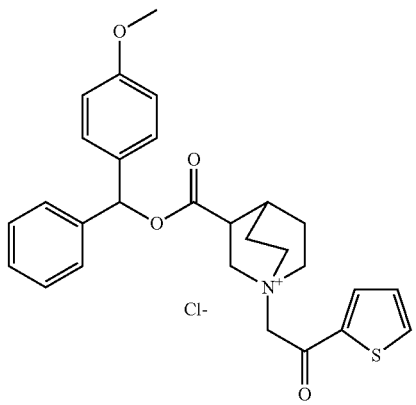 [SMILES: COc1ccc(C(OC(=O)C2C[N+]3(CC(=O)c4cccs4)CCC2CC3)c2ccccc2)cc1 ; [Cl-]]

To a solution of (4-methoxyphenyl)(phenyl)methyl quinuclidine-3-carboxylate (37 mg, 0.10 mmol) in EtOAc (1.5 ml), 2-chloro-1-(thiophen-2-yl)ethanone (19 mg, 0.12 mmol) was added. Acetonitrile was added until complete dissolution, and the reaction was stirred at room temperature overnight. The organic solvents were removed under vacuum, and the residue was purified by flash chromatography (DCM/MeOH=9/1) to obtain 3-(((4-methoxyphenyl)(phenyl)methoxy)carbonyl)-1-(2-oxo-2-(thiophen-2-yl)ethyl)-1-azoniabicyclo[2.2.2]octane chloride (16 mg, mixture of diastereoisomers).

$^1$H NMR (300 MHz, DMSO-d6) δ ppm 8.21 (dd, 1H), 8.09 (dd, 1H), 7.24-7.51 (m, 8H), 6.89-6.98 (m, 2H), 6.86 (s, 1H), 5.09 (s, 2H), 4.02-4.20 (m, 1H), 3.80-3.94 (m, 1H), 3.74 (s, 3H), 3.36-3.73 (m, 5H), 2.56-2.66 (m, 1H), 1.79-2.23 (m, 3H), 1.36-1.67 (m, 1H);

LC-MS (ESI POS): 476.17 (M+).

Example 36

Preparation of 3-(((2-chlorophenyl)(4-chlorophenyl)methoxy)-carbonyl)-1-(2-oxo-2-(thiophen-3-yl)ethyl)-1-azoniabicyclo[2.2.2]octane 2,2,2-trifluoroacetate (Compound 76)

1. Preparation of (2-chlorophenyl)(4-chlorophenyl)methyl quinuclidine-3-carboxylate (Compound 75)

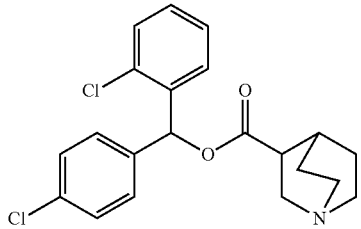 [SMILES: O=C(OC(c1ccc(Cl)cc1)c1ccccc1Cl)C1CN2CCC1CC2]

Quinuclidine-3-carboxylic acid hydrochloride (0.1 g, 0.52 mmol), EDC (150 mg, 0.78 mmol), and HOBT (120 mg, 0.78 mmol) were dissolved in dry THF (3 ml). (2-Chlorophenyl)(4-chlorophenyl)methanol (145 mg, 0.57 mmol) was dissolved in dry THF (2 ml) and then added to the reaction mixture. Triethylamine (253 μl, 1.83 mmol) was added, and the resulting reaction was stirred at room temperature overnight. The mixture was evaporated, and the crude was taken up with EtOAc and washed with water and brine. The organic phase was separated, dried (sodium sulfate), filtered, and evaporated under vacuum. The crude was purified by flash chromatography (DCM/MeOH=95/5) to afford (2-chlorophenyl)(4-chlorophenyl)methyl quinuclidine-3-carboxylate (40 mg, mixture of diastereoisomers). The compound was used as such in the next step.

2. Preparation of 3-(((2-chlorophenyl)(4-chlorophenyl)methoxy)-carbonyl)-1-(2-oxo-2-(thiophen-3-yl)ethyl)-1-azoniabicyclo[2.2.2]octane 2,2,2-trifluoroacetate (Compound 76)

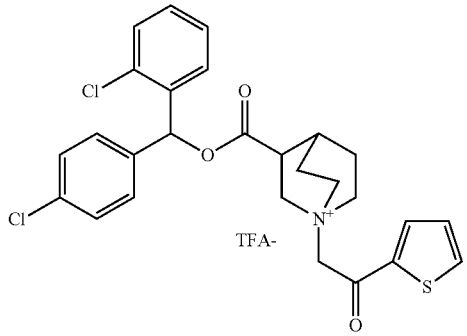

To a solution of (2-chlorophenyl)(4-chlorophenyl)methyl quinuclidine-3-carboxylate (40 mg, 0.10 mmol) in EtOAc (1.5 ml), 2-bromo-1-(thiophen-3-yl)ethanone (23 mg, 0.11 mmol) was added. Acetonitrile was added until complete dissolution, and the reaction was stirred at room temperature overnight. The organic solvents were evaporated under vacuum, and the crude residue was purified by preparative HPLC to obtain 3-(((2-chlorophenyl)(4-chlorophenyl)methoxy)carbonyl)-1-(2-oxo-2-(thiophen-3-yl)ethyl)-1-azoniabicyclo[2.2.2]octane 2,2,2-trifluoroacetate (28.6 mg, mixture of diastereoisomers).

$^1$H NMR (300 MHz, DMSO-d6) δ ppm 8.62 (dd, 1H) 7.74 (dd, 1H) 7.56 (dd, 1H) 7.35-7.66 (m, 8H) 7.12 (s, 1H) 5.05 (s, 2H) 4.09 (dd, 1H) 3.87 (t, 1H) 3.59-3.75 (m, 5H) 2.54-2.64 (m, 1H) 1.86-2.20 (m, 3H) 1.43-1.73 (m, 1H);

LC-MS (ESI POS): 514.08 (M+).

Example 37

Preparation of 3-(((3,4-difluorophenyl)(phenyl)methoxy)carbonyl)-1-(2-oxo-2-(thiophen-2-yl)ethyl)-1-azoniabicyclo[2.2.2]octane chloride (Compound 78)

1—Preparation of (3,4-difluorophenyl)(phenyl)methyl quinuclidine-3-carboxylate (Compound 77)

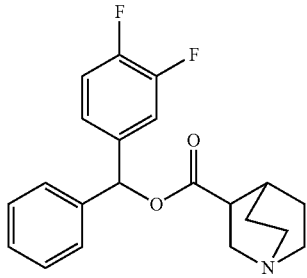 [SMILES: O=C(OC(c1ccccc1)c1ccc(F)c(F)c1)C1CN2CCC1CC2]

Quinuclidine-3-carboxylic acid hydrochloride (80 mg, 0.42 mmol), EDC (120 mg, 0.62 mmol), and HOBT (96 mg, 0.62 mmol) were dissolved in dry THF (3 ml). (3,4-Difluorophenyl)(phenyl)methanol (101 mg, 0.46 mmol) was dissolved in dry THF (2 ml) and then added to the reaction mixture. Triethylamine (203 µl, 1.46 mmol) was finally added, and the resulting reaction was stirred at room temperature overnight. The volatiles were evaporated, and the crude was taken up with EtOAc and washed with water and then with sat. NaHCO$_3$. The organic phase was dried over sodium sulfate, filtered, and evaporated under vacuum. The crude was purified by flash chromatography (DCM/MeOH=9/1) to obtain (3,4-difluorophenyl)(phenyl)-methyl quinuclidine-3-carboxylate (65 mg, mixture of diastereoisomers).

2. Preparation of 3(((3,4-difluorophenyl)(phenyl)-methoxy)carbonyl)-1-(2-oxo-2-(thiophen-2-yl)ethyl)-1-azoniabicyclo-[2.2.2]octane chloride (Compound 78)

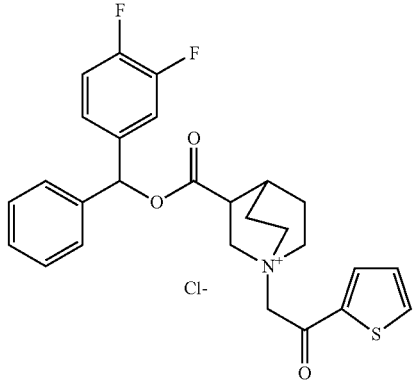 [SMILES: O=C(C[N+]12CCC(CC1)C(C(=O)OC(c1ccccc1)c1ccc(F)c(F)c1)C2)c1cccs1 ; [Cl-]]

To a solution of (3,4-difluorophenyl)(phenyl)methyl quinuclidine-3-carboxylate (65 mg, 0.18 mmol) in ethyl acetate (3 ml), 2-chloro-1-(thiophen-2-yl)ethanone (29.2 mg, 0.18 mmol) was added, and the mixture was stirred at room temperature overnight. The solvent was removed under vacuum, and the residue was taken up with diethyl ether and filtered to give 3-(((3,4-difluorophenyl)(phenyl)methoxy)carbonyl)-1-(2-oxo-2-(thiophen-2-yl)ethyl)-1-azoniabicyclo[2.2.2]octane chloride (20 mg, mixture of diastereoisomers).

$^1$H NMR (300 MHz, DMSO-d6) δ ppm 8.21 (d, 1H), 8.11 (d, 1H), 7.52-7.71 (m, 1H), 7.18-7.52 (m, 8H), 6.90 (s, 1H), 5.14 (s, 2H), 3.98-4.19 (m, 1H), 3.82-3.98 (m, 1H), 3.41-3.82 (m, 5H), 2.59-2.69 (m, 1H), 1.40-2.21 (m, 4H);

LC-MS (ESI POS): 482.17 (M+).

Example 38

Preparation of 3-((3-fluorobenzyloxy)carbonyl)-1-(2-oxo-2-(thiophen-2-yl)ethyl)-1-azoniabicyclo[2.2.2]octane 2,2,2-trifluoroacetate (Compound 80)

1. Preparation of 3-fluorobenzyl quinuclidine-3-carboxylate (Compound 79)

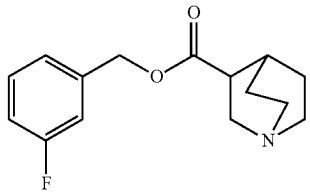 [SMILES: O=C(OCc1cccc(F)c1)C1CN2CCC1CC2]

Quinuclidine-3-carboxylic acid hydrochloride (95 mg, 0.50 mmol), EDC (143 mg, 0.74 mmol), HOBT (114 mg, 0.74 mmol), and triethylamine (242 µl, 1.73 mmol) were dissolved in dry THF (5 ml). (3-Fluorophenyl)methanol (68.8 mg, 0.54 mmol) was dissolved in dry THF (2 ml) and added to the reaction mixture. The resulting reaction was stirred at room temperature overnight. The volatiles were evaporated, and the crude was taken up with EtOAc and washed with water and then with sat. NaHCO$_3$. The organic phase was separated, dried over sodium sulfate, filtered, and evaporated under vacuum to obtain 3-fluorobenzyl quinuclidine-3-carboxylate (120 mg, racemic mixture). The compound was used in the next step without any further purification.

2. Preparation of 3-((3-fluorobenzyloxy)carbonyl)-1-(2-oxo-2-(thiophen-2-yl)ethyl)-1-azoniabicyclo[2.2.2]octane 2,2,2-trifluoroacetate (Compound 80)

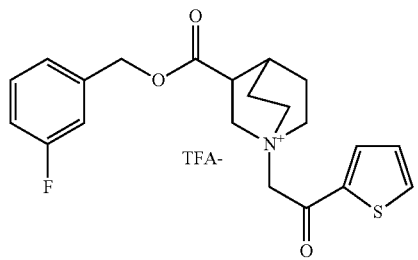 [SMILES: O=C(C[N+]12CCC(CC1)C(C(=O)OCc1cccc(F)c1)C2)c1cccs1]

2-Chloro-1-(thiophen-2-yl)ethanone (67 mg, 0.42 mmol) was added to a solution of 3-fluorobenzyl quinuclidine-3-carboxylate (100 mg, 0.38 mmol) in a mixture of EtOAc (1.2 ml) with some drops of DMF. The reaction was stirred at room temperature overnight. Then a second portion of 2-chloro-1-(thiophen-2-yl)ethanone (67 mg, 0.42 mmol) was added, and the reaction stirred at room temperature for 3 hours. The solvent was removed, and the residue was dissolved in acetonitrile and heated under microwave irradiation at 100° C. for 2 hours. Acetonitrile was evaporated and the crude was triturated with Et$_2$O and then purified by preparative HPLC to obtain 3-((3-fluorobenzyloxy)carbonyl)-1-(2-oxo-2-(thiophen-2-yl)ethyl)-1-azoniabicyclo-[2.2.2]octane 2,2,2-trifluoroacetate (70 mg, racemic mixture).

$^1$H NMR (300 MHz, DMSO-d6) δ ppm 8.21 (dd, 1H), 8.09 (dd, 1H), 7.45 (td, 1H), 7.36 (dd, 1H), 7.24-7.30 (m, 2H), 7.11-7.23 (m, 1H), 5.26 (d, 1H), 5.20 (d, 1H), 5.10 (s, 2H), 4.10 (ddd, 1H), 3.81-3.93 (m, 1H), 3.57-3.76 (m, 4H), 3.31-3.49 (m, 1H), 2.54-2.61 (m, 1H), 1.85-2.18 (m, 3H), 1.63-1.85 (m, 1H);

LC-MS (ESI POS): 388.27 (M+).

Example 39

Preparation of 3-((9H-fluoren-9-yloxy)carbonyl)-1-(2-oxo-2-(thiophen-2-yl)ethyl)-1-azoniabicyclo[2.2.2]octane 2,2,2-trifluoroacetate (Compound 82)

1. Preparation of 9H-fluoren-9-yl quinuclidine-3-carboxylate (Compound 81)

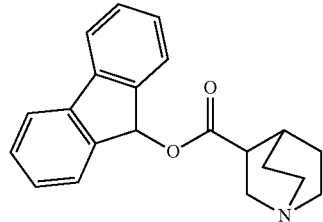 [SMILES: O=C(OC1c2ccccc2-c2ccccc21)C1CN2CCC1CC2]

Quinuclidine-3-carboxylic acid hydrochloride (95 mg, 0.50 mmol), EDC (143 mg, 0.74 mmol), triethylamine (242 μl, 1.73 mmol), and HOBT (114 mg, 0.74 mmol) were dissolved in dry THF (5 ml). 9H-fluoren-9-ol (99 mg, 0.54 mmol) was dissolved in dry THF (2 ml) and then added to the reaction mixture. The resulting suspension was stirred at room temperature overnight. The mixture was evaporated, and the crude taken up with EtOAc and washed sequentially with water and sat. NaHCO$_3$. The organic phase was dried over sodium sulfate, filtered. and evaporated under vacuum. The crude was purified by flash chromatography (DCM/MeOH=9/1) to afford 9H-fluoren-9-yl quinuclidine-3-carboxylate (102 mg, racemic mixture).

2. Preparation of 3-((9H-fluoren-9-yloxy)carbonyl)-1-(2-oxo-2-(thiophen-2-yl)ethyl)-1-azoniabicyclo[2.2.2]octane 2,2,2-trifluoroacetate (Compound 82)

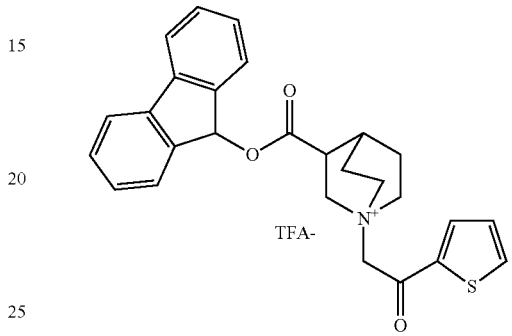

2-Chloro-1-(thiophen-2-yl)ethanone (55 mg, 0.344 mmol) was added to a solution of 9H-fluoren-9-yl quinuclidine-3-carboxylate (100 mg, 0.31 mmol) in acetonitrile (1 ml). The reaction was stirred at room temperature overnight. 2-Chloro-1-(thiophen-2-yl)ethanone (55 mg, 0.34 mmol) was added again, and the mixture stirred at room temperature for 3 hours. The solvent was removed, and the residue was re-dissolved in acetonitrile and heated under microwave irradiation at 100° C. for 3 hours. Acetonitrile was removed, and the residue was triturated with Et$_2$O and then purified by preparative HPLC to obtain 3-((9H-fluoren-9-yloxy)carbonyl)-1-(2-oxo-2-(thiophen-2-yl)ethyl)-1-azoniabicyclo[2.2.2]octane 2,2,2-trifluoroacetate (46 mg, racemic mixture).

$^1$H NMR (300 MHz, DMSO-d6) δ ppm 8.22 (dd, 1H), 8.11 (dd, 1H), 7.87 (d, 2H), 7.55-7.65 (m, 2H), 7.49 (t, 2H), 7.31-7.42 (m, 3H), 6.85 (s, 1H), 5.12 (s, 2H), 4.11-4.27 (m, 1H), 3.85-3.96 (m, 1H), 3.59-3.78 (m, 4H), 3.35-3.52 (m, 1H), 2.39-2.46 (m, 1H), 1.82-2.13 (m, 4H);

LC-MS (ESI POS): 444.30 (M+).

Example 40

Preparation of 4-((bis(3-fluorophenyl)methoxy)carbonyl)-1-methyl-1-(2-oxo-2-(thiophen-2-yl)ethyl)piperidinium chloride (Compound 84)

1. Preparation of bis(3-fluorophenyl)methyl 1-methylpiperidine-4-carboxylate (Compound 83)

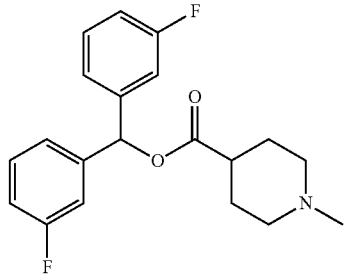 [SMILES: CN1CCC(C(=O)OC(c2cccc(F)c2)c2cccc(F)c2)CC1]

1-Methylpiperidine-4-carboxylic acid hydrochloride (250 mg, 1.39 mmol), EDC (400 mg, 2.09 mmol), and HOBT (320 mg, 2.09 mmol) were dissolved in dry THF (10 ml). Bis(3-fluorophenyl)methanol (337 mg, 1.53 mmol) was dissolved in dry THF (4 ml) and then added to the reaction mixture. Triethylamine (6790, 4.87 mmol) was finally added, and the resulting reaction was stirred at room temperature overnight. The reaction was evaporated, and the residue was taken up with EtOAc and washed with water and sat.NaHCO$_3$. The organic phase was dried over sodium sulfate, filtered, and evaporated under vacuum. The crude was purified by flash chromatography (DCM/MeOH=9/1) to afford bis(3-fluorophenyl)methyl 1-methylpiperidine-4-carboxylate (150 mg).

2. Preparation of 4-((bis(3-fluorophenyl)methoxy)carbonyl)-1-methyl-1-(2-oxo-2-(thiophen-2-yl)ethyl)piperidinium chloride (Compound 84)

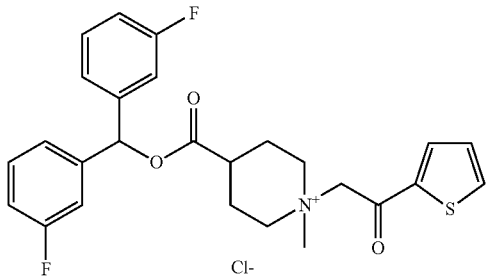 [SMILES: C[N+]1(CC(=O)c2cccs2)CCC(C(=O)OC(c2cccc(F)c2)c2cccc(F)c2)CC1 ; [Cl-]]

To a solution of bis(3-fluorophenyl)methyl 1-methylpiperidine-4-carboxylate (150 mg, 0.43 mmol) in ethyl acetate (5 ml), 2-chloro-1-(thiophen-2-yl)ethanone (69.8 mg, 0.43 mmol) was added, and the mixture was stirred at room temperature overnight. The solvent was removed under vacuum, and the residue was taken up in diethyl ether, filtered, and purified by flash chromatography (DCM/MeOH=95/5) to obtain 4-((bis(3-fluorophenyl)methoxy)carbonyl)-1-methyl-1-(2-oxo-2-(thiophen-2-yl)ethyl)piperidinium chloride (18 mg).
$^1$H NMR (300 MHz, DMSO-d6) δ ppm 8.20 (d, 1H), 8.14 (d, 1H), 7.23-7.54 (m, 7H), 7.04-7.23 (m, 2H), 6.87 (s, 1H), 5.24 (br. s., 2H), 3.90-4.20 (m, 2H), 3.44-3.60 (m, 2H), 3.31 (br. s., 3H), 2.80-3.00 (m, 1H), 1.96-2.32 (m, 4H);
LC-MS (ESI POS): 470.18 (M+).

Example 41

Preparation of 4-((bis(3-fluorophenyl)methoxy)carbonyl)-1-methyl-1-(2-oxo-2-(thiophen-3-yl)ethyl)piperidinium bromide (Compound 85)

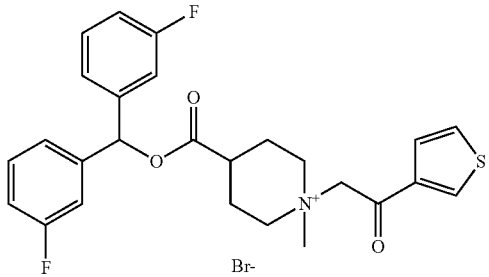 [SMILES: C[N+]1(CC(=O)c2ccsc2)CCC(C(=O)OC(c2cccc(F)c2)c2cccc(F)c2)CC1 ; [Br-]]

2-Bromo-1-(thiophen-3-yl)ethanone (23.7 mg, 0.12 mmol) was added to a solution of bis(3-fluorophenyl)methyl 1-methylpiperidine-4-carboxylate (40 mg, 0.12 mmol, prepared as in example 40) in EtOAc (3 ml). The reaction was stirred at room temperature overnight. The solvent was evaporated, and the crude was purified by preparative HPLC (eluent: CH$_3$CN/H$_2$O) to obtain 4-((bis(3-fluorophenyl)methoxy)carbonyl)-1-methyl-1-(2-oxo-2-(thiophen-3-yl)ethyl)piperidinium bromide (36.1 mg).
$^1$H NMR (300 MHz, DMSO-d6) δ ppm 8.63-8.71 (m, 1H), 7.67-7.83 (m, 1H), 7.50-7.62 (m, 1H), 7.24-7.50 (m, 6H), 7.01-7.24 (m, 2H), 6.87 and 6.88 (s, 1H), 5.17 and 5.20 (s, 2H), 3.73-4.07 (m, 2H), 3.39-3.71 (m, 2H), 3.30 and 3.32 (s, 3H), 2.79-3.05 (m, 1H), 2.11-2.36 (m, 4H);
LC-MS (ESI POS): 470.24 (M+).

Example 42

Preparation of 4-((bis(3-fluorophenyl)methoxy)carbonyl)-1-methyl-1-(2-oxo-2-(thiazol-2-yl)ethyl)piperidinium bromide (Compound 86)

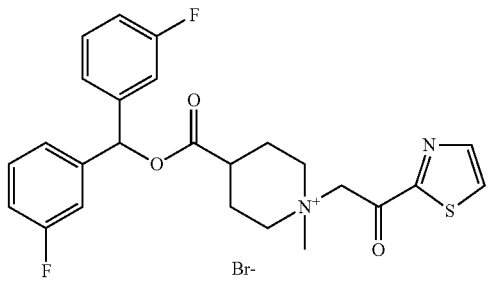 [SMILES: C[N+]1(CC(=O)c2nccs2)CCC(C(=O)OC(c2cccc(F)c2)c2cccc(F)c2)CC1 ; [Br-]]

To a solution of bis(3-fluorophenyl)methyl 1-methylpiperidine-4-carboxylate (106 mg, 0.31 mmol, prepared as in example 40) in EtOAc (3 ml), 2-bromo-1-(thiazol-2-yl)ethanone (63.2 mg, 0.31 mmol) was added. The mixture was stirred at room temperature for 27 hours. The solvent was evaporated, and the crude was triturated with Et$_2$O and collected by filtration. The compound was purified by flash chromatography (DCM/MeOH=95/5 to 9/1) to obtain 4-((bis(3-fluorophenyl)methoxy)carbonyl)-1-methyl-1-(2-oxo-2-(thiazol-2-yl)ethyl)piperidinium bromide (120 mg).
$^1$H NMR (300 MHz, DMSO-d6) δ ppm 8.40 (d, 1H), 8.26 (d, 1H), 7.25-7.55 (m, 6H), 7.02-7.25 (m, 2H), 6.87 (s, 1H), 5.32 and 5.34 (s, 1H), 3.44-4.26 (m, 4H), 3.32 (s, 3H), 2.77-3.05 (m, 1H), 2.00-2.43 (m, 4H);
LC-MS (ESI POS): 471.15 (M+).

Example 43

Preparation of (1r,4r)-4-((1,2-diphenylethoxy)carbonyl)-1-methyl-1-(2-oxo-2-phenylethyl)piperidinium bromide (Compound 88a) and (1s,4s)-4-((1,2-diphenylethoxy)carbonyl)-1-methyl-1-(2-oxo-2-phenylethyl)-piperidinium bromide (Compound 88b).

1. Preparation of 1,2-diphenylethyl 1-methylpiperidine-4-carboxylate (Compound 87)

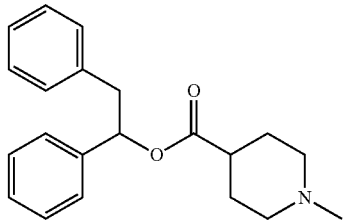 [SMILES: CN1CCC(C(=O)OC(Cc2ccccc2)c2ccccc2)CC1]

Oxalyl dichloride (141 µl, 1.67 mmol) was added dropwise to a solution of 1-methylpiperidine-4-carboxylic acid hydrochloride (300 mg, 1.67 mmol) in DCM (20 ml) and few drops of DMF (catalytic amount). The reaction was stirred at room temperature for 2 hours. The volatiles were removed under vacuum, and the crude was taken up with pyridine (20 ml). 1,2-Diphenylethanol (331 mg, 1.67 mmol) was added, and the resulting suspension was heated under microwave irradiation at 140° C. for 1 hour. Pyridine was removed under vacuum, and the crude was purified by flash chromatography (DCM/MeOH=97/3 to 94/6) to obtain 1,2-diphenylethyl 1-methylpiperidine-4-carboxylate (200 mg).

2. Preparation of (1R,4R)-4-((1,2-diphenylethoxy)carbonyl)-1-methyl-1-(2-oxo-2-phenylethyl)piperidinium bromide (Compound 88a) and (1S,4S)-4-((1,2-diphenylethoxy)carbonyl)-1-methyl-1-(2-oxo-2-phenylethyl)piperidinium bromide (Compound 88b)

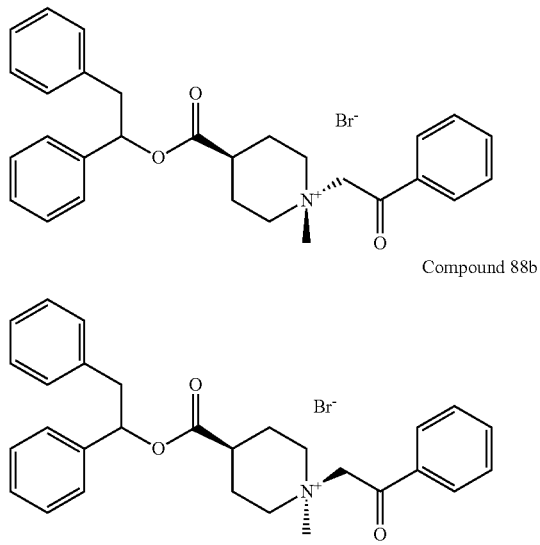

Compound 88a

Compound 88b

2-Bromo-1-phenylethanone (61.5 mg, 0.31 mmol) was added to a solution of 1,2-diphenylethyl 1-methylpiperidine-4-carboxylate (100 mg, 0.31 mmol) in acetonitrile (5 ml). The reaction was stirred at room temperature overnight. The solvent was evaporated, and the crude was purified by flash chromatography (DCM/MeOH=98/2), collecting first (1R,4R)-4-((1,2-diphenylethoxy)carbonyl)-1-methyl-1-(2-oxo-2-phenylethyl)piperidinium bromide (82.3 mg, compound 88a) and then (1S,4S)-4-((1,2-diphenylethoxy)carbonyl)-1-methyl-1-(2-oxo-2-phenylethyl)piperidinium bromide (32.1 mg, compound 88b).

Compound 88a:

$^1$H NMR (300 MHz, DMSO-d6) δ ppm 7.88-8.15 (m, 2H), 7.77 (tt, 1H), 7.50-7.69 (m, 2H), 7.15-7.48 (m, 10H), 5.98 (t, 1H), 5.30 (s, 2H), 3.44-3.84 (m, 4H), 3.27 (s, 3H), 3.10-3.20 (m, 2H), 2.57-2.71 (m, 1H), 1.89-2.18 (m, 4H);

LC-MS (ESI POS): 442.15 (M+).

Compound 88b:

$^1$H NMR (300 MHz, DMSO-d6) δ ppm 8.01 (m, 2H), 7.66-7.83 (m, 1H), 7.50-7.66 (m, 2H), 7.12-7.36 (m, 10H), 5.72-6.10 (m, 1H), 5.25 (s, 2H), 3.89-3.95 (m, 1H), 3.79-3.86 (m, 1H), 3.31-3.66 (m, 2H), 3.26 (s, 3H), 2.98-3.18 (m, 2H), 2.65-2.71 (m, 1H), 1.97-2.13 (m, 4H);

LC-MS (ESI POS): 442.2 (M+).

Example 44

Preparation of (1R,4R)-4-(((E)-1,2-diphenylvinyloxy)carbonyl)-1-methyl-1-(2-oxo-2-phenylethyl)piperidinium bromide (Compound 90)

1. Preparation of (E)-1,2-diphenylvinyl 1-methylpiperidine-4-carboxylate (Compound 89)

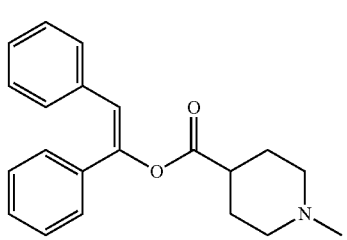 [SMILES: CN1CCC(C(=O)O/C(=C/c2ccccc2)c2ccccc2)CC1]

Oxalyl dichloride (236 µl, 2.78 mmol) was added dropwise to a solution of 1-methylpiperidine-4-carboxylic acid hydrochloride (500 mg, 2.78 mmol) in DCM (30 ml) and few drops of DMF (catalytic amount). The reaction was stirred at room temperature for 2 hours. The volatiles were removed under vacuum, and the crude was taken up with pyridine (40 ml). 1,2-Diphenylethanone (546 mg, 2.78 mmol) was added, and the resulting suspension was heated under microwave irradiation at 140° C. for 1 hour. Pyridine was removed under vacuum, and the crude was purified by flash chromatography (DCM/MeOH=95/5) to obtain (E)-1,2-diphenylvinyl 1-methylpiperidine-4-carboxylate (62 mg).

2. Preparation of (1R,4R)-4-(((E)-1,2-diphenylvinyloxy)carbonyl)-1-methyl-1-(2-oxo-2-phenylethyl)piperidinium bromide (Compound 90)

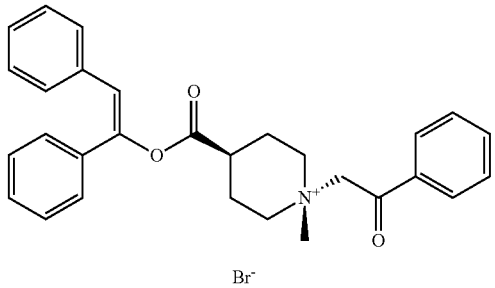 [SMILES: C[N@+]1(CC(=O)c2ccccc2)CC[C@H](C(=O)O/C(=C/c2ccccc2)c2ccccc2)CC1 ; [Br-]]

2-Bromo-1-phenylethanone (57.6 mg, 0.29 mmol) was added to a solution of (E)-1,2-diphenylvinyl 1-methylpiperidine-4-carboxylate (62 mg, 0.19 mmol) in acetonitrile (3 ml). The reaction was stirred at room temperature overnight, and then the solvent was evaporated. The crude was purified by flash chromatography (DCM/MeOH=98/2) and then by flash chromatography (DCM/MeOH=99/1) to obtain (1R,4R)-4-(((E)-1,2-diphenylvinyloxy)carbonyl)-1-methyl-1-(2-oxo-2-phenylethyl)piperidinium bromide (18 mg).

$^1$H NMR (300 MHz, DMSO-d6) δ ppm 7.96-8.08 (m, 2H), 7.73-7.84 (m, 1H), 7.60-7.70 (m, 4H), 7.52-7.60 (m, 2H), 7.38-7.50 (m, 5H), 7.28-7.36 (m, 1H), 7.06 (s, 1H), 5.36 (s, 2H), 3.77-3.95 (m, 2H), 3.60-3.76 (m, 2H), 3.36 (s, 3H), 3.12 (tt, 1H), 2.10-2.42 (m, 4H);

LC-MS (ESI POS): 440.23 (M+).

Example 45

Preparation of 4-((3-fluorobenzyloxy)carbonyl)-1-(2-oxo-2-(thiophen-2-yl)ethyl)-1-azoniabicyclo[2.2.2]octane chloride (Compound 92)

1. Preparation of 3-fluorobenzyl quinuclidine-4-carboxylate (Compound 91)

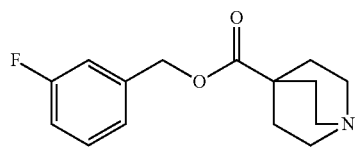 [SMILES: O=C(OCc1cccc(F)c1)C12CCN(CC1)CC2]

A mixture of quinuclidine-4-carboxylic acid hydrochloride (100 mg, 0.52 mmol) and thionyl chloride (500 µl, 6.85 mmol) was refluxed for 2 hours. The reaction was cooled to room temperature, and the solvent was accurately removed. The residue was suspended in dry DCM and treated with (3-fluorophenyl)methanol (65.8 mg, 0.52 mmol). The reaction was stirred at room temperature for 24 hours. The solvent was evaporated, and the residue was dissolved in water (1 ml), basified with NaHCO$_3$ and extracted twice with EtOAc. The combined organic layers were dried over Na$_2$SO$_4$, filtered, and evaporated to obtain 3-fluorobenzyl quinuclidine-4-carboxylate (41 mg, 29.8% yield), which was used in the next step without any further purification.

2. Preparation of 4-((3-fluorobenzyloxy)carbonyl)-1-(2-oxo-2-(thiophen-2-yl)ethyl)-1-azoniabicyclo[2.2.2]octane chloride (Compound 92)

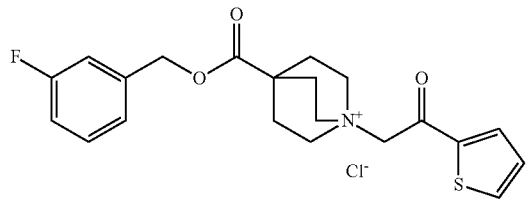 [SMILES: O=C(C[N+]12CCC(C(=O)OCc3cccc(F)c3)(CC1)CC2)c1cccs1 ; [Cl-]]

To a solution of 3-fluorobenzyl quinuclidine-4-carboxylate (41 mg, 0.16 mmol) dissolved in EtOAc (2 ml), 2-chloro-1-(thiophen-2-yl)ethanone (20.0 mg, 0.12 mmol) was added. The reaction was stirred at room temperature for three days, and then the precipitate was collected by suction filtration to obtain 4-((3-fluorobenzyloxy)carbonyl)-1-(2-oxo-2-(thiophen-2-yl)ethyl)-1-azoniabicyclo[2.2.2]octane chloride (30 mg, 45.4% yield).

$^1$H NMR (300 MHz, DMSO-d6) δ ppm 8.21 (dd, 1H), 8.01-8.17 (m, 1H), 7.39-7.58 (m, 1H), 7.35 (dd, 1H), 7.06-7.28 (m, 3H), 5.18 (s, 2H), 4.97-5.13 (m, 2H), 3.68-3.87 (m, 6H), 2.04-2.30 (m, 6H);

LC-MS (ESI POS): 388.21 (M+).

Example 46

Preparation of 3-(benzylthiocarbonyl)-1-(2-oxo-2-(thiophen-2-yl)ethyl)-1-azoniabicyclo[2.2.2]octane chloride (Compound 94)

1. Preparation of S-benzyl quinuclidine-3-carbothioate (Compound 93)

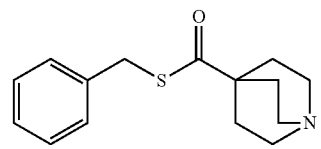 [SMILES: O=C(SCc1ccccc1)C12CCN(CC1)CC2]

Quinuclidine-3-carboxylic acid hydrochloride (55 mg, 0.29 mmol), EDC (83 mg, 0.43 mmol), and HOBT (65.9 mg, 0.43 mmol) were dissolved in dry THF (5 ml) under a nitrogen atmosphere. Triethylamine (140 µl, 1.00 mmol) and phenylmethanethiol (37.1 µl, 0.32 mmol) were dissolved in dry THF (2 ml) and then added to the reaction mixture. The resulting suspension was stirred at room temperature overnight. The mixture was evaporated, and the crude partitioned between EtOAc and water. The organic phase was washed with saturated NaHCO$_3$, dried over sodium sulfate, filtered, and evaporated under vacuum to obtain S-benzyl quinuclidine-3-carbothioate (110 mg, crude), which was used in the next step without any further purification.

2—Preparation of 3-(benzylthiocarbonyl)-1-(2-oxo-2-(thiophen-2-yl)ethyl)-1-azoniabicyclo[2.2.2]octane chloride (Compound 94)

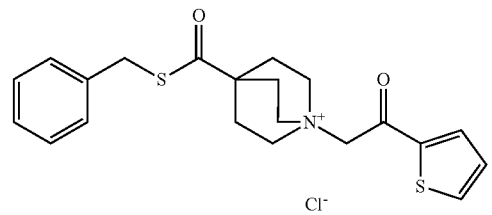 [SMILES: O=C(C[N+]12CCC(C(=O)SCc3ccccc3)(CC1)CC2)c1cccs1 ; [Cl-]]

2-Chloro-1-(thiophen-2-yl)ethanone (68.0 mg, 0.42 mmol) was added to a solution of S-benzyl quinuclidine-3-carbothioate (100 mg, 0.38 mmol) in acetonitrile (1 ml). The reaction was stirred at room temperature overnight, then a second portion of 2-chloro-1-(thiophen-2-yl)ethanone (68.0 mg, 0.42 mmol) was added, and the reaction was stirred at room temperature for additional 3 hours. The solvent was removed in vacuo, and the residue was dissolved in acetonitrile and heated under microwave irradiation at 100° C. for 3 hours. Acetonitrile was removed, and the residue was triturated with Et$_2$O. The crude was then purified by a preparative HPLC (eluent: CH$_3$CN/H$_2$O) to obtain 3-(benzylthiocarbonyl)-1-(2-oxo-2-(thiophen-2-yl)ethyl)-1-azoniabicyclo[2.2.2]octane chloride (8.9 mg, 5.5% yield).

$^1$H NMR (300 MHz, DMSO-d6) δ ppm 8.17 (d, 1H), 7.81 (d, 1H), 7.24-7.42 (m, 5H), 7.20 (dd, 1H), 5.23 (s, 2H), 4.24-4.33 (m, 2H), 4.25 (d, 1H), 4.19 (d, 1H), 3.94-4.14 (m, 3H), 3.71-3.87 (m, 1H), 3.38-3.52 (m, 1H), 2.52-2.67 (m, 1H), 2.07-2.36 (m, 2H), 1.81-2.07 (m, 2H);

LC-MS (ESI POS): 396.29 (M+).

LEGEND

*NMR
s=singlet
d=doublet
t=triplet
q=quartet
dd=doublet of doublets
m=multiplet
br=broad
Biological Characterization.

The interaction with M3 muscarinic receptors can be estimated by the results of in vitro studies which evaluated the M3/M2 binding assays, the potency of the test compounds and the offset of the inhibitory activity produced after washout of the antagonists in isolated guinea pig trachea and by the in vivo duration of action against acetylcholine-induced bronchospasm in the guinea pig.

Example 47

M3/M2 Binding Assays

CHO-K1 clone cells expressing the human M2 or M3-receptors (Swissprot P08172, P20309 respectively) were harvested in $Ca^{++}/Mg^{++}$ free phosphate-buffered saline and collected by centrifugation at 1500 rpm for 3 minutes. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 minutes at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non selective muscarinic radioligand [$^3$H]-N-methyl scopolamine (Mol. Pharmacol., vol. 45, pp. 899-907, which is incorporated herein by reference in its entirety) was used to label the M2 and M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 W. Samples (final volume 0.75 ml) were incubated at room temperature for 60 minutes for M2 and 90 minutes for M3 binding assay. The reaction was terminated by rapid filtration through GF/B Unifilter plates and two washes (0.75 ml) with cold buffer C using a Packard Filtermate Harvester. Radioactivity on the filters was measured by a microplate scintillation counter TriCarb 2500 (PerkinElmer).

The values of inhibitory M3 activity tested on compounds are comprised between 0.265 and 1514 nM.

Example 48

In Vitro Interaction with the M3 Receptors

The potency of the antagonist activity in isolated guinea pig trachea was investigated following a method previously described by Haddad E B et al. in Br. J. Pharmacol., vol. 127, pp. 413-420 (1999), which is incorporated herein by reference in its entirety, with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction ($IC_{50}$) was taken as a measure of its potency in this bioassay.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 μM) was administered again (at 30 minute interval between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%.

Example 49

In Vivo Studies

The in vivo tests on acetylcholine-induced bronchospasm in guinea pig were performed according to H. Konzett H and Rössler F, Arch. Exp. Path. Pharmacol., vol. 195, pp. 71-74 (1940), which is incorporated herein by reference in its entirety. Aqueous solutions of the test compounds were instilled intratracheally in anaesthetised mechanically ventilated guinea pigs. Bronchial response to intravenous acetylcholine challenge was determined before and after drug administration, and changes in pulmonary resistance at several time-points were expressed as percent of inhibition of bronchospasm.

The bronchodilator activity of the tested compounds persisted unchanged up to 24 hours after the administration.

Example 50

Lung Stability

Firstly, fresh rat lungs (previously, washed in saline) are homogenized in Amm. Formiate Buffer 20 mM. In order to demonstrate that the compounds are degraded, stability in lung homogenate at 1 and 5 hours was tested for the compound of the invention. Briefly 10 μl of a stock solution 250 μM of the compound in acetonitrile were added to 1 ml of lung homogenate, and samples were incubated at 37° C. Lung homogenate (50 μL) was taken after 0, 1 and 5 hours of incubation and added to 200 μl of acetonitrile with addition of verapamil as internal standard (250 ng/ml). Samples were analysed by HPLC-MS/MS analysis. Lung stability is calculated as percentage remaining after 1 and 5 hours by dividing the peak area at 1 or 5 hours by the area of the peak at time 0.

More than 79% of tested compounds could be still detected after 1 hour of incubation and more than 57% after 5 hours, indicating these compounds are stable in presence of homogenated lung.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

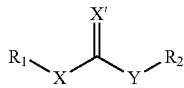 (I)

wherein:
X is O or S;
X' is O or S;
Y is NH or absent;
$R_1$ is aryl, heteroaryl, aryl($C_1$-$C_6$)alkyl, heteroaryl($C_1$-$C_6$) alkyl, or a group of formula (a) or (b):

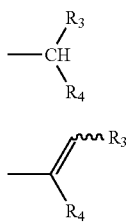

wherein
$R_3$ and $R_4$ are the same or different and may be independently H or are selected from the group consisting of ($C_3$-$C_8$)cycloalkyl, aryl, aryl($C_1$-$C_6$)alkyl, heteroaryl, and heteroaryl($C_1$-$C_6$)alkyl, each which may be optionally substituted by one or more substituents selected from the group consisting of a halogen atom, —OH, ($C_1$-$C_6$)haloalkyl, ($C_1$-$C_6$)alkoxy, oxo (=O), —SH, —$NO_2$, —CN, —$CONH_2$, —COOH, ($C_1$-$C_6$) alkoxycarbonyl, ($C_1$-$C_6$)alkylsulfanyl, ($C_1$-$C_6$)alkylsulfinyl, ($C_1$-$C_6$)alkylsulfonyl and ($C_1$-$C_6$)alkyl or, when $R_3$ and $R_4$ are both independently aryl or heteroaryl they may be linked to each other through a ($CH_2$)$_r$ group wherein r=0, 1, or 2, to form a tricyclic ring system wherein any of the methylene ($CH_2$)$_r$ groups may be optionally replaced by a heteroatom or heteroaromatic group selected from O, S, N and NH, and with the proviso that $R_3$ and $R_4$ are not simultaneously H;
$R_2$ is a group of formula (c) or (d):

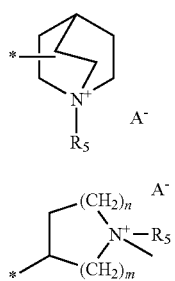

wherein
m=1, 2 or 3;
n=1, 2 or 3;
$A^-$ is a physiologically acceptable anion;

$R_5$ is a group of formula (e):

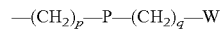 (e)

wherein
p is 0 or an integer from 1 to 4;
q is 0 or an integer from 1 to 4;
P is absent or is selected from the group consisting of —O—, —S—, —S(O)—, —S($O_2$)—, —C(O)—, —CO(O)—, —N($R_6$)—, —CH=CH—, —N($R_6$)($SO_2$)—, —N($R_6$)CO(O)—, —N($R_6$)C(O)—, —$SO_2$N($R_6$)—, —CO(O)N($R_6$)— and —C(O)N ($R_6$)—;
W is H or is selected from the group consisting of ($C_1$-$C_6$)alkyl, ($C_2$-$C_6$)alkenyl, ($C_3$-$C_8$)cycloalkyl, ($C_3$-$C_8$) heterocycloalkyl, aryl and heteroaryl, each of which is optionally substituted by one or more substituents selected from the group consisting of a halogen atom, —OH, oxo (=O), —SH, —$NO_2$, —N($R_6$)$_2$, —CN, —CON($R_6$)$_2$, —COOH, —NHCO$R_6$, $CO_2R_6$, ($C_1$-$C_6$)alkoxycarbonyl, ($C_1$-$C_6$)alkylsulfanyl, ($C_1$-$C_6$) alkylsulfinyl, ($C_1$-$C_6$)alkylsulfonyl, ($C_1$-$C_6$)alkyl, ($C_1$-$C_6$)alkoxy, aryl, and heteroaryl;
$R_6$ is, independently in each occurrence, H or is selected from the group consisting of ($C_1$-$C_6$)alkyl, ($C_1$-$C_6$) haloalkyl, ($C_2$-$C_6$)alkynyl, ($C_2$-$C_6$)alkenyl, ($C_3$-$C_8$) cycloalkyl, heteroaryl, and aryl, each of which is optionally substituted by one or more substituents selected from the group consisting of halogen atoms, —OH, oxo (=O), —SH, —$NO_2$, —CN, —$CONH_2$, —COOH, ($C_1$-$C_6$)alkoxycarbonyl, ($C_1$-$C_6$)alkylsulfanyl, ($C_1$-$C_6$)alkylsulfinyl, ($C_1$-$C_6$)alkylsulfonyl, ($C_3$-$C_8$)cycloalkyl, ($C_1$-$C_6$)alkyl, and ($C_1$-$C_6$)alkoxy;
or a pharmaceutically acceptable salt thereof.

2. A compound or salt according to claim 1, which is a compound represented by formula (IA):

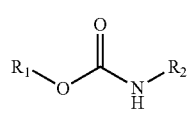 (IA)

wherein:
$R_1$ is a group of formula (a), wherein $R_3$ and $R_4$ are the same or different and are independently H or selected from the group consisting of aryl and heteroaryl, each of which may be optionally substituted by one or more substituents selected from the group consisting of a halogen atom, ($C_1$-$C_6$)alkoxy, and ($C_1$-$C_6$)haloalkyl, and
$R_2$ is a group of formula (c) or (d):

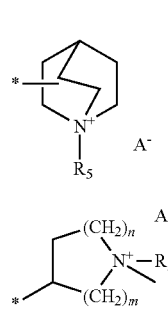

wherein n=m=1 and $R_5$ is a group of formula (e) wherein p is 0, 1, 2 or 3, P is absent or is selected from the group consisting of —O—, —C(=O)—, and —C(=O)N (H)—, q is 0, 1, or 2, and W is selected from the group consisting of $(C_1-C_6)$alkyl, $(C_2-C_6)$alkenyl, aryl, and heteroaryl, each of which is optionally substituted by one or more substituents selected from the group consisting of a halogen atom, —OH, —CN, $(C_1-C_6)$alkyl, and $(C_1-C_6)$alkoxy, or a pharmaceutically acceptable salt thereof.

3. A compound or salt according to claim 1, wherein:

$R_1$ is bis(3-fluorophenyl)methyl, benzhydryl, bis(4-fluorophenyl)methyl, (4-methoxyphenyl)(phenyl)methyl, -(2-fluorophenyl)(4-fluorophenyl)methyl), (3,4-difluorophenyl)(phenyl)-methyl, (4-(trifluoromethyl)phenyl)methyl, (2-chlorophenyl)(4-chlorophenyl)methyl. or thiophen-2-ylmethyl; and $R_2$ is (2-oxo-2-(thiophen-3-yl)ethyl)-1-azoniabicyclo[2.2.2]octanyl, (2-(4-chlorophenyl)-2-oxoethyl)-1-azonia-bicyclo[2.2.2]octanyl, (2-oxo-2-p-tolylethyl)-1-azoniabicyclo[2.2.2]octanyl, (2-(4-fluorophenyl)-2-oxoethyl)-1-azoniabicyclo[2.2.2]octanyl, (2-(3-fluorophenyl)-2-oxoethyl)-1-azoniabicyclo[2.2.2]octanyl, (2-(2-fluorophenyl)-2-oxoethyl)-1-azoniabicyclo[2.2.2]octanyl, (2-(4-methoxyphenyl)-2-oxoethyl)-1-azoniabicyclo[2.2.2]octanyl, (2-(4-hydroxyphenyl)-2-oxoethyl)-1-azoniabicyclo[2.2.2]octanyl, (bis(3-fluorophenyl)methoxy)-carbonylamino)-1-azoniabicyclo[2.2.2]octanyl, (2-(5-chlorothiophen-2-yl)-2-oxoethyl)-1-azoniabicyclo[2.2.2]octanyl, (2-oxo-2-(thiazol-2-yl)ethyl)-1-azoniabicyclo-[2.2.2]octanyl, (2-oxopropyl)-1-azoniabicyclo-[2.2.2]octanyl, (3-methylbut-2-enyl)-1-azoniabicyclo[2.2.2]octanyl, benzyl-1-azoniabicyclo[2.2.2]octanyl, (3-phenoxypropyl)-1-azoniabicyclo-[2.2.2]octanyl, (2-(5-cyanothiophen-2-yl)-2-oxoethyl)-1-azoniabicyclo-[2.2.2]octanyl, (2-oxo-2-(pyridin-2-yl)ethyl)-1-azoniabicyclo[2.2.2]-octanyl, (2-(isoxazol-3-ylamino)-2-oxoethyl)-1-azoniabicyclo[2.2.2]-octanyl, (2-oxo-2-(thiophen-2-yl)ethyl)-1-azoniabicyclo-[2.2.2]octanyl, (2-oxo-2-phenylethyl)-1-azoniabicyclo[2.2.2]octanyl, (2-phenoxyethyl)-1-azoniabicyclo[2.2.2]octanyl, (2,3-dihydrobenzofuran-5-yl)ethyl)-1-azoniabicyclo[2.2.2]octanyl, (4-fluorophenethyl)-1-azoniabicyclo-[2.2.2]-octanyl, or benzyl-methylpyrrolidinyl.

4. A compound or salt according to claim 1, which is a compound represented by formula (IB):

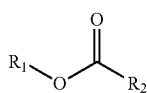

(IB)

wherein $R_1$ is aryl or a group of formula (a) or (b) wherein $R_3$ and $R_4$ are the same or different and are independently H or selected from the group consisting of aryl, aryl($C_1-C_6$)alkyl, and heteroaryl, each which may be optionally substituted by one or more substituents selected from the group consisting of a halogen atom, $(C_1-C_6)$alkoxy, and $(C_1-C_6)$haloalkyl or when $R_3$ and $R_4$ are both independently aryl or heteroaryl they may be linked to each other through a $(CH_2)_r$ group wherein r=0, 1, or 2, to form a tricyclic ring system wherein any of the methylene $(CH_2)_r$ groups may be substituted by a heteroatom or heteroaromatic group selected from O, S, N and NH and with the proviso that $R_3$ and $R_4$ are not simultaneously H, and $R_2$ is a group of formula (c) or (d):

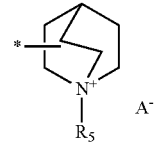

(c)

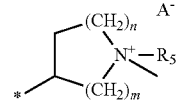

(d)

wherein n=1 or 2, m=1 and $R_5$ is a group of formula (e), wherein p=1 or 3, P is absent or is selected from the group consisting of —O—, —C(=O)— and —C(=O)O—, q=1 and W is selected from the group consisting of $(C_1-C_6)$alkyl, $(C_2-C_6)$alkenyl, aryl, and heteroaryl each of which is optionally substituted by one or more substituents selected from the group consisting of halogen atoms, —OH, —CN, $(C_1-C_6)$alkyl, $(C_1-C_6)$alkoxycarbonyl, and $(C_1-C_6)$alkoxy.

5. A compound or salt according to claim 1, wherein $R_1$ is bis(3-fluorophenyl)methyl, 1,2-diphenylethyl, bis(4-chlorophenyl)methyl, bis(4-fluorophenyl)methyl, (4-methoxyphenyl)-(phenyl)methyl, 3-fluorobenzyl, 1,2-diphenylvinyl, 3-fluorobenzyl, benzyl, (3,4-difluorophenyl)(phenyl)methyl, fluorenyl, or diphenylvinyl; and $R_2$ is 2-oxo-2-phenylethyl-1-azoniabicyclo[2.2.2]octanyl, 2-oxo-2-(thiophen-2-yl)ethyl-1-azoniabicyclo[2.2.2]octanyl, 2-oxo-2-(thiophen-3-yl)ethyl-1-azoniabicyclo[2.2.2]octanyl, 2-(4-methoxyphenyl)-2-oxoethyl)-1-azoniabicyclo[2.2.2]octanyl, 2-(4-fluorophenyl)-2-oxoethyl)-1-azoniabicyclo-[2.2.2]octanyl, 2-oxo-2-p-tolylethyl)-1-azoniabicyclo[2.2.2]octanyl, 2-(5-chlorothiophen-2-yl)-2-oxoethyl)-1-azoniabicyclo[2.2.2]octanyl, 2-(4-chlorophenyl)-2-oxoethyl-1-azoniabicyclo[2.2.2]octanyl, 1-(2-oxopropyl)-1-azoniabicyclo[2.2.2]octanyl, 1-(2-tert-butoxy-2-oxoethyl)-1-azoniabicyclo-[2.2.2]octanyl, 1-(2-oxo-2-(pyridin-2-yl)ethyl)-1-azoniabicyclo[2.2.]octanyl, 1-(2-(3-(ethoxycarbonyl)isoxazol-5-yl)-2-oxoethyl)-1-azoniabicyclo[2.2.2]-octanyl, 1-(2-(4-hydroxyphenyl)-2-oxoethyl)-1-azoniabicyclo[2.2.2]octanyl, 1-(2-(benzothiophen-5-yl)-2-oxoethyl)-1-azoniabicyclo[2.2.2]octanyl, 1-benzyl-1-azoniabicyclo[2.2.2]octanyl, 1-(2-oxo-2-(thiophen-2-yl)ethyl)-1-1azoniabicyclo[2.2.2]octanyl, or 1-methyl-1-(2-oxo-2-(thiophen-2-yl)ethyl)piperidinyl.

6. A compound of formula (IV):

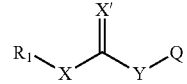

(IV)

wherein

Q represents a group of formula (f) or (g):

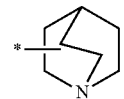

(f)

-continued

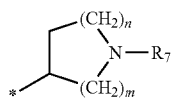 (g)

wherein $R_7$ is $(C_1-C_6)$alkyl or aryl$(C_1-C_6)$alkyl, and $R_1$, X, X', n, m and Y are as defined in claim 1, or a pharmaceutically acceptable salt thereof.

7. A compound or salt according to claim 6, which is a compound represented by formula (IVA):

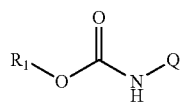 (IVA)

wherein
$R_1$ is a group of formula (a):

 (a)

$R_3$ and $R_4$ are the same or different and are independently H or selected from the group consisting of aryl and heteroaryl, each of which may be optionally substituted by one or more substituents selected from the group consisting of a halogen atom, $(C_1-C_6)$alkoxy, and $(C_1-C_6)$haloalkyl; and
Q is a group of formula (f) or (g):

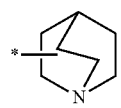 (f)

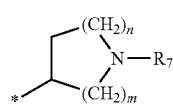 (g)

wherein $R_7$ is aryl$(C_1-C_6)$alkyl,
or a pharmaceutically acceptable salt thereof.

8. A compound or salt according to claim 6, which is a compound represented by formula (IVB):

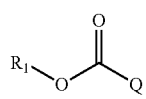 (IVB)

wherein
$R_1$ is aryl or a group of formula (a), wherein $R_3$ and $R_4$ are the same or different and are independently H or selected from the group consisting of aryl, aryl$(C_1-C_6)$alkyl, and heteroaryl, each of which may be optionally substituted by one or more substituents selected from the group consisting of halogen atoms, $(C_1-C_6)$alkoxy, and $(C_1-C_6)$haloalkyl or when $R_3$ and $R_4$ are both independently aryl or heteroaryl they may be linked to each other through a $(CH_2)_r$ group wherein r=0, 1, or 2, to form a tricyclic ring system wherein any of the methylene $(CH_2)$, groups may be a heteroatom or heteroaromatic group selected from O, S, N and NH, and with the proviso that $R_3$ and $R_4$ are not simultaneously H; and
Q is a group of formula (f) or (g):

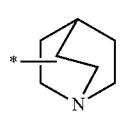 (f)

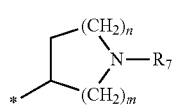 (g)

wherein n is 1, m is 2 and $R_5$ is a group of formula (f) wherein p=0, P is absent, q is 0 or 1 and W is $(C_1-C_6)$ alkyl,
or a pharmaceutically acceptable salt thereof.

9. A pharmaceutical composition, comprising a compound or salt according to claim 1 and one or more pharmaceutically acceptable carriers and/or excipients.

10. A combination of a compound or salt according to claim 1 and one or more active ingredients selected from the group consisting of a beta2-agonist, a corticosteroid, a P38 MAP kinase inhibitor, a IKK2 inhibitor, a HNE inhibitor, a PDE4 inhibitor, a leukotriene modulator, a NSAID, and a mucus regulator.

11. A pharmaceutical composition according to claim 9, which is in a form suitable for administered by inhalation.

12. A pharmaceutical composition according to claim 11, which is an inhalable powder, a propellant-containing metering aerosol, or a propellant-free inhalable formulation.

13. A device, comprising a pharmaceutical composition according to claim 11, wherein said device is a single- or multi-dose dry powder inhaler, a metered dose inhaler, or a soft mist nebulizer.

14. A method for treating a broncho-obstructive or inflammatory disease, comprising administering an effective amount of a compound or salt according to claim 1 to a subject in need thereof.

15. A method according to claim 14, wherein said disease is asthma, chronic bronchitis, or chronic obstructive pulmonary disease.

* * * * *